United States Patent [19]
Starrett, Jr. et al.

[11] Patent Number: 5,618,839
[45] Date of Patent: Apr. 8, 1997

[54] RETINOID-LIKE COMPOUNDS

[75] Inventors: John E. Starrett, Jr., Middletown; Kuo-Long Yu, Hamden, both of Conn.; Muzammil M. Mansuri, Lexington, Mass.; David R. Tortolani, Princeton, N.J.; Peter R. Reczek, East Amherst, N.Y.

[73] Assignee: Bristol-Myers Squibb Company, Princeton, N.J.

[21] Appl. No.: 643,142

[22] Filed: May 2, 1996

Related U.S. Application Data

[60] Division of Ser. No. 464,186, Jun. 5, 1995, which is a continuation-in-part of Ser. No. 306,092, Sep. 19, 1994, abandoned, which is a continuation-in-part of Ser. No. 216,740, Mar. 23, 1994, abandoned, which is a continuation-in-part of Ser. No. 176,746, Jan. 3, 1994, abandoned.

[51] Int. Cl.$^6$ .................... A61K 31/21; A61K 31/185; C07C 229/34

[52] U.S. Cl. .................... 514/513; 514/553; 514/562; 514/563; 514/569; 560/16; 560/48; 560/80; 560/102; 562/427; 562/457; 562/480; 562/490

[58] Field of Search .................... 514/513, 553, 514/562, 563, 569; 560/16, 48, 80, 102; 562/427, 457, 480, 490

[56] References Cited

U.S. PATENT DOCUMENTS

| | | | |
|---|---|---|---|
| 3,973,030 | 8/1976 | Bowman et al. | 514/411 |
| 4,703,110 | 10/1987 | Shudo et al. | 534/566 |

FOREIGN PATENT DOCUMENTS

| | | |
|---|---|---|
| 0337689A1 | 10/1989 | European Pat. Off. |
| WO84/03505 | 9/1984 | WIPO. |
| WO93/06086 | 4/1993 | WIPO. |
| WO93/21146 | 10/1993 | WIPO. |

OTHER PUBLICATIONS

Jia-Yang Chen, et al, "RAR-specific agonist/antagonists which dissociate transactivation and AP1 transrepression inhibit anchorage–independent cell proliferation", The EMBO Journal, 14, No. 6, pp. 1187–1197, 1995.

J.W. Coffey, et al, "Chapater 20. Retinoids as Potential Antirheumatic Agents", Chemistry and Biology of Synthetic Retinoids, M. I. Dawson and W.H. Okamura (eds.), pp. 520–537, 1990.

P. Fritsch, et al, "Arotinoid in Psoriatic Arthropathy", Retinoids: New Trends in Research and Therapy, Retinoid Symposium, Geneva, 1984, J.H. Saurat (ed.) pp. 384–390.

H. Kagechika, et al, "Retinobenzoic Acids. 1. Structure–Activity Relationships of Aromatic Amides with Retinoidal Activity", J. Med. Chem., 31, No. 11, pp. 2182–2192, 1988.

A. Lassus, et al, "Treatment of Reiter's Disease with Etretinate", Retinoids: New Trends in Research and Therapy, Retinoid Symposium, Geneva, 1984, J.H. Saurat (ed.) pp. 391–396.

Peter Loeliger, et al, "Arotinoids, a New Class of Highly Active Retinoids", Eur. J. Med. Chem., 15, No. 1, pp. 9–15, 1980.

*Primary Examiner*—Joseph Conrad
*Attorney, Agent, or Firm*—David M. Morse

[57] ABSTRACT

The present invention relates to a compound of formula I

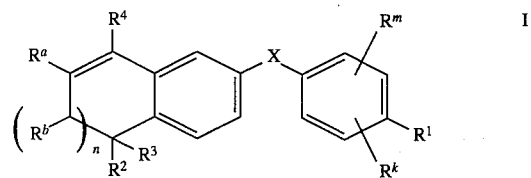

or a nontoxic pharmaceutically acceptable salt, physiologically hydrolyzable ester or solvate thereof, in which X is —O—CO—, —NH—CO—, —CS—NH—, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

R$^m$ and R$^k$ are independently hydrogen, halogen, C$_{1-6}$alkyl, hydroxy, C$_{1-6}$alkyloxy or nitro;

n is zero or one;

R$^4$ is —(CH$_2$)$_t$—Y, C$_{1-6}$alkyl, or C$_{3-6}$cycloalkyl;

R$^1$ is —CO$_2$Z, C$_{1-6}$alkyl, CH$_2$OH, —CONHR$^y$, or CHO;

R$^2$ and R$^3$ are independently hydrogen or C$_{1-6}$alkyl;

R$^a$ and R$^b$ are independently hydrogen or C$_{1-6}$alkyl; but when n is one, R$^a$ and R$^b$ together can form a radical of the formula

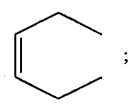

Y is naphthyl or phenyl, both radicals can be optionally substituted with one to three same or different C$_{1-6}$alkyl or halogen;

Z is hydrogen or C$_{1-6}$alkyl;

R$^5$, R$^6$ and R$^y$ are independently hydrogen or C$_{1-6}$alkyl; and t is zero to six.

46 Claims, 4 Drawing Sheets

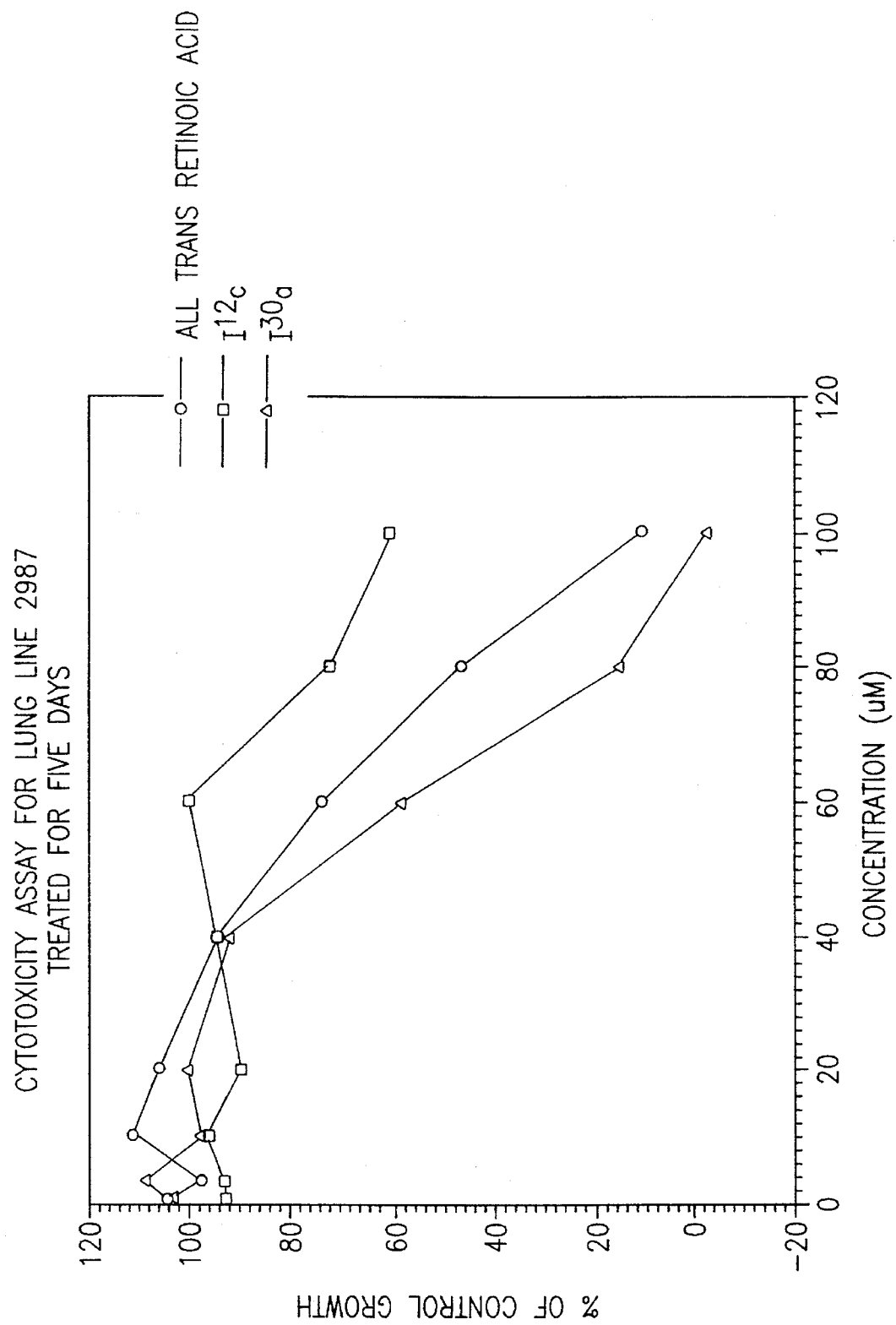

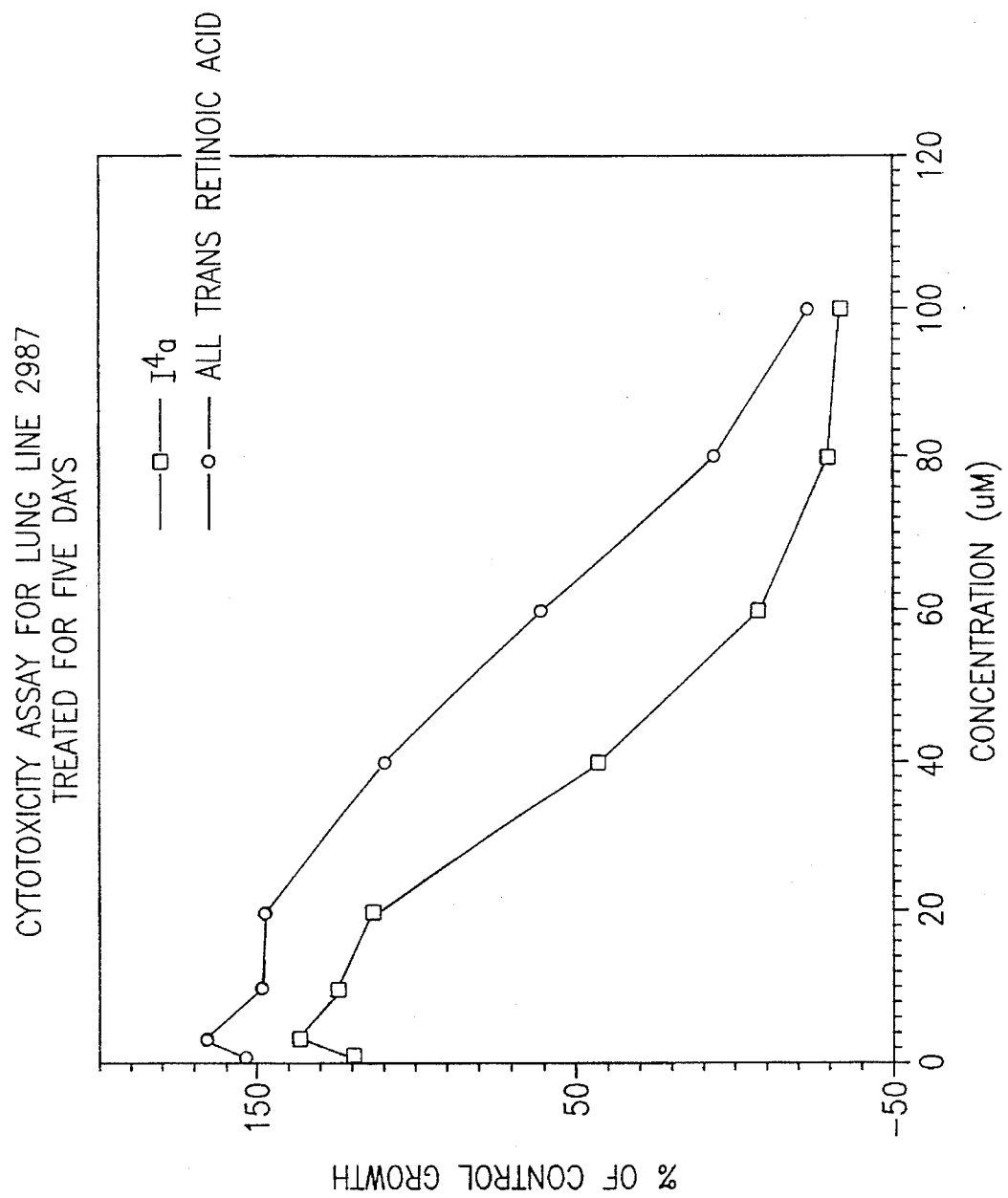

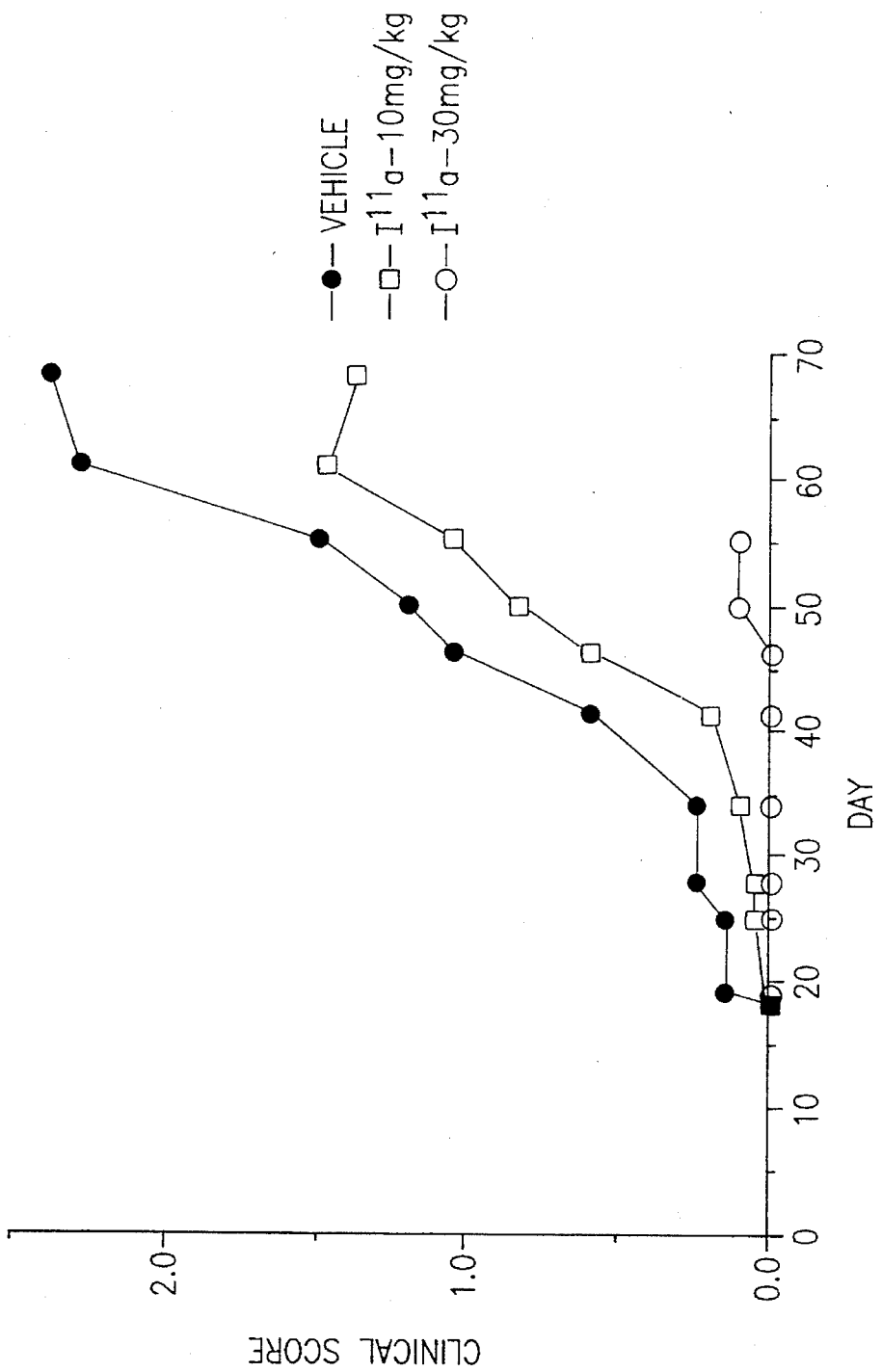

RETINOID-LIKE COMPOUNDS

CROSS REFERENCE TO RELATED APPLICATION

This is a division of copending application(s) U.S. Ser. No. 08/464,186 filed Jun. 5, 1995 which is a CIP of 08/306,092 filed Sep. 19, 1994 now abandoned, which is a CIP of 08/216,740 filed Mar. 23, 1994, abandoned which is a CIP of 08/176,746 filed Jan. 3, 1994, abandoned, all previous applications are herein incorporated by reference in their entirety.

FIELD OF INVENTION

The present invention provides compounds having retinoid-like activity. More specifically, the compounds of the present invention are useful for preventing and/or treating various skin disorders, such as, but not limited to, acne, psoriasis and damage from irradiation. Further, they have antitumor and antiarthritic activites.

BACKGROUND OF THE INVENTION

Retinoic acid and its natural and synthetic analogues (retinoids) exert a wide array of biological effects.

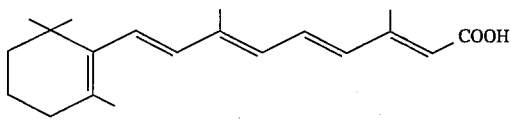

Retinoic Acid

They have been shown to affect cellular growth and differentiation and are promising drugs for the treatment of several cancers. Roberts, A. B. and Sporn, M. B. in "The Retinoids," Sporn, M. B., Roberts, A. B., and Goodman, D. S., eds, 1984, 2, pp. 209–286, Academic Press, New York; Lippman, S. M., Kessler, J. F., and Meyskens, F. L., *Cancer Treat. Rep.*, 1987, 71, p. 391; ibid., p. 493; Hong, W. K. et al., *N. Engl. J. Med.*, 1990, 323, p. 795; Huang, M. et al., *Blood*, 1988, 72, p. 567. Retinods have also been shown to be useful in treating rheumatic diseases, see for example: J. W. Coffey et al., *Retinoids as Potential Antirheumatic Agents*, Chemistry and Biology of Synthetic Retinoids, pp 520–537, CRC Press Inc., M. I. Dawson and W. H. Okamura Ed.(1990)

A few retinoids are already in clininal use in the treatment of dermatological diseases such as acne and psoriasis. For example, isotretinoin is used clinically for oral therapy of severe acne, and etretinate is particularly useful in the treatment of psoriasis. Orfanos, C. E., Ehlert, R., and Gollnick, H., *Drugs*, 1987, 34, pp. 459–503.

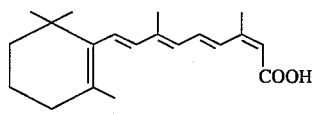

ISOTRETINOIN

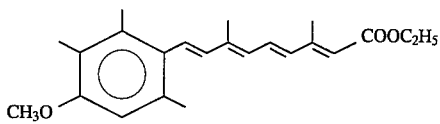

ETRETINATE

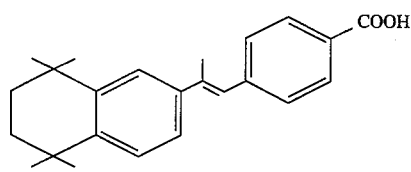

II

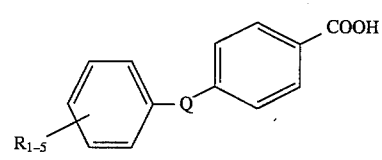

III

Other examples of retinoid compounds include arotinoid of formula II and retinobenzoic acid of formula III, in which Q equals —NHCO—, —CONH—, —COCH=CH—, —CH=CHCO—, —COCH$_2$—, etc.

See for example: Loeliger, P., Bollag, W., and Mayer, H., *Eur. J. Med. Chem.* 1980, 15, pp. 9–15; Kagechika, H. et al., *J. Med. Chem.*, 1988, 31, No. 11, pp. 2182–2192.

SUMMARY OF INVENTION

The present invention relates to a compound of formula I

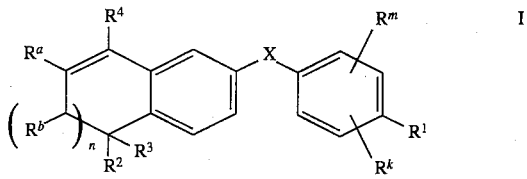

or a nontoxic pharmaceutically acceptable salt, physiologically hydrolyzable ester or solvate thereof, in which X is —O—CO—, —NH—CO—, —CS—NH—, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

$R^m$ and $R^k$ are independently hydrogen, halogen, C$_{1-6}$alkyl, hydroxy, C$_{1-6}$alkyloxy or nitro;

n is zero or one;

$R^4$ is —(CH$_2$)$_t$—Y, C$_{1-6}$alkyl, or C$_{3-6}$cycloalkyl;

$R^1$ is —CO$_2$Z, C$_{1-6}$alkyl, CH$_2$OH, —CONHR$^y$, or CHO;

$R^2$ and $R^3$ are independently hydrogen or C$_{1-6}$alkyl;

$R^a$ and $R^b$ are independently hydrogen or C$_{1-6}$alkyl; but when n is one, $R^a$ and $R^b$ together can form a radical of the formula

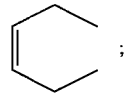

Y is naphthyl or phenyl, both radicals can be optionally substituted with one to three same or different C$_{1-6}$alkyl or halogen;

Z is hydrogen or C$_{1-6}$alkyl;

$R^5$, $R^6$ and $R^y$ are independently hydrogen or C$_{1-6}$alkyl; and t is zero to six.

Also provided by this invention are methods for preventing and/or treating tumors, arthritis, and non-malignant skin disorders comprising administering a compound of formula I to a mammal. Further provided is a pharmaceutical formulation (composition) comprising a compound of formula I in admixture with (a) pharmaceutically acceptable excipient(s).

BRIEF DESCRIPTION OF THE DRAWING

FIG. 1, 2 and 3 are the cytotoxicity dose response curves for lung line L2987.

FIG. 4 is a dose response curve for collagen-induced arthritis.

DETAILED DESCRIPTION OF THE INVENTION

Figure 1:
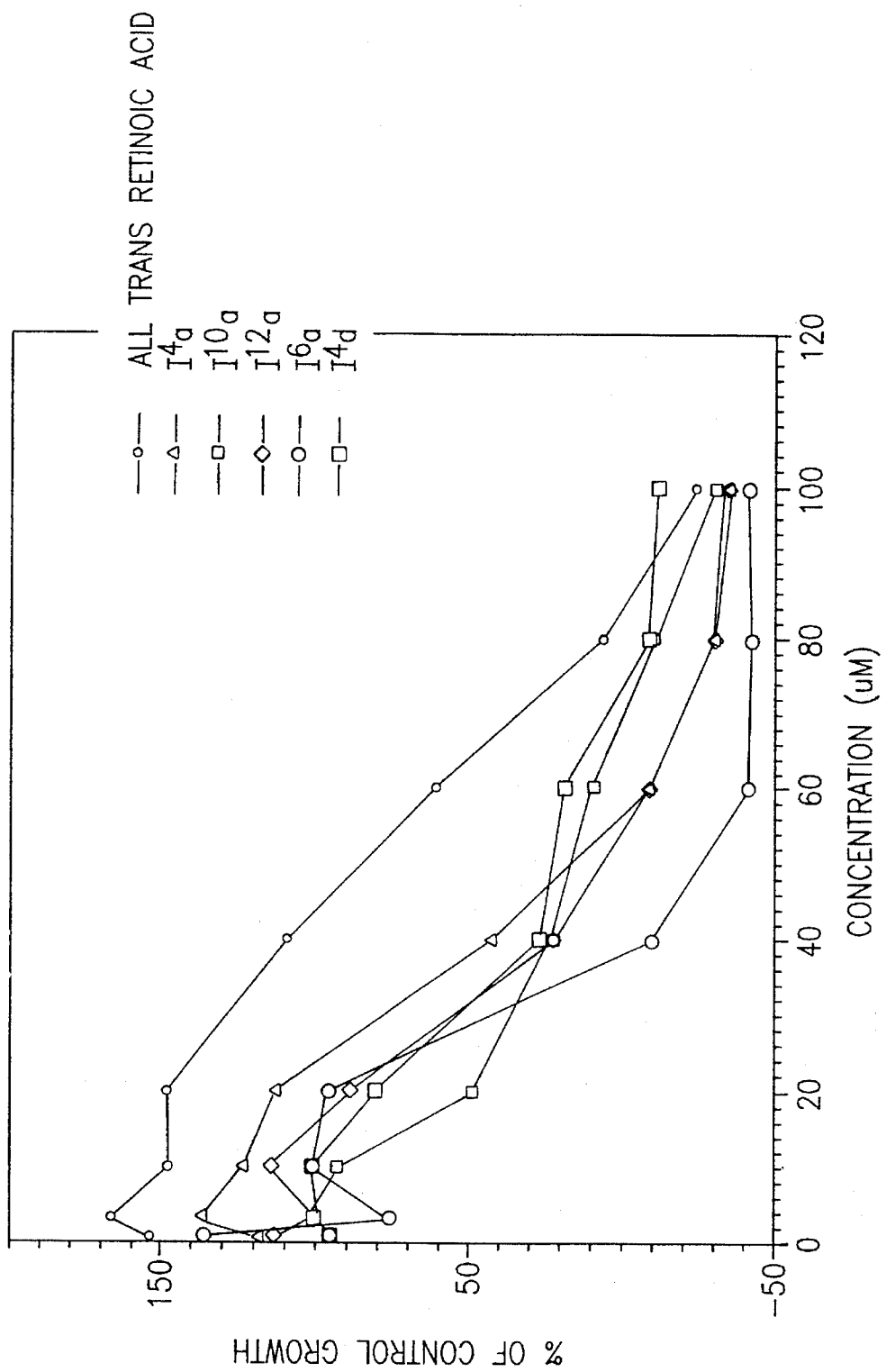

The present invention relates to a compound of formula I

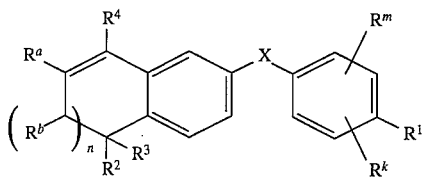

or a nontoxic pharmaceutically acceptable salt, physiologically hydrolyzable ester or solvate thereof, in which X is —O—CO—, —NH—CO—, —CS—NH—, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$_6$—;

R$^m$ and R$^k$ are independently hydrogen, halogen, C$_{1-6}$alkyl, hydroxy, C$_{1-6}$alkyloxy or nitro;

n is zero or one;

R$^4$ is —(CH$_2$)$_t$—Y, C$_{1-6}$alkyl, or C$_{3-6}$cycloalkyl;

R$^1$ is —CO$_2$Z, C$_{1-6}$alkyl, CH$_2$OH, —CONHR$^y$, or CHO;

R$^2$ and R$^3$ are independently hydrogen or C$_{1-6}$alkyl;

R$^a$ and R$^b$ are independently hydrogen or C$_{1-6}$alkyl; but when n is one, R$^a$ and R$^b$ together can form a radical of the formula

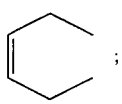

Y is naphthyl or phenyl, both radicals can be optionally substituted with one to three same or different C$_{1-6}$alkyl or halogen;

Z is hydrogen or C$_{1-6}$alkyl;

R$^5$, R$^6$ and R$^y$ are independently hydrogen or C$_{1-6}$alkyl; and t is zero to six.

In the instant application, the numbers in subscript after the symbol "C" define the number of carbon atoms a particular group can contain. For example, C$_{1-6}$alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; C$_{3-6}$cycloalkyl refers to cyclopropyl, cylcobutyl, cyclopentyl, or cyclohexyl; and halogen refers to fluorine, chlorine, bromine, or iodine. In the instant application all symbols once defined retain the same meaning until they are redefined.

Some compounds of formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like pharmaceutically acceptable amines.

When compounds of formula I contains carboxy groups, it can form physiologically hydrolyzable esters which serve as prodrugs by being hydrolyzed in the body to yield formula I compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include C$_{1-6}$alkyl, benzyl, 4-methoxybenzyl, indanyl, phthalidyl, methoxymethyl, C$_{1-6}$alkanoyloxy C$_{1-6}$alkyl, e.g. acetoxymethyl, pivaloyloxymethyl or propionyloxymethyl, C$_{1-6}$alkoxycarbonyloxyC$_{1-6}$alkyl, e.g. methoxycarbonyloxymethyl or ethoxycarbonyloxymethyl, glycyloxymethyl, phenylglycyloxymethyl, (5-methyl-2-oxo-1-3-dioxolen-4-yl)-methyl and other well-known physiologically hydrolyzable esters used, for example, in the penicillin and cephatosporin arts. Such esters are prepared by conventional techniques known in the art.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The synthesis of a compound of formula I can be accomplished by a wide variety of methods using conventional starting materials and processes. The synthetic descriptions and specific examples that follow are only intended for the purpose of illustration, and are not to be construed as limiting in any manner ways to make compounds of the present invention by other methods.

Typically a compound of formula I can be made by employing one of the processes or obvious variations thereof as depicted in Schemes I to XXII. All the steps in Schemes I to XXII are standard processes which can be easily practiced by anyone skilled in the art. The specific examples that are provided after the Schemes are intended to illustrate specific conditions which may be employed to carry out certain steps in the Schemes and are not to be construed as limiting the conditions in any way.

In the Schemes, R$^7$ is a conventional carboxy protecting group; it is preferably C$_{1-6}$alkyl or phenyl; even more preferably R$^7$ is phenyl, methyl, ethyl or t-butyl. When R$^7$ radical is t-butyl, it can be removed by trifluoroacetic acid.

In Step (a) of Scheme IV, a compound of formula XVIII is reacted with at least two equivalents of R$^5$Li in which R$^5$ is as previously defined, but preferably primary $C_{1-6}$alkyl. (When a compound of formula XIX in which $R^5$ is hydrogen is desired, it is preferable to employ a reducing agent which converts a carboxylic acid residue to an aldehyde on a compound of formula XVIII. Many such reducing agents are well known in the art.) Subsequently, an anion of p-[(diethoxyphosphoryl)methyl]benzene derivative of formula XX can be reacted with a compound XIX in a routine Horner-Wadsworth-Emmons reaction (see: *Org. React.*, 25, 73–253 (1977); Stec, *Acc. Chem. Res.*, 411–417 (1983)) to afford additional compounds of formula $I^5$. Subsequent hydrolysis yields a compound of formula $I^6$. Alternatively, a compound within the scope of formula $I^6$ can be made by a process of Scheme IVa. In Scheme V, $R^8$ is a phenolic hydroxy protecting group, such as t-butyldimethylsilyl which can be removed by tetrabutylammonium fluoride (TBAF).

Starting compounds of general formula XVIII in Schemes III, IV, VI, VII, XI, XII and XIII can be prepared by a wide variety of methods using conventional starting materials and processes. The syntheses of certain compounds within the scope of formula XVIII are illustrated in Schemes XIX to XXII.

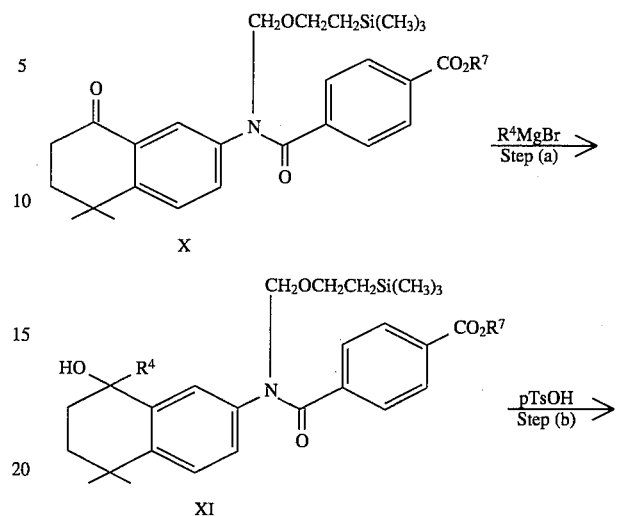

SCHEME II

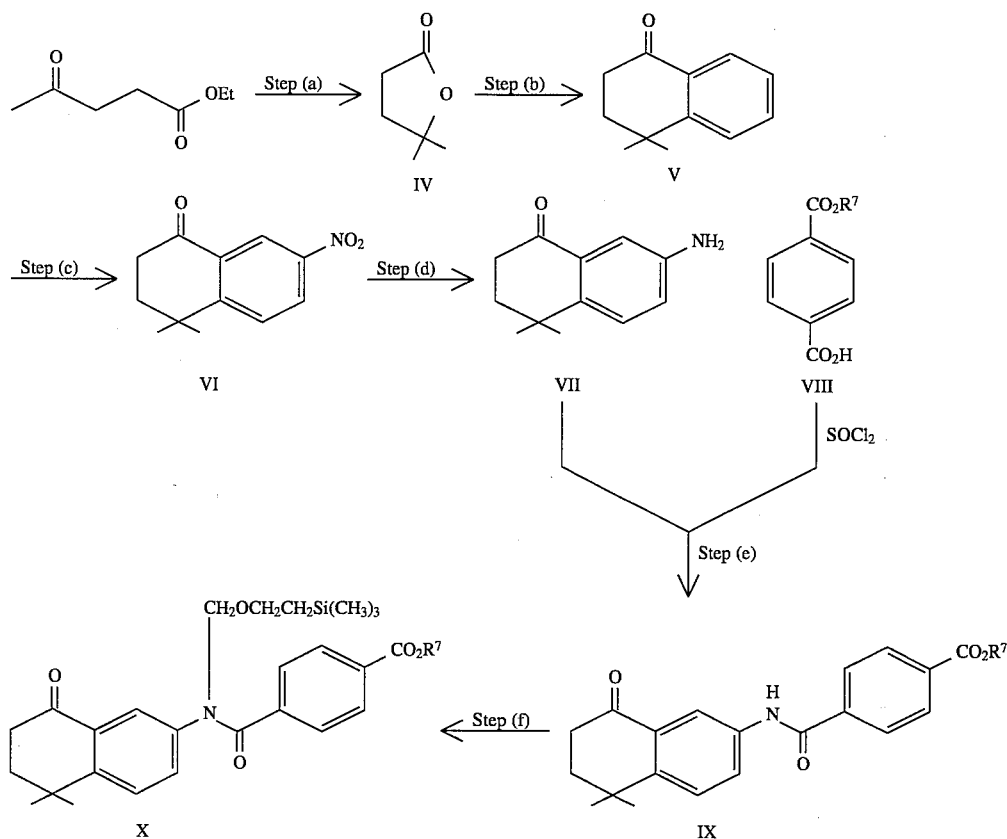

SCHEME I

SCHEME II -continued
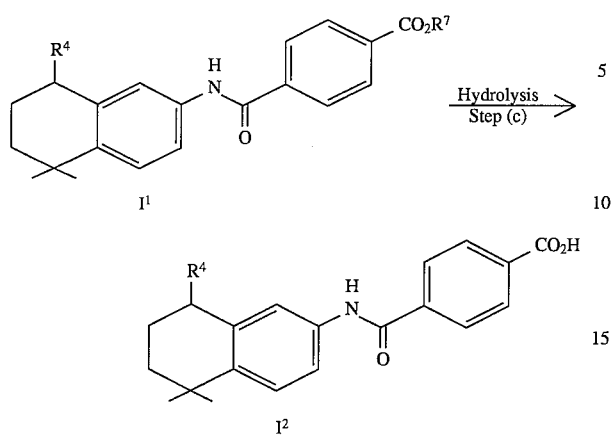
Scheme III
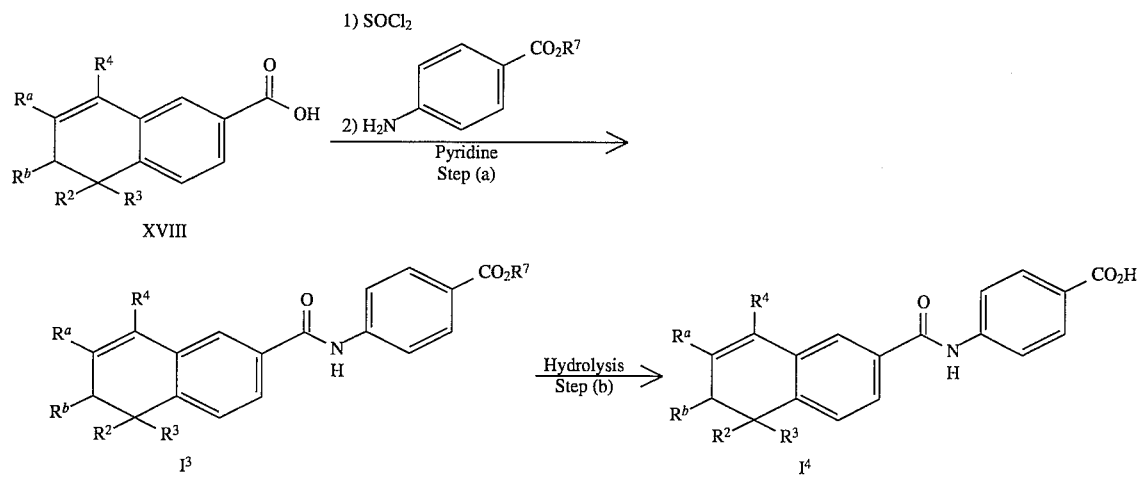
SCHEME IV
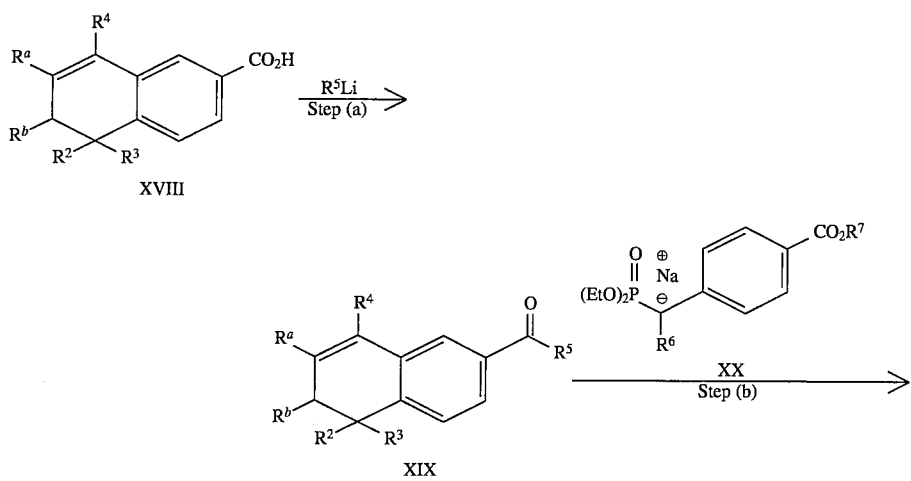

-continued
SCHEME IV
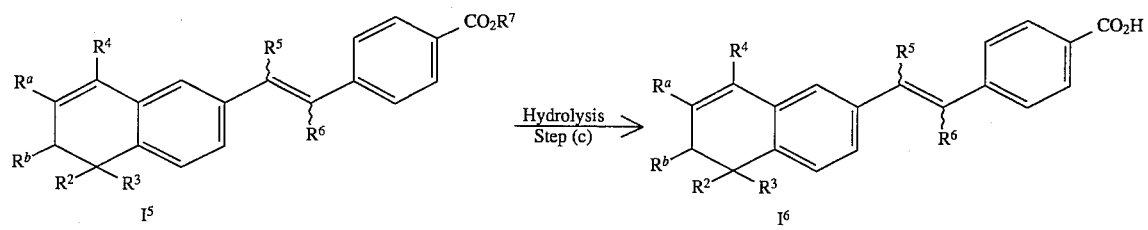
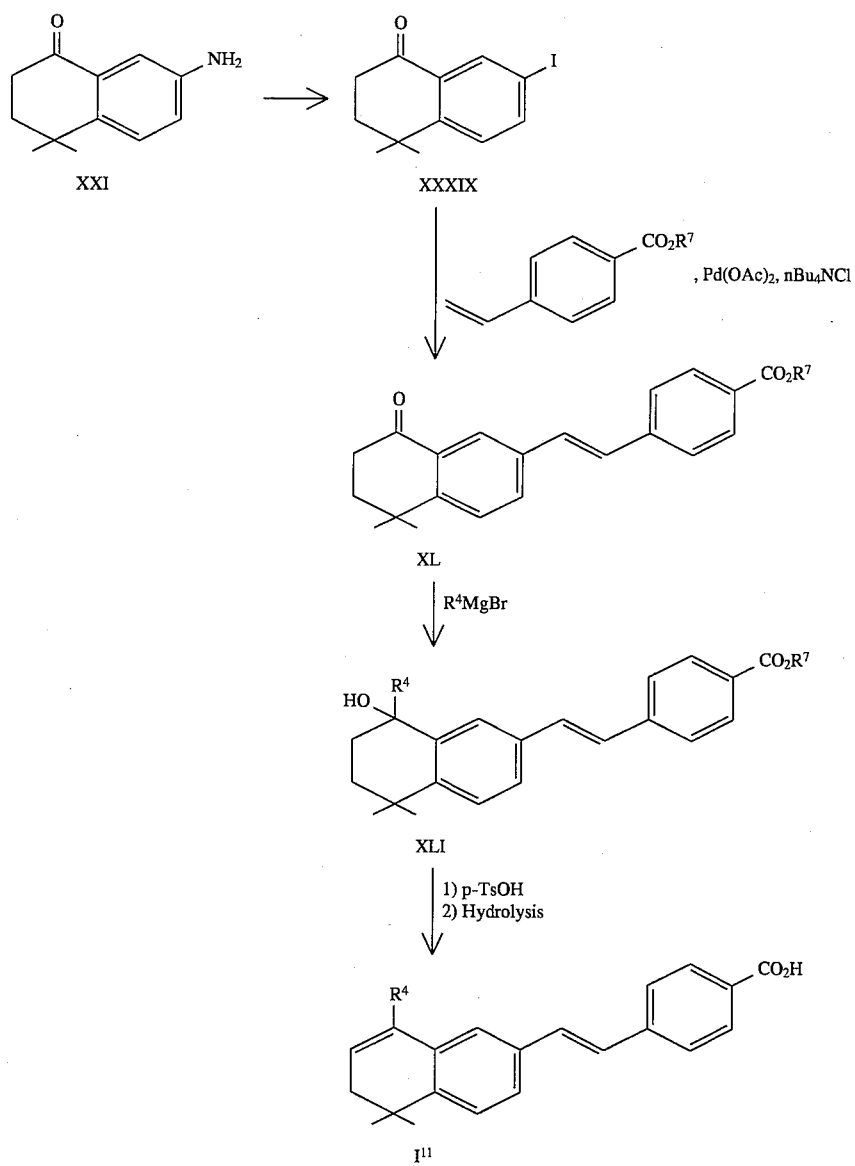

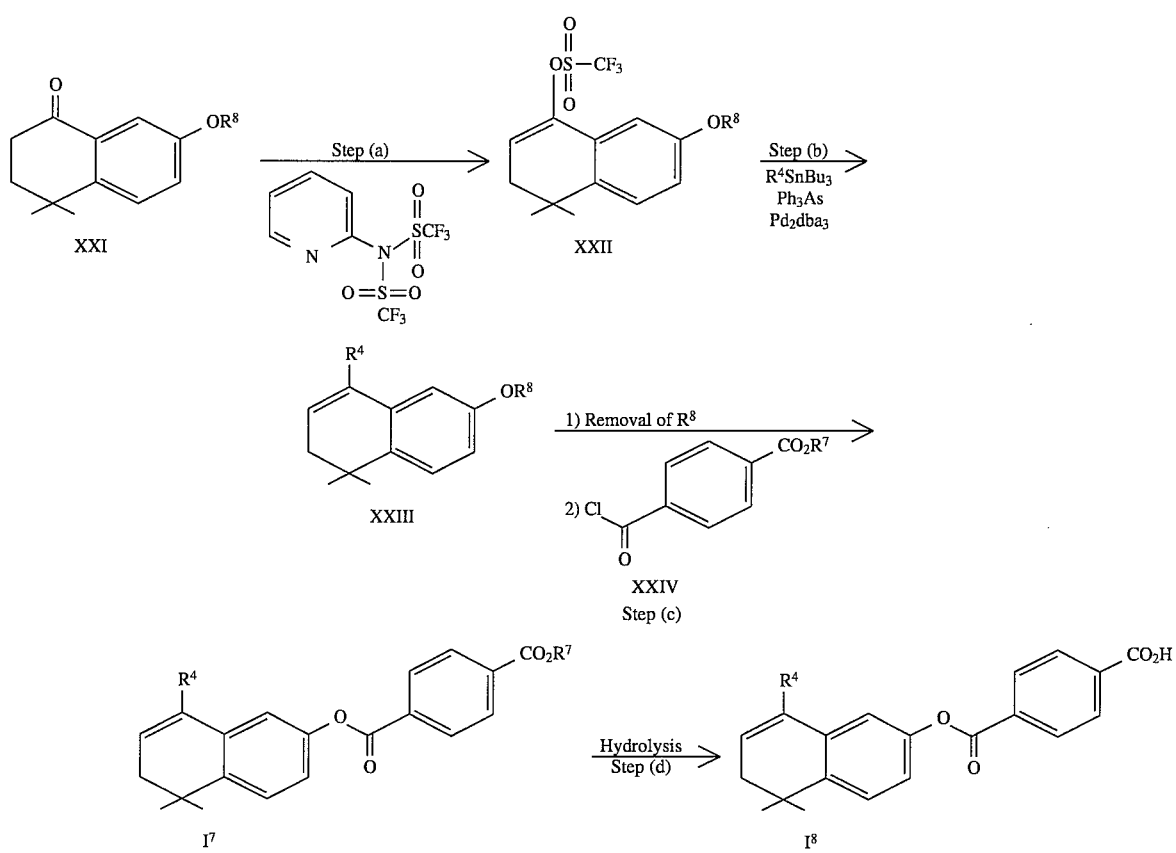
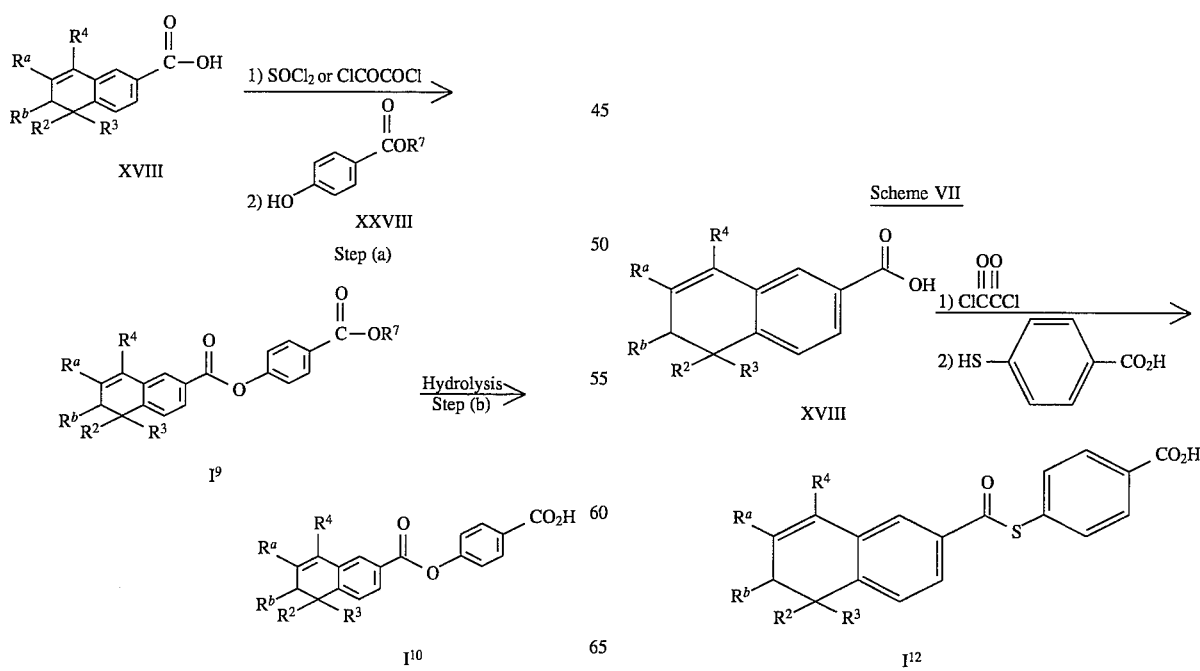

Scheme VIII
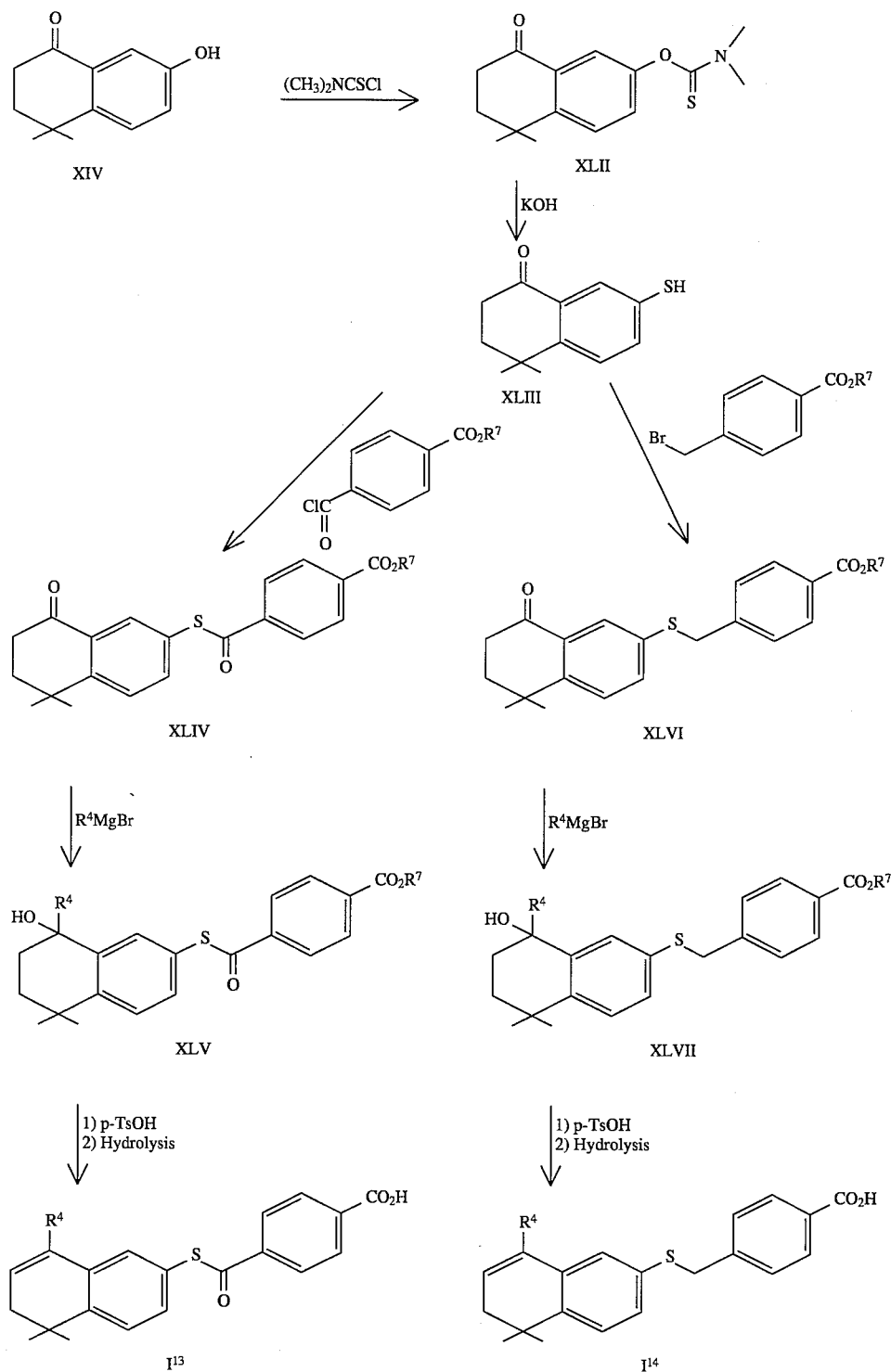

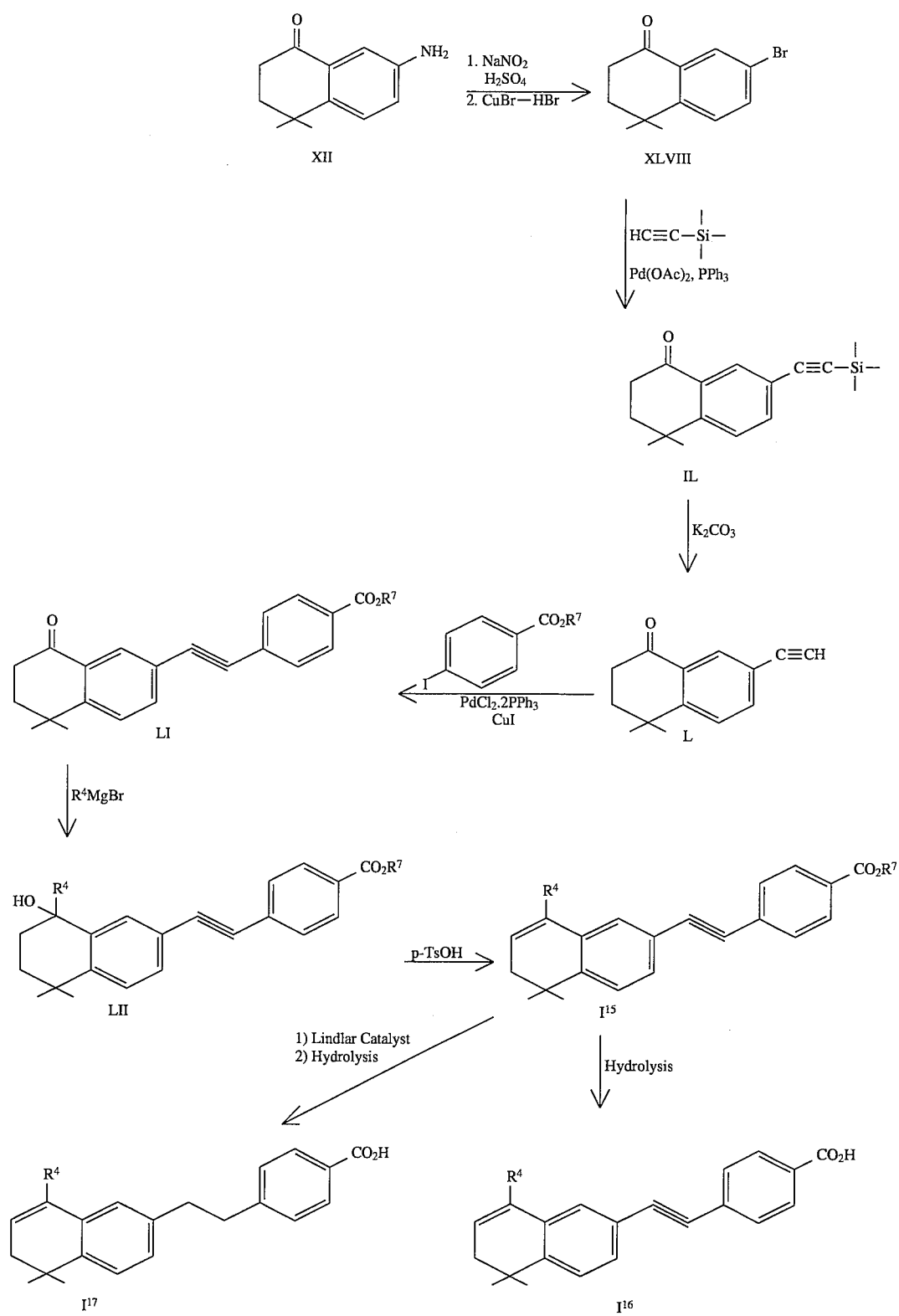

5,618,839
Scheme X
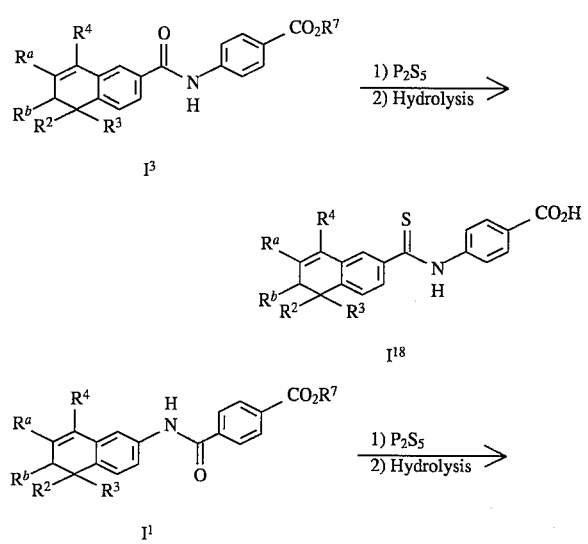
Scheme XI
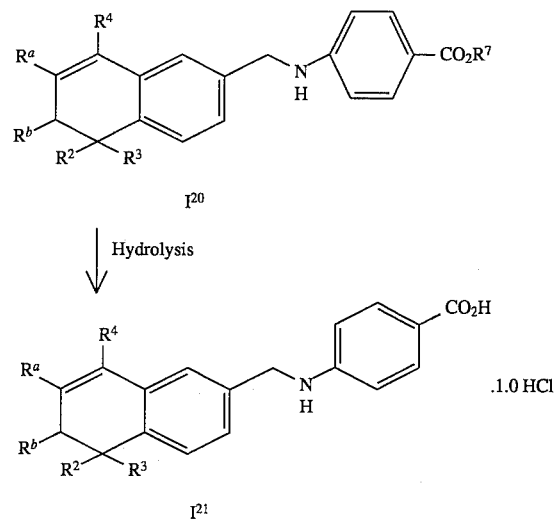
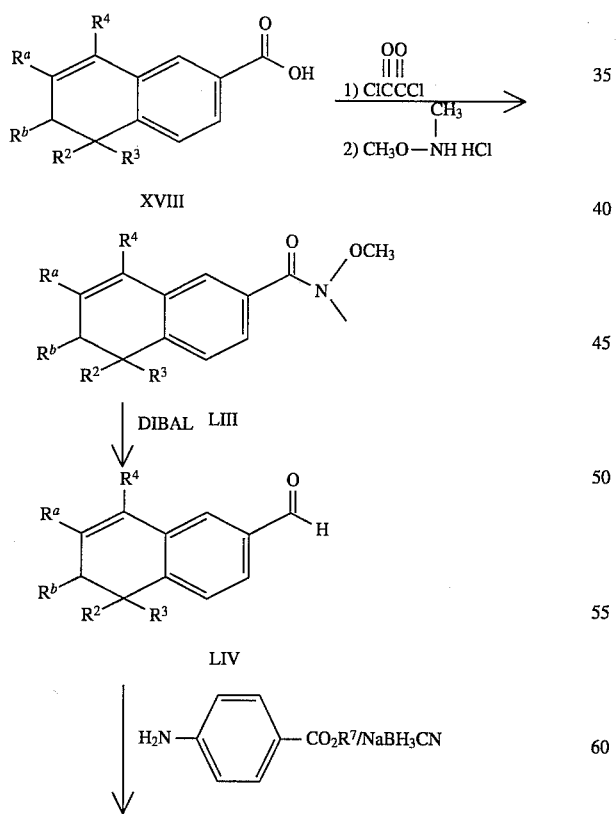

Scheme XII
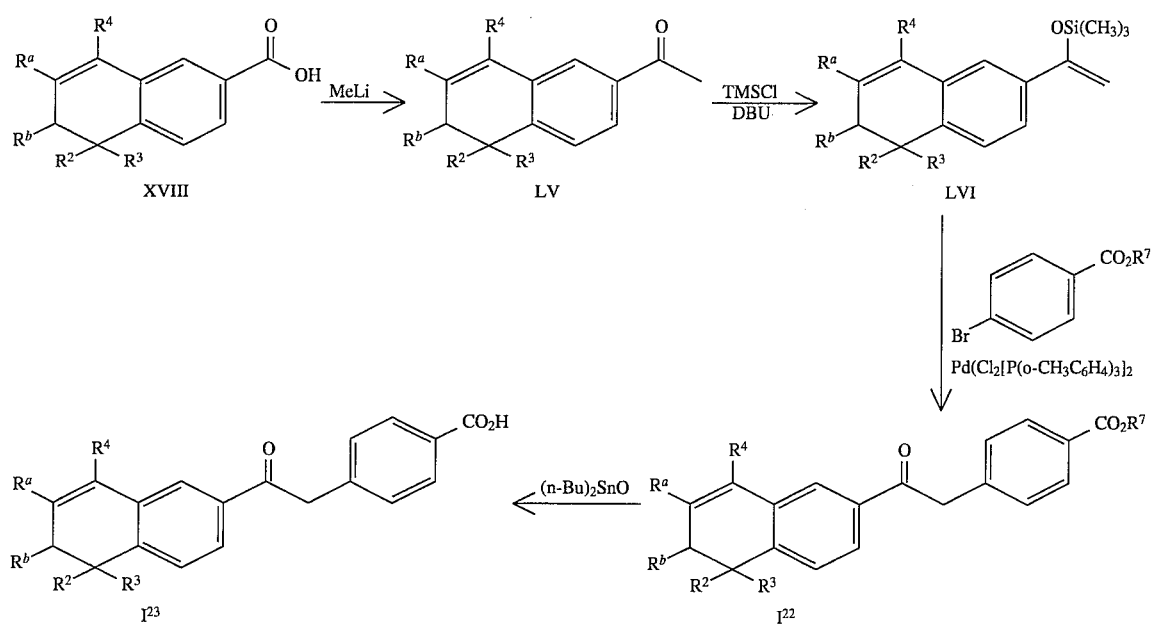
Scheme XIII
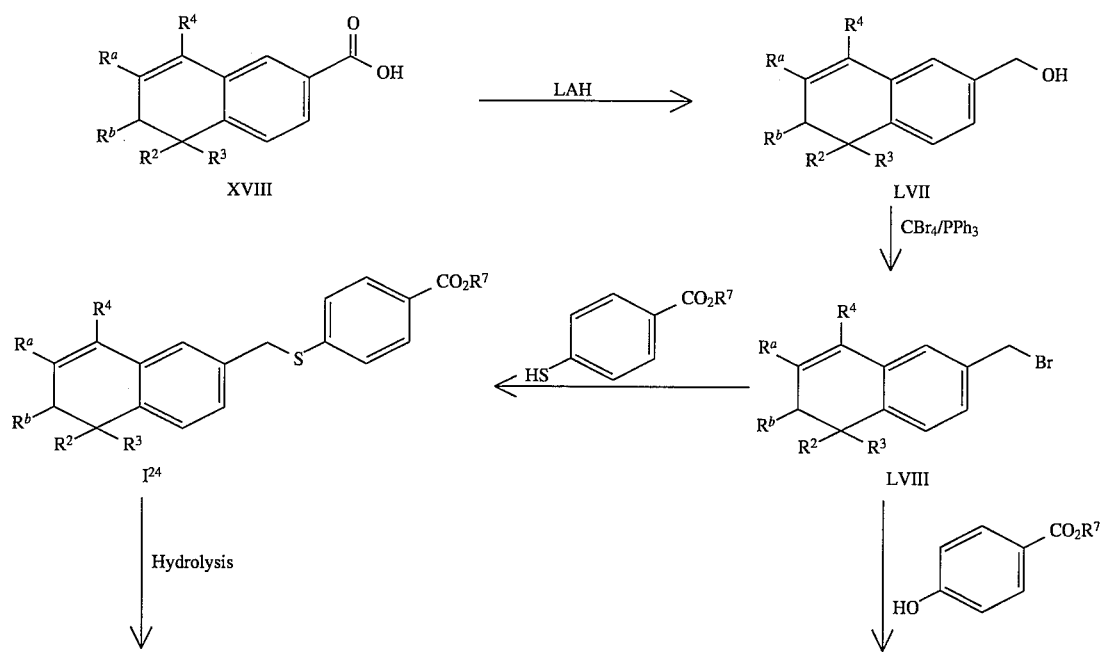

-continued
Scheme XIII
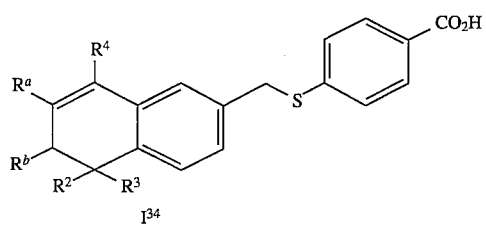
I³⁴
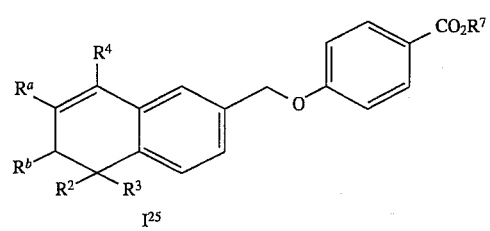
I²⁵
↓ Hydrolysis
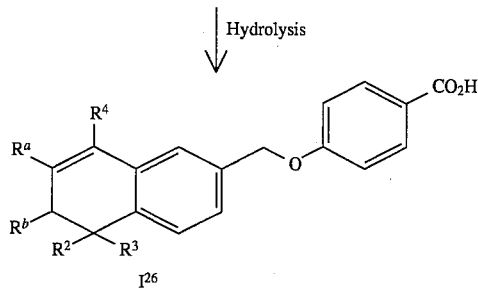
I²⁶
Scheme XIV
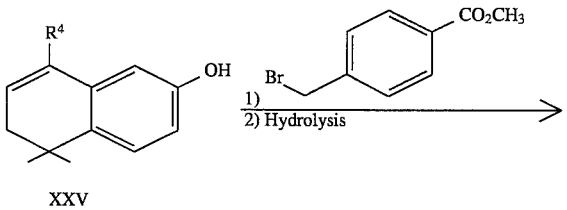
XXV
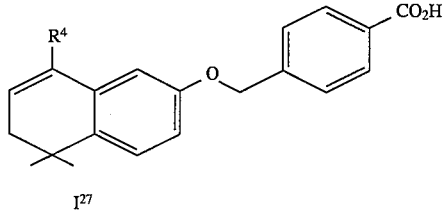
I²⁷
Scheme XV
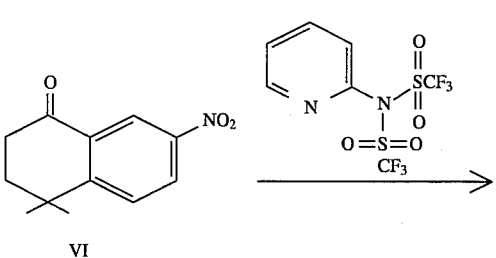
VI
-continued
Scheme XV
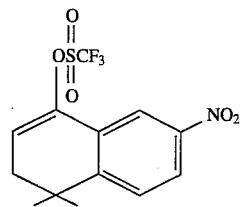
LXI
↓ R⁴SnBu₃, Pd₂dba₃, Ph₃A
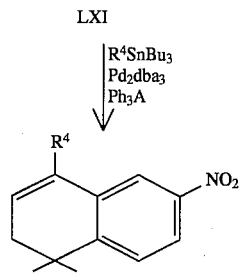
LXII
↓ FeCl₃/Fe
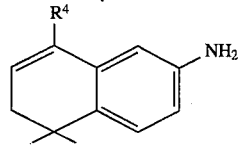
LXIII
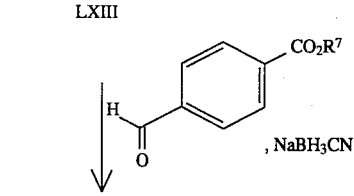, NaBH₃CN
↓

-continued
Scheme XV
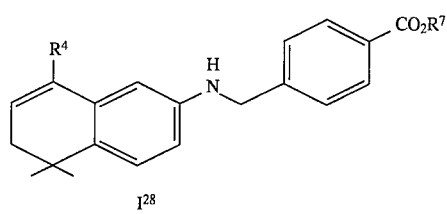
I²⁸
↓ Hydrolysis
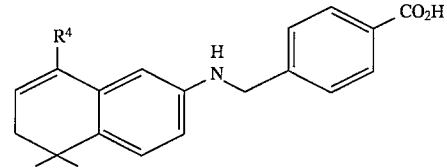
I²⁹ .HCl
SCHEME XVI
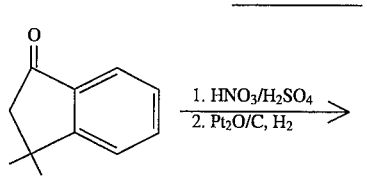
LXIV
1. HNO₃/H₂SO₄
2. Pt₂O/C, H₂
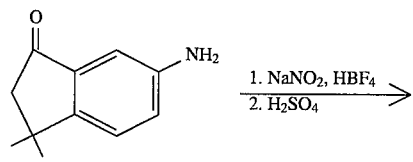
LXV
1. NaNO₂, HBF₄
2. H₂SO₄
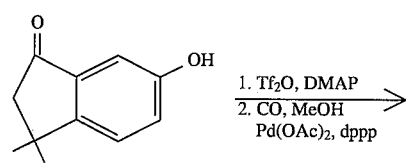
LXVI
1. Tf₂O, DMAP
2. CO, MeOH
   Pd(OAc)₂, dppp
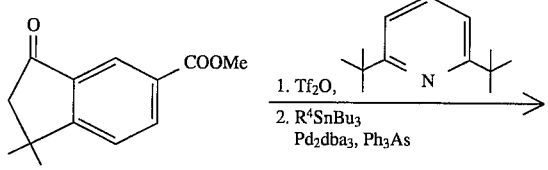
LXVII
1. Tf₂O,
2. R⁴SnBu₃
   Pd₂dba₃, Ph₃As
-continued
SCHEME XVI
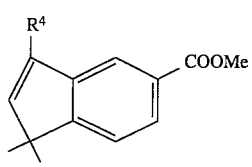
LXVIII
1. NaOH
2. (COCl)₂
3. 4-NH₂—Ph—COOR⁷
   Pyridine
4. Hydrolysis
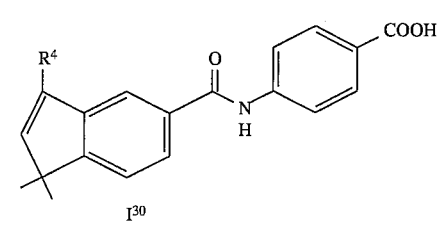
I³⁰
SCHEME XVII
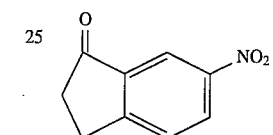
LXIX
1. Tf₂O
2. R⁴SnBu₃
   Pd₂dba₃, Ph₃As
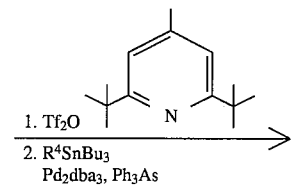
LXX
Fe—FeCl₃
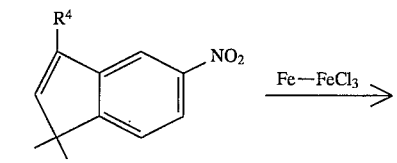
LXXI
1. p-ClOCPhCOOR⁷
   pyridine
2. Hydrolysis
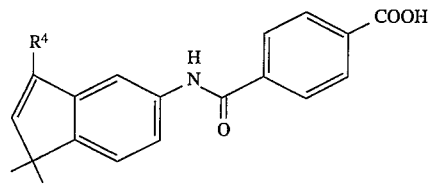
I³¹

SCHEME XVIII
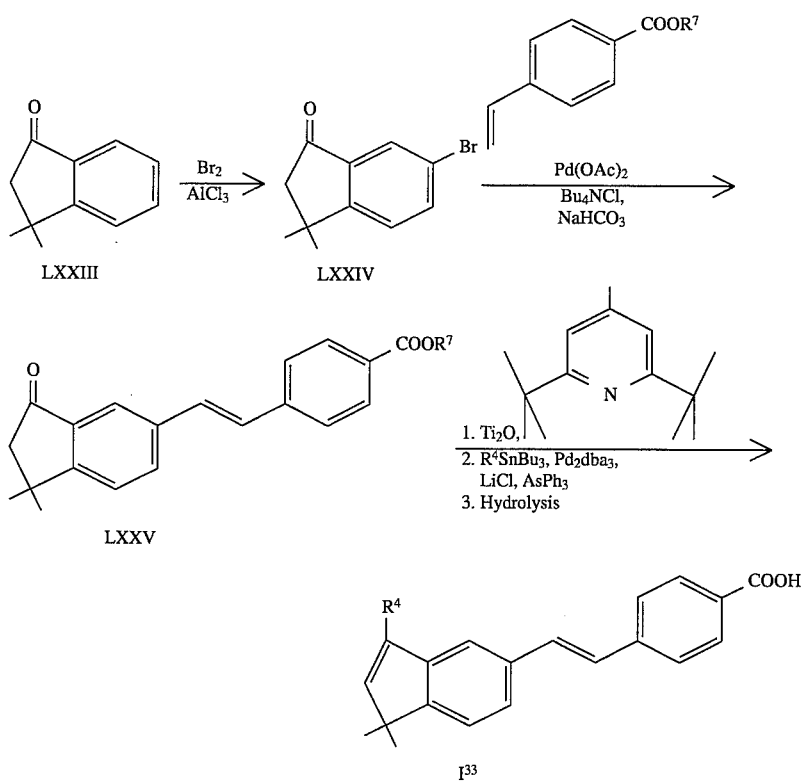
SCHEME XIX
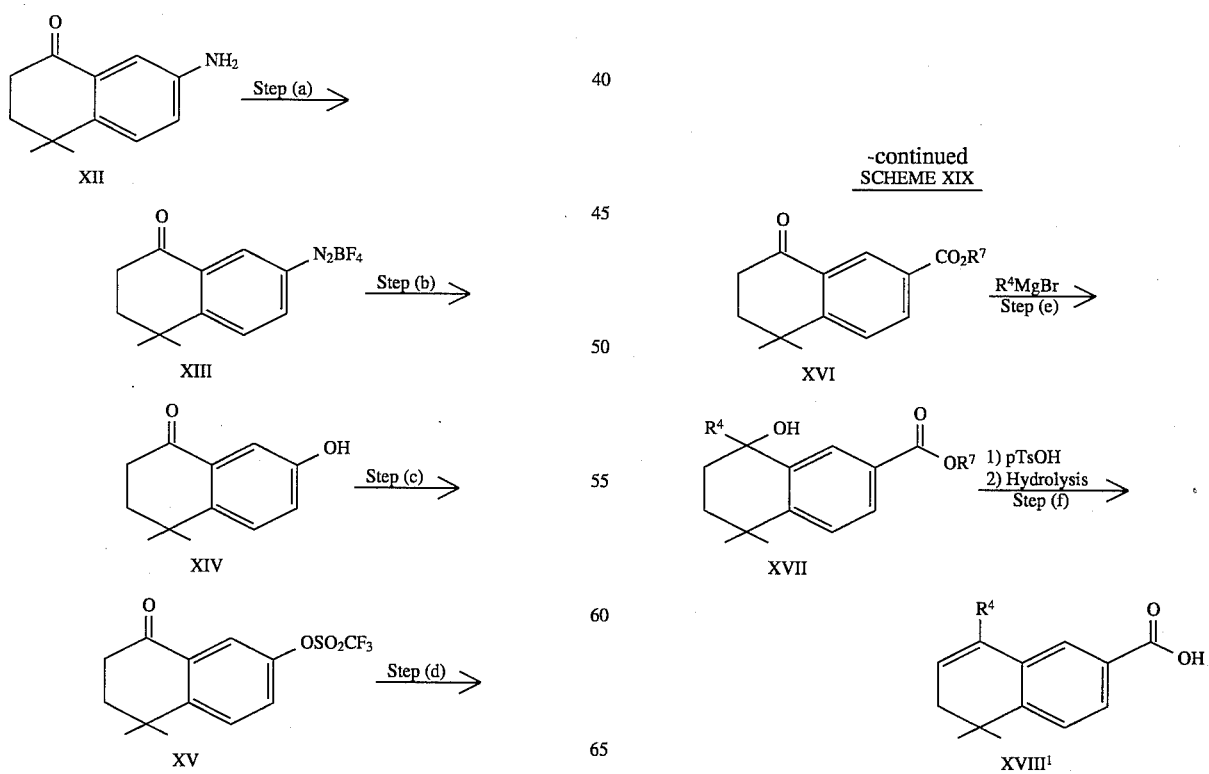

SCHEME XX

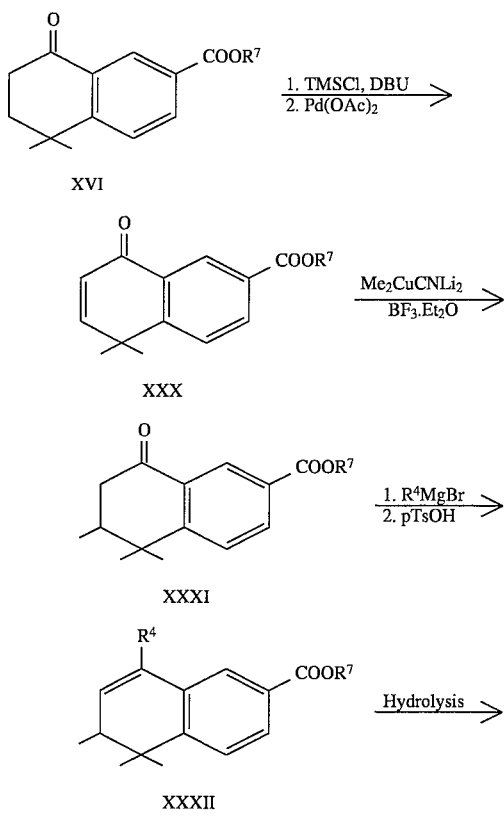

SCHEME XXI

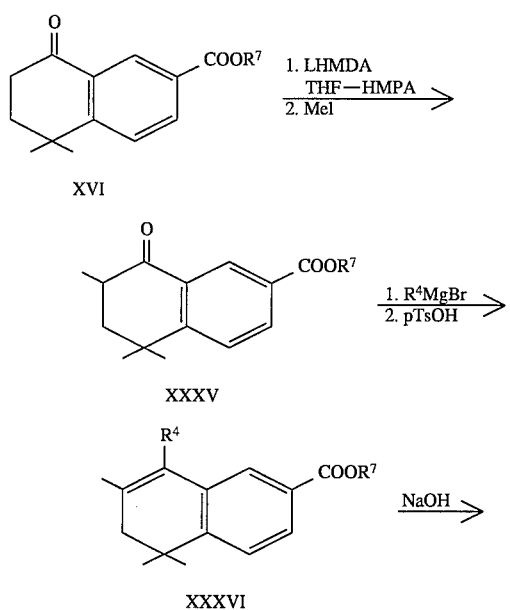

SCHEME XXI -continued

SCHEME XXII

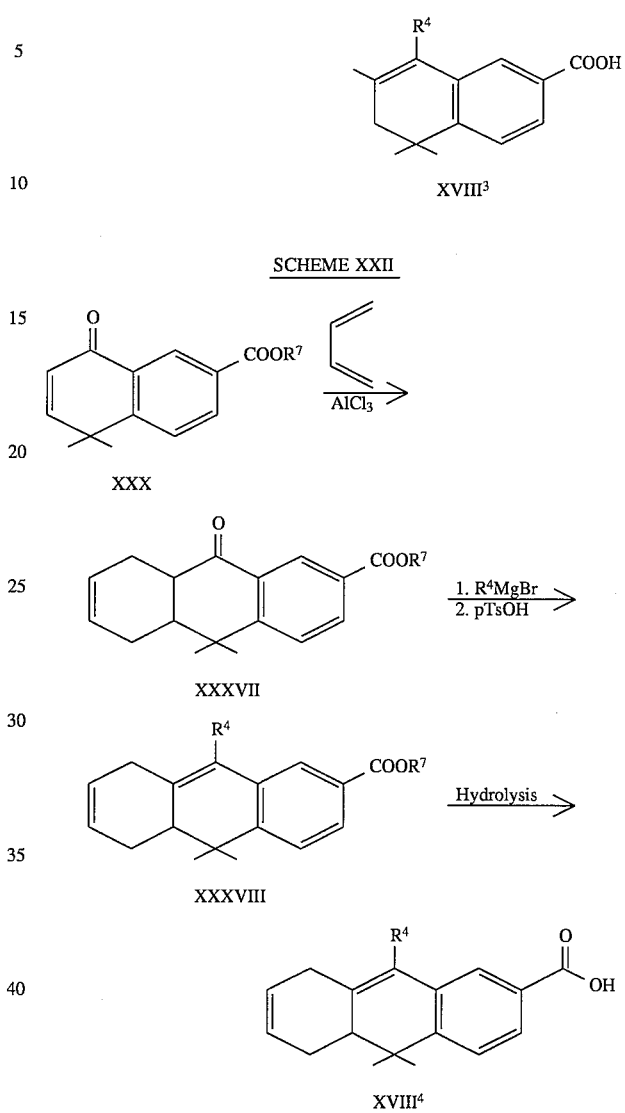

DESCRIPTION OF SPECIFIC EMBODIMENTS

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multipier (m), doublet (d), quartet (q), triplet (t), doublet of doublet (dd), doublet of triplet (dr), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers (cm$^{-1}$) having functional group identification value.

Celite is a registered trademark of the Johns-Manville Products Corporation for diatomaceous earth.

The abbreviations used herein are conventional abbreviations widely employed in the art. Some of which are:

MS: mass spectrometry
HRMS: high resolution mass spectrometry
Ar: aryl
DCI: desorption (or direct) chemical ionization
Hex: hexane(s)
tBu: tertiarybutyl
h: hour(s)
min: minute(s)
Ph: phenyl
Y: yield
THF: tetrahydrofuran
$Tf_2O$: triflic anhydride (trifluoromethanesulfonic anhydride)
SEMCl2-(trimethylsilyl)ethoxyethyl chloride

EXAMPLE 1

5,5-Dimethyl-dihydrofuran-2-one (IV)

A solution of ethyl levulinate (50.0 g, 0.345 mole) in anhydrous ethyl ether (200 mL) and anhydrous benzene (200 mL) was treated with methylmagnesium bromide (3.0M solution in diethyl ether, 121.0 mL, 0.365 mole) dropwise at 0° C. over 30 minutes. At this time the ether was removed by slow distillation and the resulting benzene solution was heated at reflux for 2 hours. An ice cold solution of 20% phosphoric acid (500 mL) and ethyl acetate (500 mL) were then added at 0° C. The organic phase was then separated, washed with brine (1×300 mL), dried over anhydrous magnesium sulfate, filtered and concentrated in vacuo. The resulting crude oil was purified by distillation (b.p., 43° C., 0.35 mm Hg) yielding 26.0 g of the title furan-2-one (Y: 66%); $^1$H-NMR (CDCl$_3$): δ2.62 (t, J=8.5 Hz, 2H), 2.05 (t, J=8.5 Hz, 2H), 1.42 (s, 6H).

EXAMPLE 2

4,4-Dimethyl-1-tetralone (V)

To a solution of anhydrous aluminum chloride (0.446 mmol, 59.36 g) in anhydrous benzene (94.0 mL) at 5° C. was added over a period of 45 minutes 5,5-dimethyldihydrofuran-2-one (0.149 mole, 17.0 g). The reaction mixture was then slowly warmed to 90°–100° C. After 3 hours, the mixture was quenched with ice water, 1N HCl and ethyl acetate at 0° C. The organic phase was then separated and concentrated in vacuo. The residue was chromatographed (eluted with 3% ethyl acetate in hexane) on silica gel to give 18.70 g (Y: 72%) of 4,4-dimethyl-1-tetralone; $^1$H-NMR (CDCl$_1$): δ8.01 (m, 1H) 7.50 (m, 1H), 7.41 (m, 1H), 7.28 (m, 1H), 2.72 (t, J=7.0 Hz, 2H), 2.02 (t, J=7.0 Hz, 2H), 1.39 (s, 6H); MS (DCI) m/e: 174 (MH$^+$)

Anal. calcd. for $C_{12}H_{14}O_1$: C, 81.77; H, 9.14. Found: C, 81.70; H, 9.12.

EXAMPLE 3

4,4-Dimethyl-7-nitro-1-tetralone (VI)

The title compound was prepared by Procedure of Heck & Winstein, J. Org. Chem., Vol. 37, No. 6, 1972, p. 825; $^1$H-NMR (CDCl$_3$): δ8.84 (d, J=2.5 Hz, 1H), 8.36 (dd, J=7.0 Hz, 2.5 Hz, 1H), 7.62 (d, J=7.0 Hz, 2H), 2.80 (t, J=7.0 Hz, 3H), 2.08 (t, J=7.0 Hz, 3H), 1.45 (s, 6H); MS (DCI) m/e: 220 (MH$^+$).

EXAMPLE 4

4,4,Dimethyl-7-amino-1-tetralone (VII)

The title compound was prepared by procedure of Heck & Winstein, J. Org. Chem., Vol. 37, No. 6, 1972, p. 825; $^1$H-NMR (CDCl$_3$): δ7.28 (d, J=8.5 Hz, 1H), 7.21 (d, J=2.5 Hz, 1H), 6.86 (dd, J=8.5, 2.5 Hz, 1H), 3.73 (bs, 2H), 2.70 (t, J=7.0 Hz, 2H), 1.97 (t, J=7.0 Hz, 2H), 1.37 (s, 6H); MS (DCI) m/e: 190 (MH$^+$).

EXAMPLE 5

4-[[(5,6,7,8-Tetrahydro-5,5-dimethyl-8-oxo-2-naphthalenyl)amino]carbonyl]benzoic acid methyl ester (IXa)

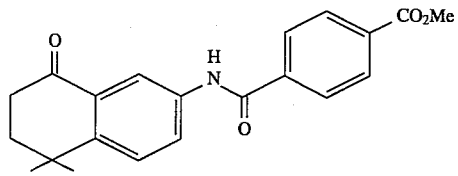

A solution of monomethyl terephthalate (VIIIa) (2.86 g, 15.89 mmoles) in thionylchloride (50 mL) with 2 drops of N,N-dimethylformamide was allowed to stir at room temperature. The mixture became homogeneous within 30 minutes and was then concentrated in vacuo. The residue was then taken up in 30 mL of anhydrous pyridine and treated with 4,4-dimethyl-7-amino-1-tetralone (3.00 g, 15.9 mmoles). After 16 hours at room temperature 1N HCl was added to the mixture. It was extracted with ethyl acetate, washed with 1N HCl (4×200 mL) and washed with saturated sodium bicarbonate (2×200 mL). The organic phase was then separated, dried over magnesium sulfate, and concentrated in vacuo to give 5.07 g (Y: 91% ) of the title compound; $^1$H-NMR (CDCl$_3$): δ8.27 (dd, J=8.7, 2.5 Hz, 1H), 8.19 (bs, 1H), 8.14 (d, J=8.4 Hz, 2H), 7.95 (d, J=8.4 Hz, 2H), 7.91 (d, J=2.5 Hz, 1H), 7.46 (d, J=8.7 Hz, 1H), 3.94 (s, 3H), 2.70 (t, J=7.0 Hz, 3H), 2.00 (t, J=7.0 Hz, 3H), 1.38 (s, 6H); MS (DCI) m/e: 352 (MH$^+$).

EXAMPLE 6

N-[2-(Trimethylsilyl)ethoxymethyl]-4-[[(5,6,7,8-tetrahydro-5,5-dimethyl-8-oxo-2-naphthalenylamino]carbonyl]benzoic acid, methyl ester (Xa)

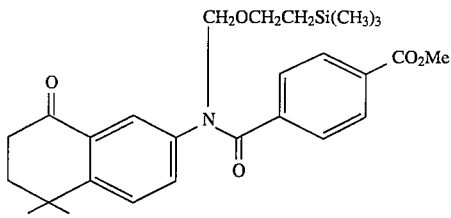

A solution of 4-[[(5,6,7,8-tetrahydro-5,5-dimethyl-8-oxo-2-naphthalenyl)amino]carbonyl]benzoic acid, methyl ester (5.07 g, 14.4 mmol) in anhydrous N,N-dimethylformamide (75 mL) at 0° C. was treated with 80% sodium hydride (477 mg, 15.9 mmoles). When hydrogen evolution ceased 2-(trimethylsilyl)ethoxymethyl chloride (3.61 g, 21.7 mmol) was slowly added. After 16 h at room temperature, the mixture was diluted with a 10% sodium bicarbonate solution (100 mL) and extracted with diethyl ether. The organic phase was concentrated in vacuo and the residue chromatographed (eluted with 20% ethyl acetate in hexane) over silica to give 4.24 g (Y: 61%) of the title product; MS (DCI) m/e: 482 (MH$^+$); $^1$H-NMR (CDCl$_3$): δ7.90 (d, J=7.5 Hz, 2H), 7.82 (s, 1H), 7.45 (d, J=7.5 Hz, 2H), 7.25 (m, 2H), 5.22 (bs, 2H), 3.93 (s, 3H), 3.67 (t, J=8.0 Hz, 2H), 2.69 (t, J=7.0 Hz, 2H), 1.98 (t, J=7.0 Hz, 2H), 1.33 (s, 6H), 0.96 (t, J=8.0 Hz, 2H), 0.00 (s, 9H).

EXAMPLE 7

N-[2-(Trimethylsilyl)ethoxymethyl]-4-[[(5,6,7,8-tetrahydro-5,5-dimethyl-8-ethyl-8-hydroxy-2-naphthalenyl)amino]carbonyl]benzoic acid methyl ester (XIa)

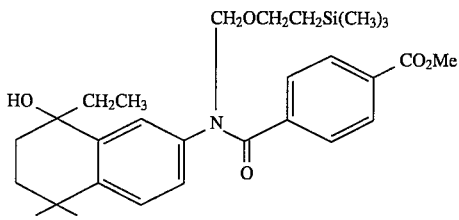

To a solution of compound Xa (1.07 g, 2.22 mmol) in anhydrous tetrahydrofuran (15 mL) at −78° C. was added ethyl magnesium bromide (3.0M solution in diethyl ether, 1.05 mL, 3.15 mmol). After 10 minutes, the reaction mixture was allowed to warm to room temperature. After 3 hours at room temperature, the reaction mixture was diluted with ethyl acetate (100 mL) and washed with water (100 mL). The organic phase was evaporated and the residue chromatographed on silica gel (eluted with 20% ethyl acetate in hexane) to give 103 mg (Y: 9%) of the title product; $^1$H-NMR (CDCl$_3$): δ7.87 (m, 2H), 7.40 (m, 2H), 7.20 (m, 1H), 7.10 (m, 2H), 5.40 (m, 1H), 5.20 (m, 1H), 3.90 (s, 3H), 3.75 (m, 2H), 2.00 (m, 1H), 1.78–1.42 (m, 5H), 1.27 (s, 3H), 1.25 (s, 3H), 1.05 (t, J=8.0 Hz, 3H), 0.95 (m, 2H), 0.00 (s, 9H); MS (DCI) m/e: 494 (MH$^+$-H$_2$O).

EXAMPLE 8

4-[[(5,6-Dihydro-5,5-dimethyl-8-ethyl-2-napthalenyl)amino]carbonyl]benzoic acid, methyl ester (I$^1$a)

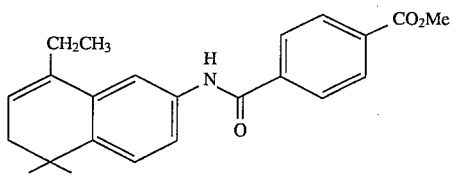

To a solution of compound XIa (169 mg, 0.33 mmol) in toluene (10 mL) was added p-toluenesulfonic acid (pTsOH) monohydrate (a few crystals). After heating at 75° C. for 5 minutes, the reaction mixture was concentrated in vacuo and the residue chromatographed on silica gel (eluted with 15% ethyl acetate in hexane) to give 34 mg (Y: 28%) of the title compound; $^1$H-NMR (CDCl$_3$): δ8.20 (d, J=8.5 Hz, 2H), 7.95 (d, J=8.5 Hz, 2H), 7.50 (m, 2H), 7.35 (d, J=7.0 Hz, 1H), 5.80 (t, J=4.4 Hz, 1H), 3.95 (s, 3H), 2.50 (q, J=7.0 Hz, 2H), 2.20 (d, J=4.4 Hz, 2H), 1.25 (s, 6H), 1.10 (t, J=7.0 Hz, 3H).

EXAMPLE 9

4-[[(5,6-Dihydro-5,5-dimethyl-8-ethyl-2-naphthalenyl)amino]carbonyl]benzoic acid (I$^2$a)

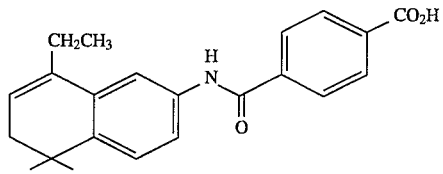

To a stirred solution of compound I$^1$a (34 mg, 0.094 mmol) in an ethanol and tetrahydrofuran solution (5 mL, 1:1) was added 10N NaOH (1.0 mmol, 0.1 mL) at room temperature. After 72 hours an excess of 1N HCl (20 mL) was added. The precipitate was collected by vacuum filtration, washed with 1N HCl, water, and air dried to give 21 mg (Y: 64%) of the title compound; $^1$H-NMR (DMSO-d$_6$): δ10.32 (s, 1H), 8.05 (s, 4H), 7.67 (m, 2H), 7.27 (d, J=9.0 Hz, 1H), 5.78 (t, J=4.4 Hz, 1H), 2.41 (q, J=7.0 Hz, 2H), 2.13 (d, J=4.4 Hz, 2H), 1.18 (s, 6H), 1.12 (t, J=7.0 Hz, 3H); $^{13}$C-NMR (DMSO-d$_6$): 166.79, 164.63, 164.55, 140.30, 138.64, 136.99, 136.75, 133.50, 133.26, 129.26, 127.84, 123.94, 122.48, 119.13, 115.43, 38.06, 32.86, 28.23, 25.13, 13.22; MS (DCI) m/e: 350 (MH$^+$); IR (KBr): 2962, 1700, 1652, 1532.

Anal. calcd. for C$_{22}$H$_{23}$O$_3$N$_1$•0.74 H$_2$O: C, 72.80; H, 6.80; N, 3.86. Found: C, 72.49; H, 6.56; N, 3.74.

EXAMPLE 10

N-[2-(Trimethylsilyl)ethoxymethyl]-4-[[(5,6,7,8-tetrahydro-5,5,8-trimethyl-8-hydroxy-2-naphthalenyl)amino]carbonyl]benzoic acid, methyl ester (XIb)

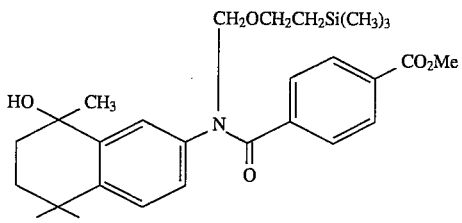

To a solution of compound Xa (438 mg, 0.91 mmol) in anhydrous tetrahydrofuran (10 mL) at −78° C. was added methylmagnesium bromide (3.0M solution in diethyl ether, 0.43 mL, 1.30 mmol). After 10 minutes at −78° C. the reaction mixture was allowed to warm to room temperature. After 3 hours at room temperature, the reaction mixture was diluted with ethyl acetate (100 mL) and washed with water (100 mL). The organic phase was evaporated and the residue chromatographed on silica gel (eluted with 20% ethyl acetate in hexane) to give 90 mg (Y: 20%) of the title compound; $^1$H-NMR (CDCl$_3$): δ7.90 (m, 2H), 7.40 (m, 2H), 7.25 (m, 2H), 7.10 (m, 1H), 5.25 (m, 2H), 3.90 (s, 3H), 3.70 (m, 2H), 1.90 (t, J=7.0 Hz, 2H), 1.75 (t, J=7.0 Hz, 2H), 1.30 (s, 3H), 1.29 (s, 3H), 1.27 (s, 3H), 1.00 (t, J=8.0 Hz, 3H), 0.00 (s, 9H); MS (DCI) m/e: 480 (MH$^+$-H$_2$O).

EXAMPLE 11

4-[[(5,6-Dihydro-5,5,8-trimethyl-2-naphthalenyl)amino]carbonyl]benzoic acid, methyl ester (I$^1$b)

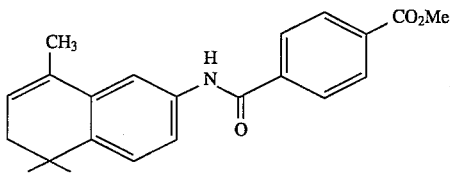

To a solution of compound XIb (218 mg, 0.44 mmol) in toluene (10 mL) was added p-toluene sulfonic acid monohydrate (70 mg, 0.37 mmol). After heating at 75° C. for 15 minutes, the reaction mixture was concentrated in vacuo and the residue chromatographed on silica gel (eluted with 20% ethyl acetate in hexane) to give 28 mg (Y: 18%) of the title product; $^1$H-NMR (CDCl$_3$): δ8.20 (d, J=9.0 Hz, 2H), 7.95 (d, J=9.0 Hz, 2H), 7.90 (bs, 1H), 7.50 (m, 2H), 7.35 (d, J=8.5 Hz, 1H), 5.80 (m, 1H), 3.95 (s, 3H), 2.25 (m, 2H), 2.10 (d, J=1.4 Hz, 3H), 1.30 (s, 6H); MS (DCI) m/e: 350 (MH$^+$).

EXAMPLE 12

4-[[(5,6-Dihydro-5,5,8-trimethyl-2-namhthalenyl)amino]carbonyl]benzoic acid (I$^2$b)

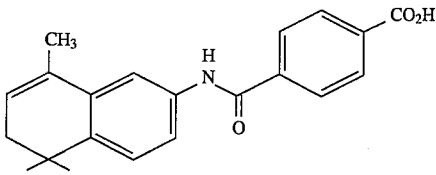

To a stirred solution of compound I$^1$b (0.097 mmol, 34 mg) in a 1:1 ethanol and tetrahydrofuran solution (5 mL) was added 10N NaOH (1.0 mmol, 0.1 mL) at room temperature. After 72 hours, an excess of 1N HCl (20 mL) was added. The precipitate was collected by vacuum filtration, washed with 1N HCl, water, and dried to give 14 mg (Y: 43%) of the title compound; (DMSO-d$_6$): δ10.32 (s, 1H), 8.04 (s, 4H), 7.66 (dd, J=8.3, 2.1 Hz, 1H), 7.62 (d, J=2.1 Hz, 1H), 7.27 (d, J=8.3 Hz, 1H), 5.80 (m, 1H), 2.14 (m, 2H), 2.01 (d, J=1.4 Hz, 3H), 1.18 (s, 6H); $^{13}$C-NMR (DMSO-d$_6$): δ166.79, 164.64, 139.95, 136.96, 134.15, 130.84, 129.27, 127.85, 124.41, 123.84, 119.30, 115.72, 38.25, 32.96, 28.42, 19.18; MS (DCI) m/e: 336(MH$^+$); IR (KBr): 3422, 2962, 1700, 1652, 1532.

Anal. calcd for C$_{21}$H$_{21}$N$_1$O$_3$·1.5 H$_2$O: C, 69.60; H, 6.68; N, 3.86. Found: C, 69.53; H, 6.97; N, 3.76.

EXAMPLE 13

N-[2-(Trimethylsilyl)ethoxymethyl]-4-[[(5,6,7,8-tetrahydro-5,5-dimethyl-8-phenyl-8-hydroxy-2-naphthalenyl)amino]carbonyl]benzoic acid, methyl ester (XIc)

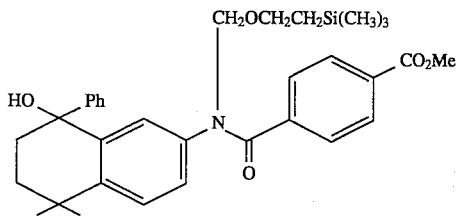

To a solution of compound Xa (595 mg, 1.24 mmol) in anhydrous tetrahydrofuran at −78° C. was added phenylmagnesium bromide (3.0M solution in diethyl ether, 0.59 mL, 1.76 mmol). After 10 minutes at −78° C., the reaction mixture was diluted with ethyl acetate (100 mL) and washed with water (100 mL). The organic phase was evaporated and the residue chromatographed on silica gel (eluted with 20% ethyl acetate in hexane) to give 449 mg (Y: 67%) of the title compound; $^1$H-NMR (CDCl$_3$): δ7.85 (d, 2H), 7.20–6.80 (m 10H) 5.20 (m, 2H) 3.95 (s, 3H) 3.65 (m, 2H ), 2.20–2.00 (m, 2H), 1.85 (m, 1H), 1.50 (m, 1H), 1.40 (s, 3H), 1.30 (s, 3H), 0.95 (m, 2H), 0.00 (s, 9H); MS (DCI) m/e: 542 (MH$^+$-H$_2$O).

EXAMPLE 14

4-[[(5,6,-Dihydro-5,5-dimethyl-8-phenyl-2-naphthalenyl)amino]carbonyl]benzoic acid, methyl ester (I¹c)

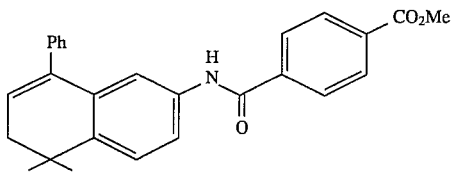

To a solution of compound XIc (as monohydrate, 449 mg, 0.83 mol) in toluene (10 mL) was added p-toluene sulfonic acid (190 mg, 1.0 mmol). After heating at 75° C. for 0.5 hour, the reaction mixture was diluted with ethyl acetate (100 mL) and washed with saturated sodium bicarbonate solution (100 mL). The organic phase was concentrated in vacuo and the residue chromatographed on silica gel (eluted with 15% ethyl acetate in hexane) to give 162 mg (Y: 48%) of the title compound; $^1$H-NMR (CDCl$_3$): δ8.15 (d, J=8.5 Hz, 2H), 7.90 (d, J=8.5 Hz, 2H), 7.90 (m, 1H), 7.65 (m, 1H), 7.40 (m, 5H), 6.90 (m, 1H), 6.05 (t, J=4.6 Hz, 1H), 3.95 (s, 3H), 2.40 (d, J=4.6 Hz, 2H), 1.40 (s, 6H); MS (DCI) m/e: 412 (MH$^+$).

EXAMPLE 15

4-[[(5,6-Dihydro-5,5-dimethyl-8-phenyl-2-naphthalenyl)amino]carbonyl]benzoic acid (I²c)

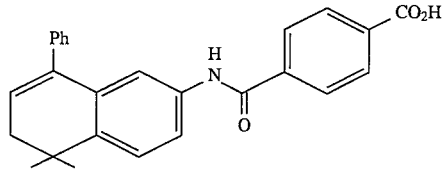

To a stirred solution of compound I¹c (0.21 mmol, 86 mg) in a 1:1 ethanol and tetrahydrofuran solution (5 mL) was added 10N NaOH (2.1 mmol, 0.21 mL) at room temperature. After 72 hours, an excess of 1N HCl (20 mL) was added, the precipitate collected by vacuum filtration, washed with 1N HCl, water, and dried to give 74 mg (Y: 89%) of the title compound; $^1$H-NMR (DMSO-d$_6$): δ10.29 (s, 1H), 7.98 (m, 4H), 7.76 (dd, J=8.4, 2.1 Hz, 1H), 7.35 (m, 7H), 5.97 (t, J=4.6 Hz, 1H), 2.89 (d, J=4.6 Hz, 2H), 1.27 (s, 6H); $^{13}$C-NMR (DMSO-d$_6$): 166.70, 164.58, 140.46, 140.33, 138.81, 138.62, 136.78, 133.39, 133.10 129.16, 128.42, 128.35, 127.89, 127.18, 126.83, 124.04, 119.84, 118.03, 38.41, 32.99, 28.04; MS (DCI) m/e: 398 (MH$^+$); IR (KBr): 3056, 2958, 1700, 1652, 1532.

Anal. calcd for C$_{26}$H$_{23}$O$_3$N$_1$·1.54 H$_2$O: C, 73.45; H, 5.81; N, 3.29. Found: C, 73.05; H, 5.53; N, 3.22.

EXAMPLE 16

4,4-Dimethyl-7-diazotetrafluorborate-1-tetralone (XIII)

To 4,4-dimethyl-7-amino-1-tetralone (15.10 g, 79.89 mmol) was added fluoboric acid (27.86 mL) diluted with water (27.86 mL) at 0° C. A cold solution of sodium nitrate (13.75 g, 199 mmol) in water (27.86 mL) was added slowly while keeping the temperature at about 10° C. The mixture was then cooled to 0° C., filtered and washed with 5% fluoboric acid (200 mL) and dried in vacuo to give 20.5 g (Y: 89%) of the title compound; $^1$H-NMR (DMSO-d$_6$): δ9.15 (d, J=2.5 Hz, 1H), 8.75 (dd, J=8.5, 2.5 Hz, 1H), 8.20 (d, J=8.5 Hz, 1H), 2.87 (t, J=7.0 Hz, 2H), 2.07 (t, J=7.0 Hz, 2H), 1.43 (s, 6H); MS (DCI) m/e: 193 (MH$^+$-N$_2$BF$_4$).

EXAMPLE 17

4,4-Dimethyl-7-hydroxy-1-tetralone (XIV)

Compound XIII (1.19 g, 4.13 mmol) was added to an already boiling solution of sulfuric acid (3.0 mL) and water (30 mL). After 1 hour at reflux the reaction mixture was cooled and extracted with ethyl acetate (2×50 mL). The combined organic phases were concentrated in vacuo and the residue chromatographed on silica gel (eluted with 20% ethyl acetate in hexane) to give 690 mg (Y: 88%) of the title compound; $^1$H-NMR (CDCl$_3$): δ7.48 (d, J=2.5 Hz, 1H), 7.33 (d, J=8.5 Hz, 1H), 7.05 (dd, J=8.5, 2.5 Hz, 1H), 2.75 (t, J=7.0 Hz, 2H), 2.00 (t, J=7.0 Hz, 2H), 1.38 (s, 6H).

EXAMPLE 18

4,4-Dimethyl-7-trifluoromethanesulfonate-1-tetralone (XV)

To a solution of compound XIV (690 mg, 3.63 mmol) in anhydrous pyridine (10 mL) was added trifluoromethanesulfonic anhydride (4.42 mmol, 0.74 mL) at 0° C. The reaction mixture was then allowed to warm to room temperature. After 16 hours, 1N HCl (25 mL) was added and the mixture was extracted with ethyl acetate (2×50 mL). The combined organic phases were dried over anhydrous magnesium sulfate and concentrated in vacuo to give 1.17 g (Y: 100%) of the title compound; $^1$H-NMR (CDCl$_3$): δ7.88 (d, J=2.8 Hz, 1H), 7.52 (d, J=8.7 Hz, 1H), 7.40 (dd, J=8.7, 2.8 Hz, 1H), 2.76 (t, J=7.0 Hz, 2H), 2.04 (t, J=7.0 Hz, 2H), 1.40 (s, 6H); MS (DCI) m/e: 323 (MH$^+$).

EXAMPLE 19

5,5-Dimethyl-8-oxo-5,6,7,8-tetrahydronaphthalene-2-carboxylic acid, methyl ester (XVIa)

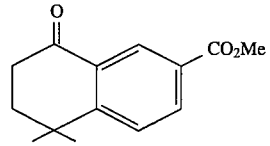

To a solution of compound XV (1.15 g, 3.57 mmol) in methanol (10.8 mL) and dimethyl sulfoxide (10.8 mL) was added triethylamine (1.09 mL, 7.82 mmol) palladium (II) acetate (24 mg, 0.11 mmol) and 1,3-bis(diphenylphosphino)propane (44 mg, 0.11 mmol). The reaction mixture was then saturated with carbon monoxide at room temperature and heated to 70° C. under a balloon of carbon monoxide for 3 hours. After cooling to room temperature, the reaction mixture was poured into water and extracted with ethyl acetate. The organic phase was then concentrated in vacuo and the residue chromatographed on silica gel (eluted with 15% ethyl acetate in hexane) to give 692 mg (Y: 93%) of the title product; $^1$H-NMR (CDCl$_3$): δ8.66 (d, J=2.0 Hz, 1H), 8.18 (dd, J=8.3, 2.0 Hz, 1H), 7.52 (d, J=8.3 Hz, 1H), 3.92 (s, 3H), 2.76 (t, J=7.0 Hz, 2H), 2.04 (t, J=7.0 Hz, 2H), 1.41 (s, 6H); MS (DCI) m/e: 233 (MH$^+$).

EXAMPLE 20

5,5-Dimethyl-8-hydroxy-8-phenyl-5,6,7,8-tetrahydro-naphthalene-2-carboxylic acid, methyl ester (XVIIa)

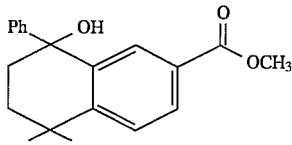

To a solution of compound XVIa (167 mg 0.72 mmol,) in tetrahydrofuran (5 mL) at −78° C. was added phenylmagnesium bromide (3.0M solution in diethyl ether, 1.08 mmol, 0.35 mL). After warming to room temperature (2 hours), the reaction mixture was concentrated and the residue chromatographed on silica gel (eluted with 10% ethyl acetate in hexane) to give 152 mg (Y: 68%) of the title product; $^1$H-NMR (CDCl$_3$): δ7.95 (dd, J=8.3, 2.0 Hz, 1H), 7.85 (d, J=2.0 Hz, 1H), 7.50 (d, J=8.3 Hz, 1H), 7.25 (m, 5H), 3.82 (s, 3H), 2.20 (m, 2H), 1.85 (m, 1H), 1.60 (m, 1H), 1.43 (s, 3H), 1.38 (s, 3H); MS (DCI) m/e: 311 (MH$^+$).

EXAMPLE 21

5,5-Dimethyl-5,6-dihydro-8-phenyl-naphthalene-2-carboxylic acid (XVIIIa)

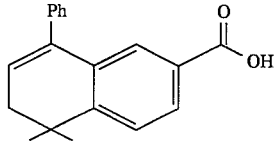

To a solution of compound XVIIa (150 mg, 0.484 mmol) in toluene (7 mL) was added a few milligrams (2–4 mg) of p-toluenesulfonic acid. After heating at 70° C. for 5 minutes, the reaction mixture was cooled and concentrated in vacuo. The residue was then dissolved in ethyl alcohol (7 mL) and treated with 10N NaOH (7.5 mmol, 0.74 mL) at room temperature. After 16 hours, an excess of 1N HCl (30 mL) was added and the precipitate collected by vacuum filtration to give 135 mg (Y: 99%) of the title compound; $^1$H-NMR (DMSO-d$_6$): δ7.95 (dd, J=2.0, 8.5 Hz, 1H), 7.75 (d, J=2.0 Hz, 1H), 7.47 (d, J=8.5 Hz, 1H), 7.38 (m, 5H), 6.05 (t, J=4.6 Hz, 1H), 2.40 (d, J=4.6 Hz, 2H), 1.40 (s, 6H); MS (DCI) m/e: 279 (MH$^+$).

EXAMPLE 22

4-[[(5,6-Dihydro-5,5-dimethyl-8-phenyl-2-naphthalenyl)carbonyl]amino]benzoic acid, methyl ester (I$^3$a)

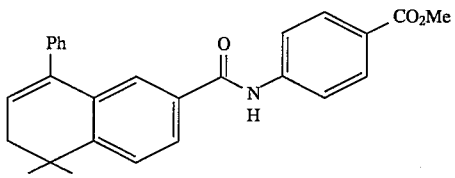

A solution of compound XVIIIa (135 mg, 0.485 mmol) in thionylchloride (5 mL) with 2 drops of N,N-dimethylformamide was allowed to stir at room temperature. The mixture became homogeneous within 1 hour and was then concentrated in vacuo. The residue was dissolved in anhydrous pyridine (5 mL) to which was added methyl 4-aminobenzoate (Aldrich, 0.534 mmol, 81 mg) o After 16 hours at room temperature, the mixture was diluted with 1N HCl, extracted with ethyl acetate (100 mL), washed with 1N HCl (3×100 mL) and washed with saturated sodium bicarbonate (2×100 mL). The organic phase was then separated, dried over magnesium sulfate and concentrated in vacuo to give 68 mg (Y: 34%) of the title compound; $^1$H-NMR (CDCl$_3$): δ8.05 (d, J=7.0 Hz, 2H), 7.75 (m, 2H), 7.65 (d, J=7.0 Hz, 2H), 7.50 (m, 1H), 7.40 (m, 5H), 6.08 (t, J=4.6 Hz, 1H), 3.90 (s, 3H), 2.45 (d, J=4.6 Hz, 2H), 1.40 (s, 6H); MS (DCI) m/e: 412 (MH$^+$).

EXAMPLE 23

4-[[(5,6-Dihydro-5,5-dimethyl-8-phenyl-2-naphthalenyl)carbonyl]amino]benzoic acid (I$^4$a)

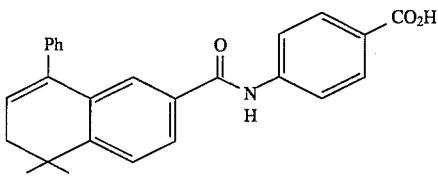

To a stirred solution of compound I$^3$a (0.165 mmol, 68 mg) in ethanol (5 mL) was added 10N NaOH (0.165 mL, 1.65 mmol) at room temperature. After 72 hours, an excess of 1N HCl (30 mL) was added. The precipitate was collected by vacuum filtration, washed with 1N HCl and water, and air dried to give 45 mg (Y: 69%) of the title compound; $^1$H-NMR (DMSO-d$_6$): δ10.42 (s, 1H), 7.83 (m, 5H), 7.52 (d, J=8.0 Hz, 1H), 7.38 (m, 6H), 6.05 (t, J=4.6 Hz, 1H), 2.33 (d, J=4.6 Hz, 2H), 1.30 (s, 6H); $^{13}$C-NMR (DMSO-d$_6$): 166.91, 166.00, 148.26, 143.25, 143.14, 139.86, 138.29, 133.36, 132.48, 130.17, 128.55, 128.31, 127.41, 127.31, 126.84, 125.40, 125.00 123.95, 119.38 119.30, 37.99, 33.52, 27.75; MS (DCI) m/e: 398 (MH$^+$); IR (KBr): 2958, 1688, 1596, 1522.

Anal. calcd for C$_{26}$H$_{23}$N$_1$O$_3$•0.5 H$_2$O: C, 76.83; H, 5.95; N, 3.45. Found: C, 76.47; H, 6.00; N, 3.22.

EXAMPLE 24

5,5-Dimethyl-8-ethyl-8-hydroxy-5,6,7,8-tetrahydronaphthalene-2-carboxylic acid, methyl ester (XVIIb)

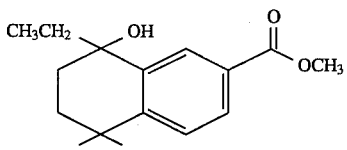

Using a method analogous to the preparation of the 8-phenyl derivative XVIIa, 490 mg (2.11 mmol) of compound XVIa gave 130 mg (Y: 24%) of the title compound.

EXAMPLE 25

5,6-Dihydro-8-ethyl-5,5-dimethylnaphthalene-2-carboxylic acid (XVIIIb)

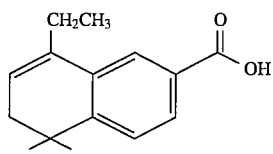

Using a method analogous to the the preparation of 8-phenyl derivative XVIIIa, 130 mg (0.49 mmol) of compound XVIIb gave 113 mg (Y: 100%) of the title product; $^1$H-NMR (DMSO-$d_8$): δ7.98 (d, J=2.0 Hz, 1H), 7.95 (dd, J=8.5, 2.0 Hz, 1H), 7.40 (d, J=8.5 Hz, 1H), 5.83 (t, J=4.6 Hz, 1H), 2.55 (q, J=7.5 Hz, 2H), 2.15 (d, J=4.6 Hz, 2H), 1.27 (s, 6H), 1.18 (t, J=7.5 Hz, 3H).

EXAMPLE 26

4-[[(5,6-Dihydro-5 5-dimethyl-8-ethyl-2-naphthalenyl)carbonyl]amino]benzoic acid, methyl ester (I$^3$b)

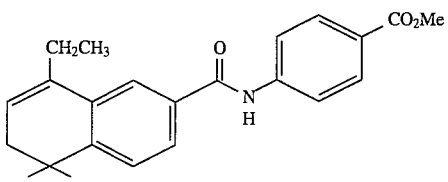

Using a method analogous to the preparation of the 8-phenyl derivative I$^3$a, 113 mg (0.491 mmol) of compound XVIIIb gave 163 mg (Y: 92%) of the title compound; $^1$H-NMR (CDCl$_3$): δ8.08 (d, J=8.5 Hz, 2H), 7.95 (bs, 1H), 7.79 (d, J=2.0 Hz, 1H), 7.75 (d, J=8.5 Hz, 2H), 7.65 (dd, J=8.0, 2.0 Hz, 1H), 7.40 (d, J=8.0 Hz, 1H), 5.88 (t, J=4.6 Hz, 1H), 3.90 (s, 3H), 2.55 (q, J=7.5 Hz, 2H), 2.25 (d, J=4.6 Hz, 2H), 1.30 (s, 6H), 1.18 (t, J=7.5 Hz, 3H); MS (DCI) m/e: 364 (MH$^+$).

EXAMPLE 27

4-[[(5,6-Dihydro-5,5-dimethyl-8-ethyl-2-naphthalenyl)carbonyl]amino]benzoic acid (I$^4$b)

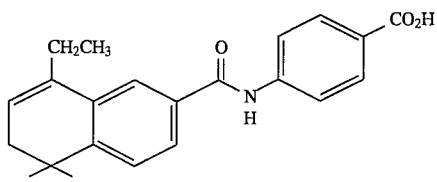

Using a method analogous to the preparation of the 8-phenyl derivative I$^4$a, 163 mg (0.45 mmol) of compound I$^3$b gave 128 mg (Y: 92%) of the title compound; $^1$H-NMR (DMSO-$d_6$): δ10.46 (s, 1H), 7.91 (m, 4H), 7.77 (m, 2H), 7.45 (d, J=7.9 Hz, 1H), 5.84 (t, J=4.6 Hz, 1H), 2.52 (q, J=7.4 Hz, 2H), 2.17 (d, J=4.6 Hz, 2H), 1.21 6H), 1.11 (t, J=7.4 Hz, 3H); $^{13}$C-NMR (DMSO-$d_6$): 166.97 166.133, 148.61, 143.33, 136.36, 133.27, 132.54, 130.19, 126.72, 125.52, 123.95, 122.80, 122.11, 119.50, 119.41, 37.62, 33.42, 27.94, 24.65, 12.86; MS (DCI) m/e: 350 (MH$^+$); IR (KBr): 2964, 1690, 1596, 1524.

Anal. calcd. for $C_{22}H_{23}O_3N_1 \cdot 0.75\ H_2O$: C, 72.81; H, 6.80; N, 3.86. Found: C, 72.84; H, 6.61; N, 3.86.

EXAMPLE 28

8-Hydroxy-5,5,8-trimethyl-5,6,7,8-tetrahydronaphthalene-2-carboxylic acid, methyl ester (XVIIc)

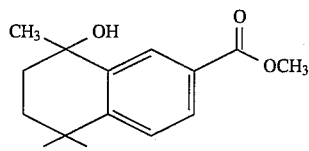

Using a method analogous to the preparation of the 8-phenyl derivative XVIIa, 292 mg (1.26 mmol) of compound XVIa gave 188 mg (Y: 60%) of the title product; $^1$H-NMR (CDCl$_3$): δ8.29 (d, J=2.0 Hz, 1H), 7.85 (dd, J=8.0 Hz, 2.0 Hz, 1H), 7.38 (d, J=8.0 Hz, 1H), 3.90 (s, 3H), 2.0 (t, J=7.0 Hz, 2H), 1.87 (t, J=7.0 Hz, 2H), 1.60 (d, J=1.3 Hz, 3H), 1.38 (s, 6H).

EXAMPLE 29

5,6-Dihydro-5,5,8-trimethylnaphthalene-2-carboxylic acid (XVIIIc)

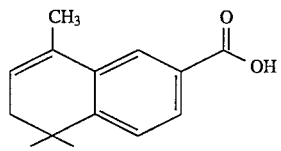

Using a method analogous to the preparation of the 8-phenyl derivative XVIIIa, 188 mg (0.76 mmol) of compound XVIIc gave 154 mg (Y: 94%) of the title compound; $^1$H-NMR (DMSO-$d_6$): δ7.96 (m, 2H), 7.40 (d, J=8.0 Hz, 1H), 5.87 (m, 1H), 2.27 (m, 2H), 2.17 (d, J=1.3 Hz, 3H), 1.27 (s, 6H).

EXAMPLE 30

4-[[(5,6-Dihydro-5,5,8-trimethyl-2-naphthalenyl)carbonyl]amino]benzoic acid, methyl ester (I$^3$c)

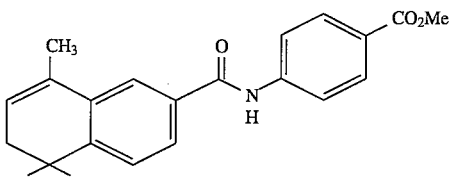

Using a method analogous to the preparation of the 8-phenyl derivative I$^3$a, 154 mg (0.713 mmol) of compound XVIIIc gave 90 mg (Y: 36%) of the title product; $^1$H-NMR (CDCl$_3$): δ8.05 (d, J=8.5 Hz, 2H), 7.90 (bs, 1H), 7.75 (d, J=8.5 Hz, 2H), 7.75 (d, J=2.0 Hz, 1H), 7.65 (dd, J=8.0, 2.0 Hz, 1H), 7.43 (d, J=8.0 Hz, 1H), 5.87 (m, 1H), 3.92 (s, 3H), 2.27 (m, 2H), 2.18 (d, J=1.3 Hz, 3H), 1.30 (s, 6H); MS (DCI) m/e: 350 (MH$^+$).

EXAMPLE 31

4-[[(5,6-Dihydro-5,5,8-trimethyl-2-naphthalenyl)carbonyl]amino]benzoic acid (I⁴c)

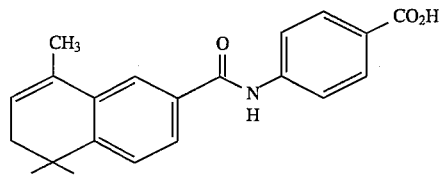

Using a method analogous to the preparation of the 8-phenyl derivative I⁴a, 90 mg (0.26 mmol) of compound I³c gave 70 mg (Y: 81%) of the title compound; ¹H-NMR (DMSO-d₆): δ12.72 (bs, 1H), 10.46 (s, 1H), 7.89 (m, 5H), 7.79 (dd, J=8.0, 2.0 Hz, 1H). 7.72 (d, J=2.0 Hz, 1H), 7.45 (d, J=8.0 Hz, 1H), 5.85 (m, 1H), 2.17 (m, 1H), 2.09 (d, J=1.3 Hz, 3H), 1.22 (s, 6H); MS (DCI) m/e: 336 (MH⁺); IR (KBr): 2958, 1674, 1656, 1416; ¹³C-NMR: 166.93, 166.13, 148.21, 143.38, 133.98, 132.58, 130.63, 130.22, 126.89, 125.36, 124.90, 123.83, 122.48, 119.48, 119.39, 37.84, 33.54, 28.14, 19.12.

Anal. calcd for C₂₁H₂₁N₁O₃: C, 75.20; H, 6.31; N, 4.1. Found C, 74.90; H, 6.36; N, 3.99.

EXAMPLE 32

1-(5,6-Dihydro-5,5-dimethyl-8-phenyl-naphthalen-2-yl)ethanone (XIXa)

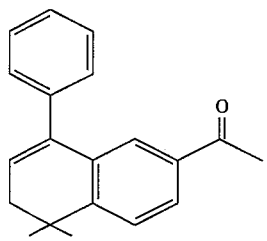

To a stirred solution of compound XVIIIa (816 mg, 2.94 mmol) in diethyl ether (15.0 mL) at −78° C. was added methyllithium (1.4M solution in diethyl ether, 4.19 mL, 5.88 mmol). After 1 hour at room temperature, 1N HCl (50 mL) was added. The organic phase was separated, washed with brine (50 mL), 1N NaOH (50 mL), dried over anhydrous magnesium sulfate and concentrated to give 600 mg (Y: 74%) of the title compound; ¹H-NMR (CDCl₃): δ7.83 (dd, J=8.0, 1.7 Hz, 1H), 7.63 (d, J=1.7 Hz, 1H), 7.46 (d, J=8.0 Hz, 1H), 7.37 (m, 5H), 6.05 (t, J=4.7 Hz, 1H), 2.44 (s, 3H), 2.37 (d, J=4.7 Hz, 2H), 1.35 (s, 6H); MS (DCI) m/e: 277 (MH⁺).

EXAMPLE 33

4-(E,Z)-[2-(5,6dihydro-5,5-dimethyl-8-phenyl-2-naphthalenyl)-1-propenyl]benzoic acid, ethyl ester (I⁵a)

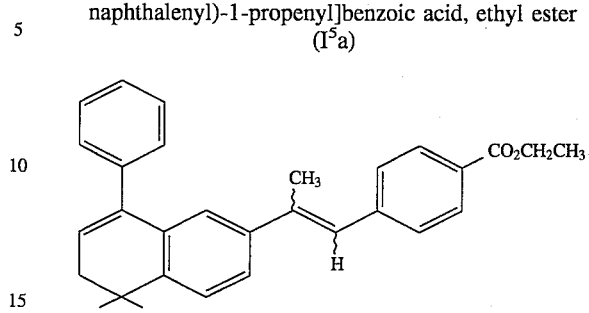

Methyl p-[(diethoxyphosphoryl)methyl]benzoate (1.02 g, 3.40 mmol, prepared as in Liebigs Ann. Chem. 1985, 929) was added to a 1M dimsyl anion solution in dimethylsulfoxide (3.09 mL, 3.09 mmol, prepared by warming sodium hydride in dimethylsulfoxide for 1 hour at 65° C.). After 30 minutes, the mixture was added to a solution of compound XIXa (595 mg, 2.16 mmol) in dimethylsulfoxide (6.50 mL) at room temperature. After 3 hours at room temperature, a 2M solution of sodium ethoxide in ethanol (1.74 mL, 3.48 mmol) was added. After 16 hours at room temperature, the mixture was diluted with 5% sodium bicarbonate (50 mL) and extracted with diethyl ether (50 mL×3). The combined organic phases were concentrated in vacuo and the residue chromatographed on silica gel (5% ethyl acetate in hexane) to give 159 mg (Y: 18%) of the title compound. NMR indicated a mixture of isomers (E:Z) (4:1).

EXAMPLE 34

4-(E)-[2-(5,6-dihydro-5,5-dimethyl-8-phenyl-2-naphthalenyl)-1-propenyl]benzoic acid (I⁶a)

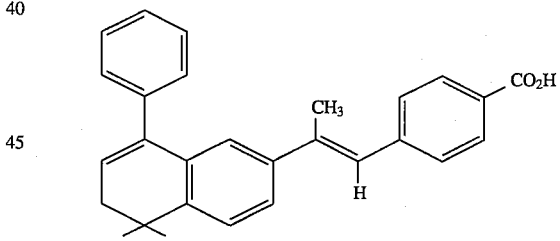

To a stirred solution of compound I⁵a (159 mg, 0.388 mmol) in ethanol (15.0 mL) at room temperature was added a 10N NaOH solution (0.39 mL, 3.90 mmol). After 48 hours, the mixture was diluted with an excess of 1N HCl (40.0 mL) and then filtered. After washing with water and drying, the solid was recrystallized from ethanol to provide 60 mg (Y: 40%) of the title compound; ¹H-NMR (DMSO-d₆): δ7.91 (d, J=8.3 Hz, 2H), 7.42 (m, 9H), 7.06 (d, J=1.7 Hz, 1H), 6.70 (s, 1H), 6.03 (t, J=4.6 Hz, 1H), 2.34 (d, J=4.6 Hz, 2H), 2.12 (s, 3H), 1.31 (s, 6H); ¹³C-NMR (DMSO-d₆): 144.42, 140.58, 140.14, 138.94, 138.72, 133.12, 129.26, 129.07, 128.47, 128.35, 127.32, 126.71, 125.89, 125.32, 124.07, 123.06, 38.25, 33.16, 27.94, 17.38; MS (DCI) m/e: 395 (MH⁺); IR (KBr): 2958, 1680, 1602, 1292.

Anal. calcd. for C₂₇H₂₆O₂: C, 84.78; H, 6.85. Found: C, 84.98; H, 6.66.

EXAMPLE 35

4,4-Dimethyl-7-[(t-butyldimethylsilyl)oxy]-1-tetralone (XXIa)

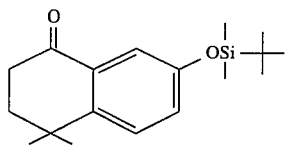

To a solution of compound XIV (2.00 g, 10.5 mmol) in dimethylformamide (16 mL) was added tertbutyldimethylsilyl chloride (1.90 g, 12.6 mmol) and imidazole (1.79 g, 26.3 mmol) at room temperature. After 5 hours, 5% NaHCO$_3$ (50 mL) was added and the mixture was extracted with hexane (2×75 mL). The combined organic phases were dried over anhydrous magnesium sulfate and concentrated in vacuo to give 3.22 g (Y: 99%) of the title compound; $^1$H-NMR (CDCl$_3$): δ7.44 (d, J=2.8 Hz, 1H), 7.29 (d, J=8.7 Hz, 1H), 7.01 (dd, J=8.7, 2.8 Hz, 1H), 2.71 (t, J=7.0 Hz, 2H), 1.99 (t, J=7.0 Hz, 2H), 1.36 (s, 6H), 0.98 (s, 9H), 0.20 (s, 6H); MS (DCI) m/e: 305 (MH$^+$).

EXAMPLE 36

2-[(t-Butyldimethylsilyl)oxy]-5,6-dihydro-5,5-dimethyl-8-trifluoromethanesulfonylnaphthalene (XXIIa)

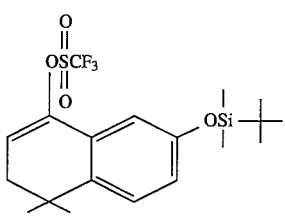

To a solution of compound XXIa (2.73 g, 8.98 mmol) in tetrahydrofuran (80.0 mL) at −78° C. was added sodium bis(trimethylsilyl)amide (1.0M solution in tetrahydrofuran, 9.88 mmol, 9.88 mL) and N-(2-pyridyl)triflimide (9.88 mmol, 3.54 g). After stirring for 1 hour at −78° C. and 1.5 hours at room temperature, the reaction mixture was concentrated in vacuo and the residue chromatographed on silica gel (eluted with 10% ethyl acetate in hexane) to give 2.26 g (Y: 58%) of the title product; $^1$H-NMR (CDCl$_3$): δ7.15 (d, J=8.4 Hz, 1H), 6.85 (d, J=2.5 Hz, 1H), 6.78 (dd, J=8.4, 2.5 Hz, 1H), 5.94 (t, J=4.8 Hz, 1H), 2.38 (d, J=4.8 Hz, 2H), 1.27 (s, 6H), 0.98 (s, 9H), 0.20 (s, 6H); MS (DCI) m/e: 437 (MH$^+$).

EXAMPLE 37

2-(t-Butyldimethylsilyloxy)-5,6-dihydro-5,5-dimethyl-8-phenyl-naphthalene (XXIIIa)

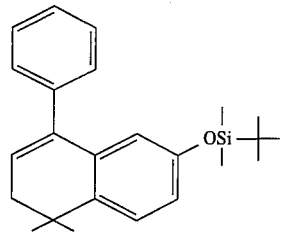

To a solution of compound XXIIa (2.26 g, 5.18 mmol) in 1-methyl-2-pyrrolidinone (25.0 mL) at room temperature was added triphenylarsine (300 mg, 0.980 mmol), tris-(dibenzylideneacetone)dipalladium (O) (147 mg, 0.16 mmol), and tributylphenyltin (4.18 g, 11.4 mmol). After stirring at 85° C. for 16 hours, water (50 mL) and ethyl acetate (50 mL) were added. The organic phase was separated and stirred over an aqueous saturated potassium fluoride solution for 30 minutes. The organic phase was again separated, concentrated in vacuo and the residue chromatographed on silica gel (eluted with 100% hexane) to give 1.10 g (Y: 58%) of the title product; $^1$H-NMR (CDCl$_3$): δ7.10 (m, 5H), 6.97 (d, J=8.4 Hz, 1H), 6.41 (dd, J=8.4 Hz, 2.5 Hz, 1H), 6.20 (d, J=2.5 Hz, 1H), 5.68 (t, J=4.8 Hz, 1H), 2.05 (d, J=4.8 Hz, 2H), 1.02 (s, 6H), 0.60 (s, 9H), 0.00 (s, 6H); MS (DCI) m/e: 365 (MH$^+$).

EXAMPLE 38

5,6-Dihydro-5,5-dimethyl-8-phenyl-naphthalen-2-ol (XXVa)

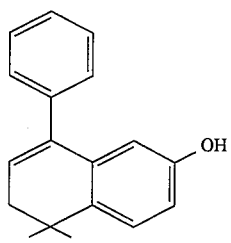

To a solution of compound XXIIIa 1.10 g, 3.02 mmol) in tetrahydrofuran (10.0 mL) at room temperature was added tetrabutylammonium fluoride (1.0M solution in tetrahydrofuran, 3.32 mL, 3.32 mmol). After 5 minutes the reaction mixture was concentrated in vacuo and the residue chromatographed on silica gel (eluted with 10% ethyl acetate in hexane) to give 575 mg (Y: 76%) of the title product; $^1$H-NMR (CDCl$^3$): δ7.36 (m, 5H), 7.23 (d, J=8.3 Hz, 1H), 6.71 (dd, J=8.3, 2.7 Hz, 1H), 6.49 (d, J=2.7 Hz, 1H), 5.99 (t, J=4.6 Hz, 1H), 2.34 (d, J=4.6 Hz, 2H), 1.32 (s, 6H); MS (DCI) m/e: 251 (MH$^+$).

EXAMPLE 39

Di-tert-butyl terephthalate (XXVI)

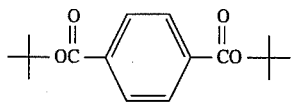

To a solution of terephthaloylchloride (2.00 g, 9.85 mmol) in dry pyridine (25.0 mL) was added tert-butyl alcohol (803 mg, 10.8 mmol). After 16 hours at 85° C. water (75.0 mL) was added and the solid filtered. The solid was dissolved in diethyl ether (40 mL) and washed with saturated sodium bicarbonate (2×75 mL). The organic phase was then dried over anhydrous magnesium sulfate and concentrated in vacuo to give 1.15 g (Y: 42%) of the title compound; $^1$H-NMR (CDCl$_3$): δ8.01 (s, 4H), 1.60 (s, 18H).

EXAMPLE 40

Mono-tert-butyl terephthalate (XXVII)

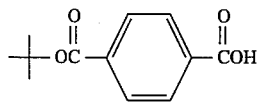

To a solution of potassium hydroxide (255 mg, 4.55 mmol) in 4.0 mL tert-butyl alcohol with 0.5 mL of water added for solubility was added compound XXVI (1.15 g, 4.14 mmol) in tert-butyl alcohol (5.5 mL). After 3 hours at 50° C., diethyl ether (35 mL) was added and the reaction mixture filtered. The solid was dissolved in water (35.0 mL), extracted with methylene chloride (2×50 mL), and then acidified with 1N HCl. The precipitate was then collected to give 270 mg (Y: 30%) of the title compound; $^1$H-NMR (CDCl$_3$): δ8.02 (m, 4H), 1.56 (s, 9H); MS (DCI) m/e: 223 (MH$^+$).

EXAMPLE 41

4-[[(5,6-Dihydro-5,5-dimethyl-8'-phenyl-2-naphthalenyl)oxy]carbonyl]benzoic acid, tert-butyl ester (I$^7$a)

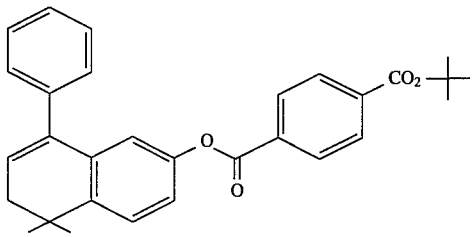

To a solution of compound XXVII (107 mg, 0.480 mmol) in methylene chloride (5 mL) at 0° C. was added oxalyl chloride (0.15 mL) and dimethylformamide (2 drops). After 2 hours at room temperature, the reaction mixture was concentrated in vacuo to give the corresponding acid chloride (compound XXIVa). To a solution of compound XXIVa (0.480 mmol) in dry pyridine (5 mL) was then added compound XXVa (120 mg, 0.48 mmol). After 16 hours at room temperature, the mixture was diluted with 1N HCl, extracted with ethyl acetate (100 mL), washed with 1N HCl (4×100 mL), and washed with saturated sodium bicabonate (2×100 mL). The organic phase was then separated, dried over magnesium sulfate and concentrated in vacuo to give 137 mg (Y: 63%) of the title compound; $^1$H-NMR (CDCl$_3$) δ8.16 (d, J=8.4 Hz, 2H), 8.06 (d, J=8.4 Hz, 2H), 7.35 (m, 6H), 7.07 (dd, J=8.4 Hz, 2.4 Hz, 1H), 6.84 (d, J=2.4 Hz, 1H), 6.04 (t, J=4.6 Hz, 1H), 2.38 (d, J=4.6 Hz, 2H), 1.61. (s, 9H), 1.36 (s, 6H); MS (DCI) m/e: 455 (MH$^+$).

EXAMPLE 42

4-[[(5,6-Dihydro-5,5-dimethyl-8-phenyl-2-naphthalenyl)oxy]carbonyl]benzoic acid (I$^8$a)

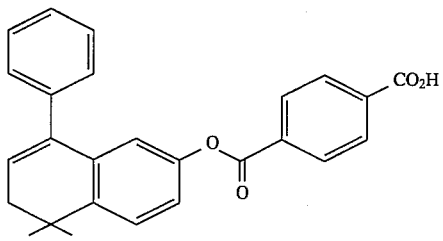

To a stirred solution of compound I$^7$a (137 mg, 0.30 mmol) in methylene chloride was added trifluoroacetic acid (0.270 mL) at room temperature. After 72 hours, 1N HCl (30 mL) was added. The precipitate was collected by vacuum filtration, washed with 1N HCl, and air dried to give 85 mg (Y: 71%) of the title compound; $^1$H-MR (CDCl$_3$): δ13.39 (bs, 1H), 8.15 (d, J=7.6 Hz, 2H), 8.05 (d, J=7.6 Hz, 2H), 7.38 (m, 6H), 7.18 (d, J=8.4 Hz, 1H), 6.73 (s, 1H), 6.06 (t, J=4.2 Hz, 1H), 2.35 (d, J=4.2 Hz, 2H), 1.32 (s, 6H); $^3$C-NMR (CDCl$_3$): 166.48, 163.99. 148.51, 142.55, 139.77, 138.17, 35.24, 134.59, 132.45, 131.61, 130.01, 129.66, 129.48, 128.57, 128.28, 127.63, 127.41, 125.24, 120.74, 118.36, 67.39, 38.24, 38.07, 33.12, 28.37; MS (DCI) m/e: 399 (MH$^+$); IR (KBr): 2964, 1738, 1698, 1246.

Anal calcd. for C$_{24}$H$_{22}$O$_4$·0.5 H$_2$O: C, 76.64; H, 5.69. Found: C, 76.66; H, 5.89.

EXAMPLE 43

4-Hydroxybenzoic acid tert-butyl ester (XXVIIIa)

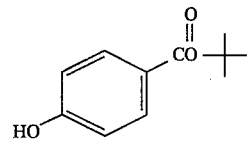

To a solution of 4-hydroxybenzoic acid (2.00 g, 14.5 mmol) in 1,4-dioxane (10.0 mL) saturated with isobutylene at −78° C. in a metal bomb was added concentrated sulfuric acid (0.150 mL). The bomb was sealed and warmed to room temperature. After 72 hours at room temperature, the reaction mixture was cooled to −78° C., poured into saturated sodium bicarbonate (30.0 mL) and extracted with diethyl ether (2×50.0 mL). The combined organic phases were concentrated and the residue chromatographed on silica gel (eluted with 5% methanol in methylene chloride to give 290 mg (Y: 10%) of the title product; $^1$H-NMR (CDCl$_3$): δ7.89 (d, J=8.8 Hz, 2H), 6.83 (d, J=8.8 Hz, 2H), 1.57 (s, 9H).

EXAMPLE 44

4-[[(5,6-Dihydro-5,5-dimethyl-8-phenyl-2-naphthalenyl)carbonyl]oxy]benzoic acid, tert-butyl ester (I⁹a)

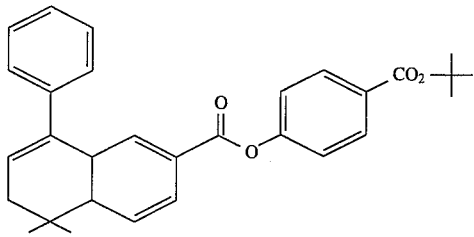

To a stirred solution of compound XVIIIa (200 mg, 0.720 mmol) in dry methylene chloride (7.00 mL) at 0° C. was added oxalyl chloride (0.075 mL) and dimethylformamide (2 drops). After 2 hours at room temperature, the mixture was concentrated in vacuo. To the residue in anhydrous pyridine (5.00 mL) was added compound XXVIIIa (154 mg, 0.792 mmol). After 2 hours at room temperature, the mixture was diluted with 1N HCl, extracted with ethyl acetate (50 mL), washed with 1N HCl (4×100 mL) and washed with saturated sodium bicarbonate (2×100 mL). The organic phase was then separated, concentrated in vacuo and the residue chromatographed on silica gel (eluted with 3% ethyl acetate in hexane) to give 203 mg (Y: 61%) of the title product; $^1$H-NMR (CDCl$_3$): δ8.05 (m, 3H), 7.85, (d, J=1.7 Hz, 1H), 7.51 (d, J=8.1 Hz), 7.38 (m, 6H), 7.18 (d, J=8.6 Hz, 1H), 6.07 (t, J=4.6 Hz, 1H), 2.40 (d, J=4.6 Hz, 2H), 1.59 (s, 9H), 1.38 (s, 6H); MS (DCI) m/e: 455 (MH$^+$).

EXAMPLE 45

4-[[(5,6-Dihydro-5,5-dimethyl-8-phenyl)-2-naphthalenyl)carbonyl]oxy]benzoic acid (I¹⁰a)

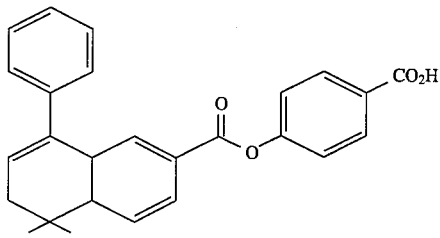

To a solution of compound I⁹a (203 mg, 0.480 mmol) in methylene chloride (5.00 mL) was added trifluoroacetic acid (0.400 mL) at room temperature. After 16 hours, 1N HCl (30 mL) was added. The precipitate was collected by vacuum filtration, washed with 1N HCl and air dried to give 133 mg (Y: 75%) of the title compound; $^1$H-NMR (DMSO-d$_6$): δ8.05–7.31 (m, 12H), 6.10 (t, J=4.6 Hz, 1H), 2.39 (d, J=4.6 Hz, 2H), 1.34 (s, 6H); IR (KBr): 2962, 1742, 1684, 1602; MS (DCI) m/e: 399 (MH$^+$).

Anal. calcd. for C$_{24}$H$_{22}$O$_4$•0.850 H$_2$O: C, 75.47; H, 5.77. Found: C, 75.52; H, 5.43.

EXAMPLE 46

5,5-Dimethyl-8-hydroxy-8-(2-fluorophenyl)-5,6,7,8-tetrahydronaphthalene-2-carboxylic acid, methyl ester (XVIId)

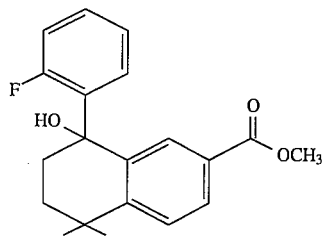

To a solution of compound XVIa (297 mg, 1.28 mmol) in tetrahydrofuran (7.0 mL) at –78° C. was added 2-fluorophenyllithium [0.35M solution in THF, 1.93 mmol, 5.50 mL; prepared by treating 2-fluoro-bromobenzene (552 mg, 3.15 mmol) in tetrahydrofuran (5.0 mL) with t-butyllithium (1.7M solution in pentane, 2.41 mmol, 4.09 mL) at –78° C. After 5 minutes at –78° C., 5.50 mL was transferred via syringe to the solution of compound XVIa]. After warming to room temperature (1 hour), the reaction mixture was concentrated and the residue chromatographed on silica gel (eluted with 10% ethyl acetate in hexane) to give 280 mg (Y: 67%) of the title product; $^1$H-NMR (CDCl$_3$): (dd, J=8.4, 1.7 Hz, 1H), 7.72 (d, J=1.7 Hz, 1H), 7.50 (m, 2H), 7.18 (m, 1H), 6.96 (m, 2H), 3.80 (s, 3H), 2.50 (m, 1H), 2.40 (d, J=2.8 Hz, 1H), 2.05 (m, 2H), 1.60 (m, 1H), 1.43 (s, 3H), 1.35 (s, 3H). MS (DCI) m/e: 329 (MH$^+$).

EXAMPLE 47

5,5-Dimethyl-5,6-dihydro-8-(2-fluorophenyl)naphthalene2-carboxylic acid (XVIIId)

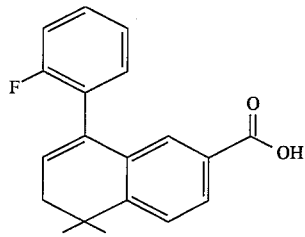

Using the method given for the preparation of 8-phenyl derivative XVIIIa, 280 mg (0.85 mmol) of compound XVIId gave 209 mg (Y: 83%) of the title product; $^1$H-NMR (DMSO-d$_6$): δ7.81 (dd, J=8.0, 1.8 Hz, 1H), 7.55–7.25 (m, 6H), 6.09 (t, J=4.5 Hz, 1H), 2.38 (d, J=4.5 Hz, 2H), 1.32 (s, 6H); MS (DCI) m/e 297 (MH$^+$).

EXAMPLE 48

4-[[[5,6-Dihydro-5,5-dimethyl-8-(2-fluorophenyl)-2-naphthalenyl]carbonyl]amino]benzoic acid methyl ester (I³g)

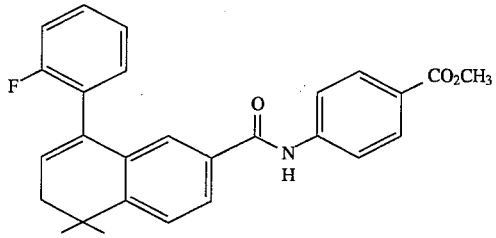

A solution of compound XVIIId (200 mg, 0.676 mmol) in anhydrous methylene chloride (5.0 mL) was treated with oxalyl chloride (0.20 mL, 2.29 mmol) and 2 drops of N,N-dimethylformamide at 0° C. The reaction mixture was then allowed to stir at room temperature. After 2 hours, the mixture was concentrated in vacuo. The residue was dissolved in anhydrous pyridine (5.0 mL) to which was added methyl 4-aminobenzoate (Aldrich, 102 mg, 0.68 mmol). After 2 hours at room temperature, the mixture was diluted with 1N HCl, extracted with ethyl acetate (100 mL), washed with 1N HCl (3×100 mL) and washed with saturated sodium bicarbonate (2×100 mL). The organic phase was then separated and concentrated in vacuo. The residue chromatographed on silica gel (eluted with 20% ethyl acetate in hexane) to give 226 mg (Y: 78%) of the title compound; $^1$H-NMR (CDCl$_3$): δ8.02 (d, J=8.7 Hz, 1H), 7.71 (m, 1H), 7.64 (d, J=8.7 Hz, 1H), 7.48 (d, J=8.0 Hz, 1H), 7.40–7.10 (m, 7H), 6.11 (t, J=4.5 Hz, 1H), 3.90 (s, 3H), 2.42 (d, J=4.5 Hz, 2H), 1.39 (s, 6H). MS (DCI) m/e: 430 (MH⁺).

EXAMPLE 49

4-[[[5,6-Dihydro-5,5-dimethyl-8-(2-fluorophenyl)-2-naphthalenyl]carbonyl]amino]benzoic acid (I⁴g)

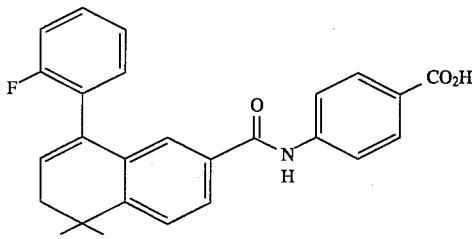

Using the method given for the preparation of the 8-phenyl derivative I⁴a, 226 mg (0.527 mmol) of compound I³g gave 180 mg (Y: 82%) of the title compound; $^1$H-NMR (DMSO-d$_6$) δ12.73 (s, 1H), 10.43 (s, 1H), 7.89–7.78 (m, 5H), 7.53 (d, J=8.0 Hz, 1H), 7.48–7.19 (m, 5H), 6.10 (t, J=4.5 Hz, 1H), 2.38 (d, J=4.5 Hz, 2H), 1.33 (s, 6H); $^{13}$C-NMR (DMSO-d$_6$): δ166.89, 165.80, 161.12, 147.85, 143.24, 133.08, 132.95, 132.57, 131.54, 130.18, 129.93, 129.48, 126.91, 125.37, 124.88, 124.29, 123.86, 119.42, 119.33, 115.75, 115.46, 37.89, 33.48, 27.75.

MS (DCI) m/e: 416 (MH⁺).

IR (KBr): 2962, 1688, 1594, 1520.

Anal. calcd. for $C_{26}H_{22}N_1O_3F_1 \cdot 0.25\ H_2O$: C, 74.36; H, 5.40; N, 3.34. Found: C, 74.50; H, 5.40; N, 3.17

EXAMPLE 50

5,5-Dimethyl-8-oxo-5,8-dihydronaphthalene-2-carboxylic acid, methyl ester (XXXa)

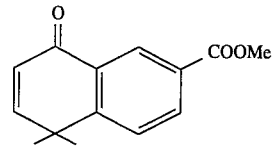

A mixture of a compound of formula XVI (Scheme XXI) in which R⁷ is methyl (2.00 g, 8.60 mmol), chlorotrimethylsilane (TMS-Cl, 1.12 g, 10.3 mmol) and 1,8-diazabicyclo[5.4.0]undec-7-ene (DBU, 1.70 g, 11.2 mmol) in 10 mL of anhydrous methylene chloride was stirred at reflux for 1 hour. The mixure was diluted with 75 mL of diethyl ether, washed with 20 mL of 0.1N of HCl, 20 mL of water, and dried over magnesium sulfate. The solvent was evaporated and the residue was dried in vaccum. To the residue was added 30 mL of acetonitrile and palladium acetate (2.12 g, 9.50 mmol). After stirring for 16 hours, additional palladium acetate (1.06 g, 4.75 mmol) was added, and the resulting mixture was stirred for 16 hours. The mixture was filtered through a pad of celite, and washed with acetonitrile. The filtrate collected was evaporated and the residue was diluted with water (30 mL) and extracted with ether (30 mL×3). The combined extracts were dried over magnesium sulfate, filtered, and evaporated. The residue was purified by flash chromatography on silica gel (eluted with EtOAc: hexane, 1:20 to 1:5) to give 1.42 g (64% yield) of the title compound as a solid; $^1$H-NMR (CDCl$_3$) δ1.50 (s, 6H), 3.94 (s, 3H), 6.41 (d, J=10.2 Hz, 1H), 6.94 (d, J=10.2 Hz, 1H), 7.62 (d, J=8.2 Hz, 1H), 8.22 (dd, J=2.0, 8.2 Hz, 1H), 8.82 (d, J=2.0 Hz, 1H); MS (DCI) m/e: 321 (MH⁺).

EXAMPLE 51

5,5,6-Trimethyl-8-oxo-5,6,7,8-tetrahydronaphthalene-2-carboxylic acid, methyl ester (XXXIa)

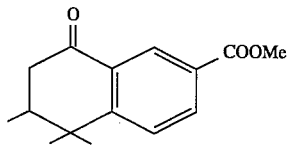

To a suspension of cuprous cyanide (724 mg, 8.08 mmol) in 40 mL of anhydrous ether was slowly added methyl lithium (1.4M in ether, 11.5 mL, 16.2 mmol) at –50° C. After stirring for 1 h, the solution was cooled to –78° C. and boron trifluoride etherate (573 mg, 4.04 mmol) was added followed by slow addition of enone ester XXXa (930 mg, 4.04 mmol) in 10 mL of ether. After stirring for 45 min, the reaction was quenched with saturated ammonium chloride solution (30 mL). The mixture was extracted with ether (30 mL×3). The combined ether extracts were dried over maganesium sulfate, filtered, and evaporated. The residue was purified by flash chromatography on silica gel (eluted with hexane: EtOAc, 20:1 to 5:1) to give 251 mg (25% yield) of the title compound as a solid; $^1$H-NMR (CDCl$_3$) δ1.05 (d, J=6.9 Hz, 3H), 1.30, 1.44 (s, 3H each), 2.15–2.30 (m, 1H), 2.55 (dd, J=9.3, 17.5 Hz, 1H), 2.81 (dd, J=4.5, 17.5 Hz, 1H), 3.93 (s, 3H), 7.55 (d, J=8.3 Hz, 1H), 7.69 (dd, J=1.9, 8.3 Hz, 1H), 8.66 (d, J=1.9 Hz, 1H); MS (DCI) m/e: 247 (MH⁺).

Anal. Calcd. for $C_{15}H_{18}O_3$: C, 73.15; H, 7.37. Found: C 72.78; H, 7.31.

EXAMPLE 52

5,5,6-Trimethyl-8-phenyl-5,6-dihydronaphthalene-2-carboxylic acid, methyl ester (IXXXIIa).

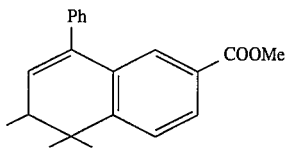

To a solution of compound XXXIa (390 mg, 1.58 mmol) in 10 mL of anhydrous tetrahydrofuran was added phenylmagnesiumbromide (3.0M in ether, 1.05 mL, 3.15 mmol) at −30° C. After stirring for 10 min, the solution was raised to 0° C. and stirred for 20 min. The reaction was quenched with 20 mL of saturated ammonium chloride and extracted with ethyl acetate (25 mL×3). The combined extracts were washed with water (20 mL), dried over magnesium sulfate, filtered and evaporated. To the residue was added 20 mL of anhydrous benzene and p-toluensulfonic acid (50 mg). The solution was stirred at reflux for 30 min and then evaporated. The residue was purified by flash chromatography on silica gel (eluted with EtOAc: hexane, 1:20 to 1:10) to give 380 mg (78% yield) of the title product as a light yellow oil; $^1$H-NMR (CDCl$_3$) δ1.01 (d, J=7.1 Hz, 3H), 1.29, 1.36 (s, 3H each), 2.35–2.43 (m, 1H), 3.82 (s, 3H), 5.94 (d, J=5.0 Hz, 1H), 7.33–7.42 (m, 5H), 7.43 (d, J=8.1 Hz, 1H), 7.69 (d, J=1.8 Hz, 1H), 7.90 (dd, J=1.8, 8.1 Hz, 1H); MS (DCI) m/e: 307 (MH$^+$).

Anal. Calcd. for $C_{21}H_{22}O_2$: C, 82.32; H, 7.24. Found: C 82.10; H, 7.32.

EXAMPLE 53

5,5,6-Trimethyl-8-phenyl-5,6-dihydronaphthalene-2-carboxylic acid (XVIIIe)

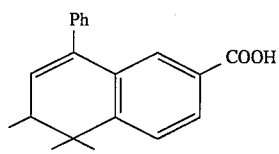

A solution of compound XXXIIa (224 mg, 0.73 mmol) and 2N NaOH (3.7 ml, 7.4 mmol) in 7 mL of terhydrofuran and 7 mL of methanol was stirred at 60° C. for 1.5 hours. The mixture was concentrated under reduced pressure and acidified with 10 mL of 1N HCl, extracted with EtOAc (20 mL×3). The combined extracts were washed with water (10 mL), dried over magnesium sulfate, filtered, and evaporated. The residue was crystallyzed from ether-hexane to give 220 mg of the product (quantative yield) as a solid; $^1$H-NMR (CDCl$_3$) δ1.02 (d, J=7.1 Hz, 3H), 1.31, 1.37 (s, 3H each), 2.35–2.45 (m, 1H), 5.95 (d, J=5.1 Hz, 1H), 7.30–7.40 (m, 5H), 7.46 (d, J=8.1 Hz, 1H), 7.73 (d, J=1.9 Hz, 1H), 7.94 (dd, J=1.9, 8.1 Hz, 1H); MS (DCI) m/e: 293 (MH$^+$).

Anal. Calcd. for $C_{20}H_{20}O_2$·0.125 H$_2$O: C, 81.53; H, 6.93. Found: C 81.68; H, 6.86.

EXAMPLE 54

4-[[(5,6-Dihydro-5,5,6-trimethyl-8-phenyl-2-naphthalenyl)carbonyl]amino]benzoic acid, methyl ester (I$^3$d)

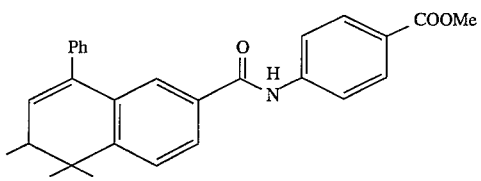

To a solution of compound XVIIIe (206 mg, 0.71 mmol) in 4 mL of methylene chloride was added oxatyl chloride (179 mg, 1.41 mmol) and 1 drop of dimethylformamide at 0° C. The solution was stirred at 0° C. for 2 hours and at room temperature for 1 hour. The solvent was evaporated and the residue was dried in vaccum. To the residue was added methyl p-aminobenzoate (128 mg, 0.85 mmol) and 4 mL of anydrous pyridine. The mixture was stirred at room temperature for 18 hours. The solvent was evaporated, and the residue was diluted with 1N HCl (20 mL) and extracted with EtOAc (20 mL×3). The combined extracts were dried over maganesium sulfate, filtered, and evaporated. The residue was purified by flash chromatography on silica gel (eluted with hexane: EtOAc, 10:1 to 5:1) to give 234 mg (78% yield) of the title compound as a foam; $^1$H-NMR (CDCl$_3$) δ1.03 (d, J=7.1 Hz, 3H), 1.30, 1.37 (s, 3H each), 2.35–2.45 (m, 1H), 3.90 (s, 3H), 5.98 (d, J=5.0 Hz, 1H), 7.30–7.41 (m, 5H), 7.46 (d, J=8.1 Hz, 1H), 7.51 (d, J=1.8 Hz, 1H), 7.65 (d, J=8.7 Hz, 1H), 7.72 (dd, J=1.8, 8.1 Hz, 1H), 7.97 and 8.00 (s over d, J=8.7 Hz, 3H); MS (DCI) m/e: 426 (MH$^+$)

Anal. Calcd. for $C_{28}H_{27}NO_3$·0.5 H$_2$O: C, 77.39, H, 6.50; N, 3.22. Found: C, 77.34; H, 6.19; N, 3.33.

EXAMPLE 55

4-[[(5,6-Dihydro-5,5,6-trimethyl-8-phenyl-2-naphthalenyl)carbonyl]amino]benzoic acid (I$^4$d)

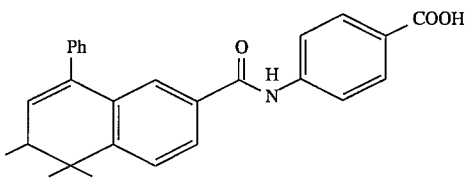

A mixture of compound I$^3$d (224 mg, 0.53 ml) and 2N NaOH (2.65 mL, 5.30 mmol) in 5 mL of tetrahydrofuran and 5 mL of methanol was stirred at room temperature for 16 hours. The resulting solution was acidified with 1N HCl and concentrated under reduced pressure. The residue was diluted with 20 mL of water and filtered. The collected solids were trituated in ether to give 127 mg (59% yield) of the title product as light yellow powder; $^1$H-NMR (DMSO-d$_6$) δ0.97 (d, J=7.1 Hz, 3H), 1.26, 1.31 (s, 3H each), 2.37–2.41 (m, 1H), 5.98 (d, J=5.0 Hz, 1H), 7.31–7.45 (m, 6H), 7.54 (d, J=8.1 Hz, 1H), 7.79–7.89 (m, 6H), 10.43 (s, 1H), 12.72 (s, 1H); MS (DCI) m/e: 411 (MH$^+$).

Anal. Calcd. for $C_{27}H_{25}NO_3$·0.5 H$_2$O: C, 77.12, H, 6.23; N, 3.33. Found: C, 77.41; H, 6.05; N, 3.26.

EXAMPLE 56

5,5,7-Trimethyl-8-oxo-5,6,7,8-tetrahydronaphthalene-2-carboxylic acid, methyl ester (XXXVa)

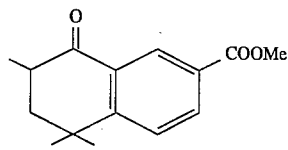

To a solution of a compound of formula XVI (Scheme XXII) in which $R^7$ is methyl (0.60 g, 2.58 mmol) in 10 mL of anhydrous tetrahydrofuran and 1 mL of hexamethylphosphoramide (HMPA) was added lithium his (trimethysilyl) amide (LHMDS, 1M in hexane, 2.71 mL, 2.71 mmol) at −78° C. under a nitrogen atmosphere. After strring for 2 hours, the solution was warmed to −40° C. and methyl iodide (0.73 g, 5.16 mmol) was added. The reaction was stirred for 2.5 hours, and quenched with saturated ammonium chloride solution (20 mL). The mixture was extracted with EtOAc (20 mL×3) and the combined extracts were dried over magnesium sulfate, and evaporated. The residue was purified by flash chromatography on silica gel (eluted with EtOAc: hexane, 1:30 to 1:10) to give 516 mg (81% yield) of the title product as a white solid; $^1$H-NMR (CDCl$_3$) δ1.27 (d, J=6.6 Hz, 3H), 1.40, 1.45 (s, 3H each), 1.91 (d, J=2.0 Hz, 1H), 1.94 (s, 1H), 2.78–2.91 (m, 1H); 3.93 (s, 3H), 7.50 (d, J=8.2 Hz, 1H), 8.16 (dd, J=1.9; 8.2 Hz, 1H), 8.64 (d, J=1.9 Hz, 1H); MS (DCI) m/e: 247.

Anal. Calcd. for $C_{15}H_{18}O_3$: C, 73.15, H, 7.37. Found: C, 73.15; H, 7.51.

EXAMPLE 57

5,5,7-Trimethyl-8-phenyl-5,6-dihydronaphthalene-2-carboxylic acid, methyl ester (XXXVIa)

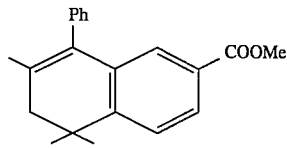

To a solution of ketone XXXVa (500 mg, 2.03 mmol) in 20 mL of tetrahydrofuran was slowly added phenyl magnesium bromide (3.0M in ether, 1.35 mL, 4.06 mmol) at 0° C. The red mixture was stirred at 0° C. for 1 hour, and quenched with saturated ammonium chloride solution (20 mL). The mixture was extrated with EtOAc (25 mL×3). The combined extracts were dried over magnesium sulfate, and evaporated. To the residue was added benzene (10 mL) and p-toluenesulfonic acid (0.1 g), and stirred at reflux for 30 min. The solvent was evaporated and the residue was purified by flash chromatography on silica gel (eluted with EtOAc: hexane, 1:30 to 1:10) to give 380 mg (61% yield) of the title product; $^1$H-NMR (CDCl$_3$) δ1.35 (s, 6H ), 1.73 (s, 3H), 2.31 (s, 2H), 3.77 (s, 3H), 7.17 (d, J=6.8 Hz, 2H), 7.29–7.45 (m, 5H), 7.80 (dd, J=1.8, 8.0 Hz, 1H); MS (DCI) m/e: 307.

EXAMPLE 58

5,5,7-Trimethyl-8-phenyl-5,6-dihydronaphthalene-2-carboxylic acid (XVIIIf)

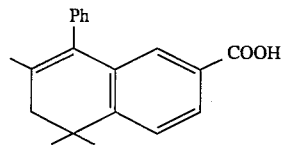

A solution of ester XXXVIa (180 mg, 0.62 mmol) and 1N NaOH (1.22 mL, 2 mmol) in 5 mL of tetrahydrofuran and 2 mL of MeOH was stirred at 60° C. for 3 hours. The solution was concentrated to approximate 3 mL under reduced pressure and diluted with 1N HCl (10 mL), extracted with EtOAc (30 mL×2). The combined extracts were washed with water (10 mL), dried over magnesium sulfate, and evaporated to give 150 mg of the title acid (83% yield) as a solid; $^1$H-NMR (CDCl$_3$) δ1.35 (s, 6H), 1.73 (s, 3H), 2.32 (s 2H), 7.15 (d, J=6.7 Hz, 2H), 7.32 (d, J=1.6 Hz, 1H); 7.35–7.45 (m, 4H), 7.86 (dd, J=1.6, 8.0 Hz, 1H); MS (DCI) m/e: 293 (MH$^+$).

Anal. Calcd. for $C_{20}H_{20}O_2$·0.25 $H_2O$ C, 80.91, H, 6.96. Found: C, 81.01; H, 6.82.

EXAMPLE 59

4-[[(5,6-Dihydro-5,5,7-trimethyl-8-phenyl-2-naphthanenyl)carbonyl]amino]benzoic acid, methyl ester (I$^3$e)

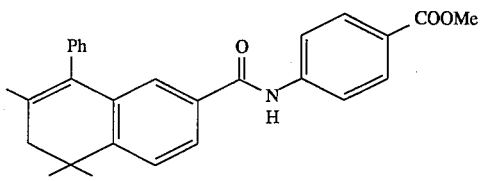

To a solution of acid XVIIIf (171 mg, 0.59 mmol) in 4 mL of methylene chloride was added oxalyl chloride (150 mg, 1.18 mmol) and 1 drop of dimethylformamide at 0° C. The solution was stirred at 0° C. for 1 hour and at room temperature for 16 hours. The solvent was evaporated and the residue was dried in vaccum. To the residue was added methyl p-aminobenzoate (98 mg, 0.65 mmol) and 3 mL of anhydrous pyridine. The mixture was stirred at room temperature for 18 hours. The solvent was evaporated, and the residue was diluted with 1N HCl (20 mL) and extracted with EtOAc (20 mL×3). The combined extracts were dried over maganesium sulfate, filtered, and evaporated. The residue was purified by flash chromatography on silica gel (eluted with hexane: EtOAc, 20:1 to 5:1) to give 149 mg (78% yield) of the title compound as an oil; $^1$H-NMR (CDCl$_3$) δ1.37 (s, 6H), 1.75 (s, 3H), 2.34 (s, 2H), 3.90 (s, 3H), 7.09 (d, J=1.8 Hz, 1H), 7.18 (bd, J=6.8 Hz, 2H); 7.33–7.46 (m, 4H), 7.60 (d, J=8.8 Hz, 2H), 7.65 and 7.67 (d over bs, J=1.9 Hz, 1H), 8.00 (d, J=8.7 Hz, 2H); MS (DCI) m/e: 426 (MH$^{30}$).

EXAMPLE 60

4-[[(5,6-Dihydro-5,5,7-trimethyl-8-phenyl-2-naphthanenyl)carbonyl]amino]benzoic acid (I⁴e)

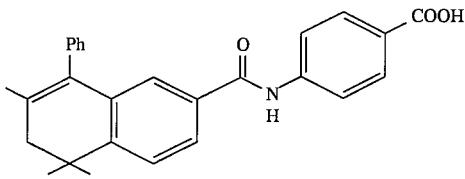

A mixture of compound I³e (97 mg, 0.23 ml) and 2N NaOH (1.15 mL, 2.30 mmol) in 5 mL of tetrahydrofuran and 5 mL of MeOH was stirred at room temperature for 12 hours. The resulting solution was acidified with 1N HCl and concentrated under reduced pressure. The residue was diluted with 10 mL of water and extracted with EtOAc (15 mL×2). The combined extracts were dried over magnesium sulfate, filtered, and evaporated. The residue was triturated with Et₂O-hexane to give 77 mg (82% yield) of the product as white solids; $^1$H-NMR (DMSO-d₆) δ1.33 (s, 6H), 1.69 (s, 3H), 2.31 (s, 2H), 7.02 (s, 1H), 7.15 (d, J=7.9 Hz, 2H), 7.33–7.49 (m, 4H), 7.75 (d, J=8.4 Hz, 1H), 7.79 (d, J=8.6 Hz, 2H), 7.87 (d, J=8.6 Hz, 2H); MS (DCI) m/e: 412 (MH⁺).

Anal. Calcd. for $C_{27}H_{25}NO_3 \cdot 0.25 H_2O$: C, 77.95, H, 6.18; N, 3.37. Found: C, 77.93; H, 6.01; N, 3.27.

EXAMPLE 61

10,10-Dimethyl-9-oxo-5,8,8a,9,10,10a-hexahydroanthracene-2-carboxylic acid, methyl ester (XXX-VIIa)

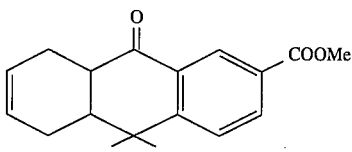

A solution of enone XXXa (500 mg, 2.17 mmol) and aluminum chloride (260 mg, 1.95 mmol) in 10 mL of anhydrous toluene was saturated with 1,3-butadiene at −78° C. After stirring at room temperature for 18 hours, the mixture was diluted with 20 mL of 1N HCl and extracted with EtOAc (30 mL×3). The combined extracts were washed with water (20 mL), saturated sodium chloride and dried over magnesium sulfate. The solvent was evaporated and the residue was purified by flash chromatography on silica gel (eluted with EtOAc:hexane, 1:20 to 1:5) to give 638 mg (quantative yield) of the title product as an oil; $^1$H-NMR (CDCl₃) δ1.45, 1.49 (s, 3H each), 1.60–1.75 (m, 1H), 2.10–2.30 (m, 3H), 2.99–3.06 (bd, J=18 Hz, 1H), 3.29 (bs, 1H), 3.91 (s, 3H), 5.53–5.58 (m, 1H), 5.70–5.76 (m, 1H), 7.46 (d, J=8.2 Hz, 1H), 8.16 (dd, J=1.8, 8.2 Hz, 1H), 8.64 (d, J=1.8 Hz, 1H); MS (DCI) m/e: 285 (MH⁺).

Anal. Calcd. for $C_{18}H_{20}O_3$: C, 76.03, H, 7.09. Found: C, 75.73; H, 7.25.

EXAMPLE 62

10,10-Dimethyl-9-phenyl-5,8,10,10a-tetrahydroanthracene-2-carboxylic acid, methyl ester (XXX-VIIIa)

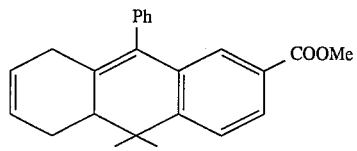

To a solution of compound XXXVIIa (600 mg, 2.11 mmol) in 5 mL of anhydrous tetrahydrofuran was slowly added phenylmagnesium bromide (3.0M in ether, 1.76 mL, 5.28 mmol) at −30° C. After stirring for 15 min, the mixture was slowly warmed to 0° C. in 20 min. The reaction was quenched with saturated ammonium chloride solution (30 mL) and extracted with EtOAc (30 mL×3).

The combined extracts were dried over magnesium sulfate, filtered, and evaporated. The residue was partially purified by flash chromatography on silica gel (eluted with EtOAc:hexane, 1:20 to 1:5) to give 520 mg of a crude alcohol. To the alcohol was added anhydrous benzene (10 mL) and p-toluenesulfonic acid (50 mg). The resulting solution was stirred at reflux for 3 hours. The solvent was evaporated and the residue was purified by flash chromatography on silica gel (eluted with EtOAc:hexane, 1:20 to 1:5) to give 265 mg (36% yield) of the title compound as an oil; $^1$H-NMR (CDCl₃) δ1.34, 1.44 (s, 3H each), 1.92–2.05 (m, 1H), 2.25–2.45 (m, 2H), 2.65–2.80 (m, 2H), 3.78 (s, 3H), 5.55–5.78 (m, 2H), 7.16 (d, J=6.8 Hz, 2H), 7.31 (d, J=1.7 Hz, 1H), 7.30–7.50 (m, 6H), 7.82 (dd, J=1.7, 8.0 Hz, 1H).

EXAMPLE 63

10,10-Dimethyl-9-phenyl-5,8,10,10a-tetrahydroanthracene-2-carboxylic acid (XVIIIg).

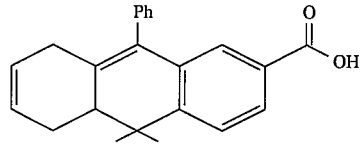

A solution of compound XXXVIIIa (260 mg, 0.75 mmol) and 3N NaOH (2.5 mL, 7.5 mmol) in 10 mL of methanol was stirred at 80° C. for 3 hours. The solvent was evaporated, and the residue was acidified with 1N HCl, extracted with EtOAc (30 mL×3). The combined extracts were washed with water (20 mL), dried over magnesium sulfate, filtered and evaporated to give 235 mg (95% yield) of the title compound; $^1$H-NMR (CDCl₃) δ1.34, 1.44 (s, 3H each), 1.93–2.05 (m, 1H), 2.25–2.37 (m, 1H), 2.41 (dd, J=5.0, 11.9 Hz, 1H), 2.65–2.80 (m, 2H), 5.60–5.70 (m, 2H), 7.14 (d, J=6.7 Hz, 2H), 7.32 (d, J=1.8 Hz, 1H), 7.36–7.46 (m, 4H), 7.85 (dd, J=1.8, 8.0 Hz, 1H); MS (DCI) m/e: 331 (MH⁺).

Anal. Calcd. for $C_{23}H_{22}O_2$: C, 83.61, H, 6.71. Found: C, 83.25; H, 6.86.

EXAMPLE 64

4-[[(5,8,10,10a-Tetrahydro-10,10-dimethyl-9-phenyl-2-anthracenyl)carbonyl]amino]benzoic acid, methyl ester (I³f)

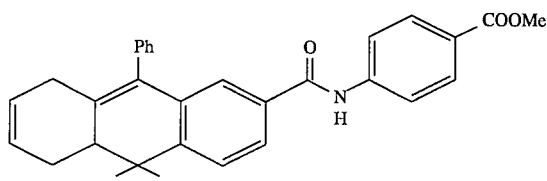

To the solution of acid XVIIIg (225 mg, 0.68 mmol) in 4 mL of methylene chloride was added oxalyl chloride (172 mg, 1.36 mmol) and 1 drop of dimethylformamide at 0° C. The solution was stirred at 0° C. for 2 hour and at room temperature for 1 hour. The solvent was evaporated and the residue was dried in vaccum. To the residue was added methyl p-aminobenzoate (122 mg, 0.81 mmol) and 2 mL of anydrous pyridine. The mixture was stirred at room temperature for 16 hours. The solvent was evaporated, and the residue was diluted with 1N HCl (20 mL) and extracted with EtOAc (30 mL× 3). The combined extracts were dried over maganesium sulfate, filtered, and evaporated. The residue was purified by flash chromatography on silica gel (eluted with hexane:EtOAc, 20:1 to 5:1) to give 210 mg (67% yield) of the title compound; $^1$H-NMR (CDCl$_3$) δ1.36, 1.45 (s, 3H each), 1.95–2.05 (m, 1H), 2.33 (dt, J=4.6, 16.1 Hz, 1H), 2.44 (dd, J=5.1, 12.0 Hz, 1H), 2.65–2.82 (m, 2H), 3.89(s, 3H), 5.60–5.73 (m, 2H), 7.09 (d, J=1.9 Hz, 1H), 7.18 (bd, J=6.7 Hz, 2H), 7.33–7.47 (m, 4H), 7.59–7.65 (m, 3H), 7.70 (bs, 1H), 8.00 (d, J=8.8 Hz, 2H); MS (DCI) m/e: 464 (MH$^+$).

EXAMPLE 65

4-[[(5,8,10,10a-Tetrahydro-10,10-dimethyl-9-phenyl-2-anthracenyl)carbonyl]amino]benzoic acid (I⁴f)

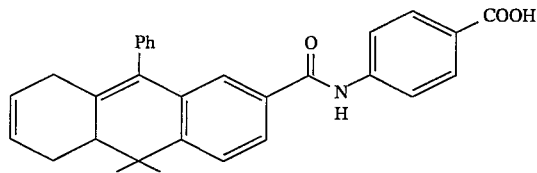

A solution of ester I³f (210 mg, 0.45 mmol) and dibutyltin oxide (228 mg, 0.92 mmol) in 5 mL of anhydrous toluene was stirred at reflux for 2 days. The mixture was added 1N HCl (20 mL) and extracted with EtOAc (20 mL×3). The combined extracts were washed with water (10 mL), and concentrated to approximate 20 mL. The solution was then stirred with 10 mL of 20% potassium fluoride solution for 30 min. The mixture was extracted with EtOAc (20 mL×2). The combined extracts were dried over magnesium sulfate, filtered, and evaporated. The residue was purified by flash chromatography on silica gel (eluted with MeOH: CH$_2$Cl$_2$, 1:100 to 1:5) to give 72 mg (35% yield) of the title product as a yellow solid; $^1$H-NMR (DMSO-d$_6$) δ1.30, 1.41 (s, 3H each), 1.85 (bt, J=12.1 Hz, 1H), 2.28–2.35 (m, 1H), 2.41 (dd, J=5.0, 11.5 Hz, 1H), 2.55 (bd, J=19.1 Hz, 1H), 2.75 (bd, J=19.1 Hz, 1H), 5.60–5.80 (m, 2H), 7.02 (d, J=1.9 Hz, 1H), 7.12 (d, J=6.9 Hz, 2H), 7.35–7.48 (m, 4H), 7.73 (dd, J=1.9, 8.2 Hz, 1H), 7.77 (d, J=8.8 Hz, 2H), 7.86 (d, J=8.8 Hz, 2H), 10.35 (s, 1H); MS (DCI) m/e: 450 (MH$^+$).

Anal. Calcd. for C$_{30}$H$_{27}$NO$_3$·0.75 H$_2$O: C, 77.81, H, 6.20; N, 3.02. Found: C, 78.09; H, 5.99; N, 3.14.

EXAMPLE 66

4,4-Dimethyl-7-iodo-1-tetralone (XXXIX)

To a solution of 4,4-dimethyl-7-amino-1-tetralone (XII) (1.82 g, 10.0 mmol) in concentrated hydrochloric acid (4.69 mL) was added ice cold water (3.13 mL). The reaction mixture was then cooled to 0° C. by use of an ice-salt bath. The reaction mixture was then diazotized by the dropwise addition with stirring of a solution of sodium nitrite (0.76 g, 11.0 mmol) in water (3.13 mL) keeping temperature between 0°–5° C. After stirring for 15 minutes, the reaction mixture was added to a solution of potassium iodide (3.63 g, 21.9 mmol) in water (18.8 mL). After standing for 30 minutes, the dark gum was extracted with ethyl acetate (1×100 mL). The organic phase was then concentrated in vacuo and the residue chromatographed on silica gel (eluted with 5% ethyl acetate in hexane) to give 1.56 g (Y: 54%) of the title product; $^1$H-NMR (CDCl$_3$): δ8.33 (d, J=2.0 Hz, 1H), 7.82 (dd, J=8.3, 2.0 Hz, 1H), 7.17 (d, J=8.4 Hz, 1H), 2.72 (t, J=6.8 Hz, 2H), 2.01 (t, J=6.8 Hz, 2H), 1.37 (s, 6H); MS (DCI) m/e: 301 (MH$^+$).

EXAMPLE 67

Methyl 4-vinylbenzoate

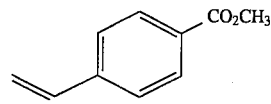

To a solution of 4-vinylbenzoic acid (Aldrich, 2.18 g, 14.7 mmol) in anhydrous acetonitrile (14.0 mL) was added 1.8-diazabicyclo [5.4.0]undec-7-ene (Aldrich, 2.46 g, 16.2 mmol) and iodomethane (Aldrich, 3.13 g, 2.1 mmol) at 0° C. The reaction mixture was then warmed to room temperature and allowed to stir for 3 h. Ethyl acetate (100 mL) was added to the mixture and the solution was washed with brine (50 mL). The organic phase was then separated and concentrated in vacuo. The residue was chromatographed on silica gel (eluted with 5% ethyl acetate in hexane) to give 1.05 g (Y: 44%) of the title product; $^1$H-NMR (CDCl$_3$): δ8.00 (d, J=8.4 Hz, 2H), 7.47 (d, J=8.4 Hz, 2H), 6.76 (m, 1H), 5.87 (d, J=17.6 Hz, 1H), 5.38 (d, J=11.0 Hz, 1H), 3.91 (s, 3H); MS (DCI) m/e: 163 (MH$^+$).

EXAMPLE 68

4-[[(E)-(5,6,7,8-Tetrahydro-5,5-dimethyl-8-oxo)-2-naphthalenyl]vinyl]benzoic acid, methyl ester (XLa)

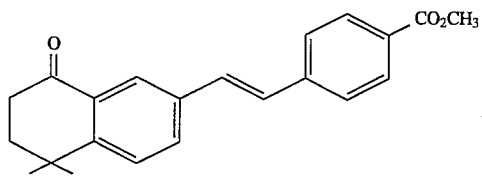

To a solution of 4,4-dimethyl-7-iodo-1-tetralone (XXXIX) (1.55 g, 5.17 mmol) and methyl 4-vinylbenzoate (1.67 g, 10.34 mmol) in dimethylformamide (16.0 mL) was added palladium (II) acetate (Aldrich, 58 mg, 0.259 mmol), tetrabutylammonium chloride hydrate (Aldrich, 1.49 g, 5.17 mmol) and sodium bicarbonate (Mallinckrodt, 1.09 g, 12.9 mmol). The reaction mixture was heated to 70° C. for 4 h and then allowed to stir at room temperature for 16 h. Ethyl acetate (50 mL) was added to the mixture and the solution was washed with brine (50 mL). The organic phase was concentrated in vacuo and the residue chromatographed on silica gel (eluted with 10% ethyl acetate in hexane) to give 1.29 g (Y: 75%) of the title compound; $^1$H-NMR (CDCl$_3$): δ8.19 (d, J=1.7 Hz, 1H), 8.04 (d, J=8.2 Hz, 2H), 6.69 (dd, J=8.1, 1.7 Hz, 1H), 7.57 (d, J=8.2 Hz, 2H), 7.45 (d, J=8.1 Hz, 1H), 7.21 (s, 2H), 3.93 (s, 3H), 2.76 (t, J=6.8 Hz, 2H), 2.05 (t, J=6.8 Hz, 2H), 1.41 (s, 6H); MS (DCI) m/e: 335 (MH$^+$).

EXAMPLE 69

4-[[(E)-(5,6,7,8-Tetrahydro-5,5-dimethyl-8-phenyl-8-hydroxy)-2-naphthalenyl}vinyl]benzoic acid, methyl ester (XLIa).

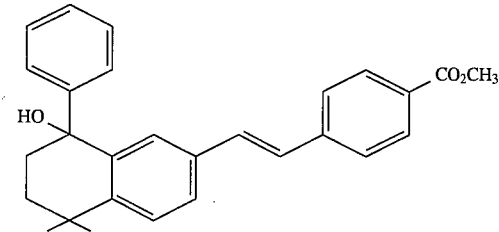

Using the method for the preparation of the 8-phenyl derivative XVIIa, 1.29 g, (3.86 mmol) of compound XLa gave 1.39 g (Y: 87%) of the title compound; $^1$H-NMR (CDCl$_3$): δ7.98 (d, J=8.1 Hz, 2H), 7.48 (m, 5H), 7.31 (s, 5H), 7.03 (m, 2H), 3.91 (s, 3H), 2.22 (m, 2H), 1.85 (m, 1H), 1.60 (m, 1H), 1.40 (s, 3H), 1.35 (s, 3H).

EXAMPLE 70

4-[[(E)-(5,6,-Dihydro-5,5-dimethyl-8-phenyl)-2-naphthalenyl]vinyl]benzoic acid (I$^{11}$a)

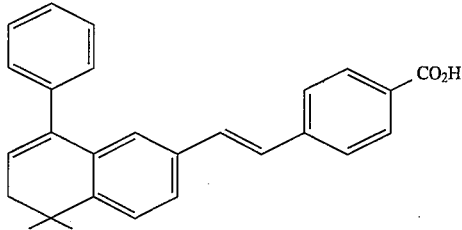

To a solution of compound XLIa (1.38 g, 3.35 mmol) in toluene (20 mL) was added p-toluenesulfonic acid (p-TsOH, 20 mg). After heating at 70° C. for 0.5 h, the reaction mixture was cooled and concentrated in vacuo. The residue was then dissoved in a 1:1 ethyl alcohol tetrahydrofuran solution (20.0 mL) and treated with 10N NaOH (33.7 mmol, 3.37 mL) at room temperature. After 16 hours, an excess of 1N HCl (75 mL) was added and the precipitate collected by vacuum filtration to give 1.23 g (Y: 97%) of the title compound; $^1$H-NMR (DMSO-d$_6$): δ12.87 (s, 1H), 7.85 (d, J=8.4 Hz, 2H), 7.63 (d, J=8.4 Hz, 2H), 7.58 (dd, J=8.1, 1.7 Hz, 1H), 7.47–7.24 (m, 7H), 7.07 (m, 2H), 6.00 (t, J=4.5 Hz, 1H), 2.30 (d, J=4.5 Hz, 2H), 1.28 (s, 6H); $^{13}$C-NMR (DMSO-d$_6$) 167.02, 145.09, 141.35, 140.16, 138.59, 134.22, 133.52, 130.96, 129.66, 129.23, 128.52, 128.33, 127.31, 126.87, 126.65, 126.45, 125.30, 124.69, 124.46, 38.23, 33.29, 27.89; MS (DCI) m/e: 381 (MH$^+$); IR (KBr): 2922, 2818, 1684, 1604 cm$^{-1}$.

Anal. calcd for C$_{27}$H$_{24}$O$_2$•0.65 H$_2$O: C, 82.69; H, 6.50. Found: C, 83.00; H, 6.41.

EXAMPLE 71

4-[[[(5,6,-Dihydro-5,5-dimethyl-8-phenyl)-2-naphthalenyl]carbonyl]sulfamyl]benzoic acid (I$^{12}$a)

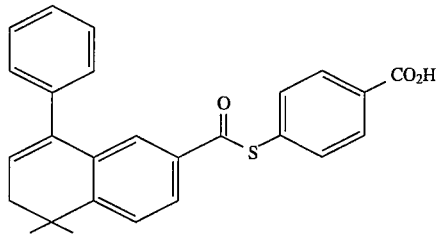

To a solution of compound XVIIIa (119 mg, 0.430 mmol) in anhydrous methylene chloride (5.0 mL) was added oxalyl chloride (0.13 mL, 1.5 mmol) and 2 drops of N,N-dimethylformamide at 0° C. The reaction mixture was allowed to stir at room temperature for 2 hours. The reaction mixture was then concentrated in vacuo. The resultant residue was dissolved in anhydrous pyridine (5.0 mL) to which was added 4-mercaptobenzoic acid (Apin, 66 mg, 0.43 mmol). After 3 hours at room temperature, the mixture was diluted with 1N HCl, extracted with ethyl acetate (50 mL), washed with 1N HCl (3×50 mL) and washed with saturated sodium bicarbonate (2×100 mL). The organic phase was then separated, concentrated in vacuo and the residue chromatographed on silica gel (eluted with 5% methanol in methylene chloride) to give 40 mg (Y: 23%) of the title product; $^1$H-NMR (DMSO): δ7.98 (d, J=8.3 Hz, 2H), 7.91 (dd, J=8.1, 2.0 Hz, 1H), 7.62 (d, J=8.2 Hz, 1H), 7.56 (d, J=8.2 Hz, 2H), 7.48–7.27 (m, 6H), 6.11 (t, J=4.5 Hz, 1H), 2.38 (d, J=4.5 Hz, 2H), 1.33 (s, 6H); MS (DCI) m/e: 415 (MH$^+$); IR (KBr): 3440, 2962, 1684, 1594 cm$^{-1}$.

Anal. calcd for C$_{26}$H$_{22}$O$_3$S$_1$•1.2 H$_2$O: C, 71.60; H, 5.64. Found: C, 71.65, H, 5.44.

EXAMPLE 72

4-[[[(5,6,7,8-Tetrahydro-5,5-dimethyl-8-oxo)-2-naphthalenyl]sulfamyl]carbonyl]benzoic acid, t-butyl ester (XLIVa)

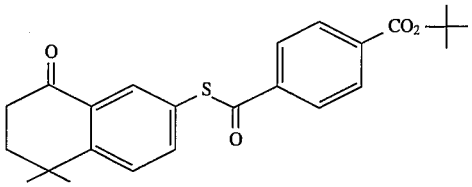

To a solution of mono-tert-butylterephthalate (122 mg, 0.550 mmol) in anhydrous methylene chloride (5.0 mL) was added oxalyl chloride (0.17 mL, 1.95 mmol) and 2 drops of N,N-dimethylformamide at 0° C. After being stirred at room temperature for 2 hours, the mixture was concentrated in vacuo. The residue was dissolved in anhydrous pyridine (5.0 mL) to which was added 4,4-dimethyl-7-mercapto-1-tetralone (XLIII) (113 mg, 0.550 mmol). After 2 hours at room temperature, the mixture was diluted with 1N HCl, extracted with ethyl acetate (50 mL), washed with 1N HCl (3×50 mL) and washed with saturated sodium bicarbonate (2×50 mL). The organic phase was then separated and concentrated in vacuo. The residue was chromatographed on silica gel (eluted with 10% ethyl acetate in hexane) to give 80 mg (Y: 35%) of the title product; $^1$H-NMR (CDCl$_3$): δ8.16 (d, J=1.8 Hz, 1H), 8.11–8.03 (m, 4H), 7.67 (dd, J=8.3, 2.1 Hz, 1H), 7.54 (d, J=8.5 Hz, 1H), 2.77 (t, J=6.8 Hz, 2H), 2.06 (t, J=6.8 Hz, 2H), 1.63 (s, 9H), 1.44 (s, 6H); MS (DCI) m/e: 355 (M-C$_4$H$_9$+H)$^+$.

EXAMPLE 73

4[[[(5,6,7,8-Tetrahydro-5,5-dimethyl-8-phenyl-8-hydroxy)-2-naphthalenyl]sulfamyl]carbonyl]benzoic acid, t-butyl ester (XLVa)

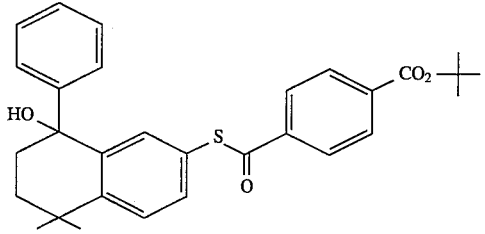

Using the method for the preparation of the 8-phenyl derivative XVIIa, 80 mg (0.19 mmol) of compound XLIVa gave 46 mg (Y: 50%) of the title product; $^1$H-NMR (CDCl$_3$): δ8.03 (m, 4H), 7.52 (d, J=8.2 Hz, 1H), 7.43 (dd, J=8.2, 2.1 Hz, 1H), 7.20 (m, 6H), 2.30–2.10 (m, 3H), 1.90 (m, 1H), 1.63 (s, 9H), 1.45 (s, 3H), 1.37 (s, 3H); MS (DCI) m/e: 471 (MH$^+$).

EXAMPLE 74

4-[[[(5,6-Dihydro-5,5-dimethyl-8-phenyl)-2-naphthalene]sulfamyl]carbonyl]benzoic acid (I$^{13}$a)

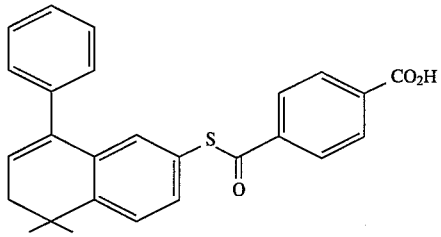

To a solution of compound XLVa (46 mg, 0.094 mmol) in toluene (5.0 mL) was added a few milligrams (~3 mg) of p-toluenesulfonic acid. After being heated at 70° C. for 0.5 h, the reaction mixture was cooled and concentrated in vacuo. The residue was then dissolved in methylene chloride (2.0 mL) to which was added trifluoroacetic acid (0.08 mL) at room temperature. After 16 hours, the reaction mixture was diluted with ethyl acetate (20 mL) and washed with 1N HCl (20 mL). The organic phase was separated, dried over anhydrous magnesium sulfate and concentrated in vacuo to give 34 mg (Y: 87%) of the title product; $^1$H-NMR (DMSO-d$_6$): δ8.03 (m, 4H), 7.53 (d, J=8.1 Hz, 1H), 7.43–7.30 (m, 6H), 6.96 (d, J=1.9 Hz, 1H), 6.07 (t, J=4.5 Hz, 1H), 2.36 (d, J=4.5 Hz, 2H), 1.18 (s, 6H); MS (DCI) m/e: 415 (MH$^+$). IR (KBr): 3432, 2962, 1680, 1202.

Anal. calcd. for C$_{26}$H$_{22}$O$_3$S$_1$•0.35 H$_2$O: C, 74.21; H, 5.44. Found: C, 74.18, H, 5.22.

EXAMPLE 75

4-[[(5,6-Dihydro-5,5-dimethyl-8-phenyl)-2-naphthalenyl]ethyl]benzoic acid, ethyl ester

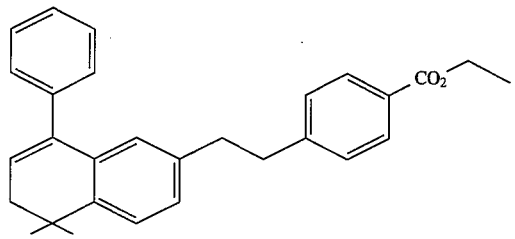

To a stirred solution of compound I$^{15}$a (118 mg, 0.290 mmol) in toluene (7.0 mL) was added 5% palladium on calcium carbonate, poisoned with lead (Aldrich, Lindlar catalyst, 15 mg) at 45 psi of H$_2$. After 16 h, the reaction mixture was filtered through a pad of celite and the filtrate concentrated in vacuo to give 60 mg (Y: 50%) of the title compound; $^1$H-NMR (CDCl$_3$): δ7.93 (d, J=8.1 Hz, 2H), 7.30 (m, 6H), 7.18 (d, J=8.1 Hz, 2H), 7.05 (dd, J=7.9, 1.8 Hz, 1H), 6.81 (d, J=1.8 Hz, 1H), 5.97 (t, J=4.5 Hz, 1H), 4.38 (q, J=7.1 Hz, 2H), 2.84 (m, 4H), 2.34 (d, J=4.5 Hz, 2H), 1.42 (t, J=7.1 Hz, 3H), 1.33 (s, 6H); MS (DCI) m/e: 411 (MH$^+$).

EXAMPLE 76

4-[[(5,6-Dihydro-5,5-dimethyl-8-phenyl)-2-naphthalenyl]ethyl]benzoic acid (I$^{17}$a)

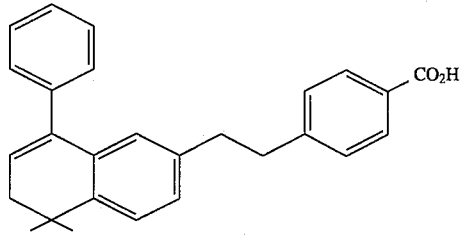

To a solution of compound 4-[[(5,6-dihydro-5,5-dimethyl-8-phenyl)-2-naphthalenyl]ethyl]benzoic acid, ethyl ester (60 mg, 0.146 mmol) in ethyl alcohol (5.0 mL) was added 10N NaOH (2.0 mmol, 0.20 mL). After 1h at 70° C. an excess of 1N HCl (20 mL) was added and the precipitate collected by vacuum filtration to give 59 mg (Y: 99%) of the title product; $^1$H-NMR (DMSO-d$_6$): δ7.79 (d, J=8.2 Hz, 2H), 7.38–7.29 (m, 3H), 7.25 (d, J=8.2 Hz, 2H), 7.21–7.10 (m, 4H), 6.62 (d, J=1.7 Hz, 1H), 5.93 (t, J=4.5 Hz, 1H), 2.78 (m, 4H), 2.25 (d, J=4.5 Hz, 2H), 1.24 (s, 6H). MS (DCI) m/e: 383 (MH$^+$); IR (KBr): 2956, 1688, 1610, 1422 cm$^{-1}$.

Anal. calcd. C$_{27}$H$_{26}$O$_2$: C, 84.78; H, 6.85. Found: C, 84.53; H, 6.81.

EXAMPLE 77

4-[[[(5,6-Dihydro-5,5-dimethyl-8-phenyl-2-naphthalenyl]thiocarbonyl]amino]benzoic acid, methyl ester

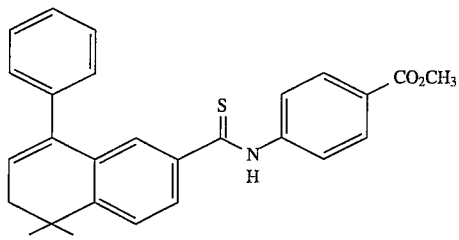

To a solution of compound I³a (285 mg, 0.693 mmol) in tetrahydrofuran (6.0 mL) was added phosphorus pentasulfide (Aldrich, 205 mg, 0.461 mmol). After 0.75 h at reflux, the mixture was concentrated down, diluted with methylene chloride (50 mL) and washed with 5% sodium carbonate (2×50 mL). The organic phase was then concentrated in vacuo and the residue chromatographed on silica gel (eluted with 10% ethyl acetate in hexane) to give 88 mg (Y: 30%) of the title product; $^1$H-NMR (CDCl$_3$): δ8.92 (s, 1H), 8.05 (d, J=8.6 Hz, 2H), 7.74 (dd, J=8.2, 1.8 Hz, 1H), 7.43 (d, J=8.1 Hz, 1H), 7.33 (m, 8H), 6.07 (t, J=4.5 Hz, 1H), 3.92 (s, 3H), 2.38 (d, J=4.5 Hz, 2H), 1.36 (s, 6H); MS (DCI) m/e: 428 (MH$^+$).

EXAMPLE 78

4-[[[(5,6-Dihydro-5,5-dimethyl-8-phenyl)-2-naphthalenyl]thiocarbonyl]amino]benzoic acid (I$^{18}$a)

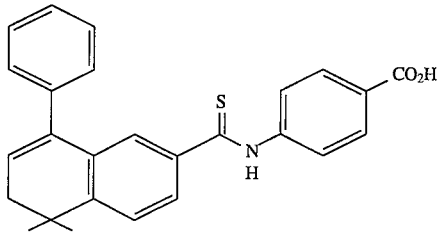

Using the method given for the preparation of the 8-phenyl derivative I⁴a, 80 mg (0.186 mmol) of 4-[[[(5,6-dihydro-5,5-dimethyl-8-phenyl)-2-naphthalenyl]thiocarbonyl]amino]benzoic acid, methyl ester gave 69 mg (Y: 90%) of the title product; $^1$H-NMR (DMSO-d$_6$): δ12.88 (s, 1H), 11.89 (s, 1H), 7.87 (m, 4H), 7.60 (dd, J=8.0, 1.7 Hz, 1H), 7.47 (d, J=8.1 Hz, 1H), 7.35 (m, 6H), 6.07 (t, J=4.5 Hz, 1H), 2.35 (d, J=4.5 Hz, 2H), 1.32 (s, 6H); MS (DCI) m/e: 414 (MH$^+$); IR (KBr): 2922, 1688, 1606, 1514 cm$^{-1}$.

Anal. calcd. for C$_{26}$H$_{23}$O$_2$N$_1$S$_1$·0.5 H$_2$O: C, 73.91; H, 5.73; N, 3.31. Found: C, 73.60; H, 5.76; N, 3.21.

EXAMPLE 79

5,6-Dihydro-5,5-dimethyl-2-[1-(trimethylsilyl)oxy]ethenyl-8-phenylnaphthalene (LVIa)

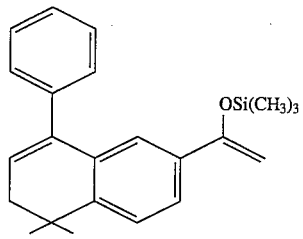

To a solution of compound XIXa of EXAMPLE 32 (2.73 g, 9.89 mmol) in anhydrous methylene chloride (10.0 mL) was added 1,8-diazabicyclo [5.4.0]undec-7-ene (Aldrich, 1.80 g, 11.87 mmol) and chlorotrimethylsilane (1.18 g, 10.9 mmol). The reaction mixture is allowed to reflux gently for 2h and stirred at room temperature for 16 h. Pentane (100 mL) is added to the mixture and the solution is washed with 0.1N HCl (50 mL) and dilute sodium bicarbonate (50 mL). The organic phase is then dried over anhydrous magnesium sulfate and concentrated in vacuo to give 3.17 g (Y: 92%) of the title product; $^1$H-NMR (CDCl$_3$): δ7.45 (dd, J=8.0, 2.0 Hz, 1H), 7.39–7.24 (m, 7H), 5.99 (t, J=4.5 Hz, 1H), 4.74 (d, J=1.6 Hz, 1H), 4.30 (d, J=1.6 Hz, 1H), 2.35 (d, J=4.5 Hz, 2H), 1.34 (s, 6H), 0.14 (s, 9H).

EXAMPLE 80

4-[[[(5,6-Dihydro-5,5-dimethyl-8-phenyl-2-naphthalenyl]carbonyl]methyl]benzoic acid, methyl ester (I$^{22}$a)

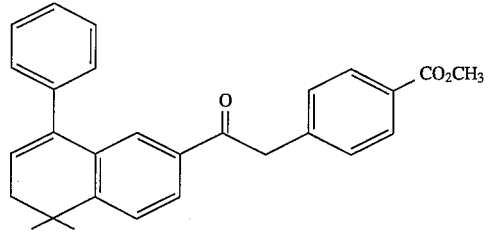

To a solution of compound LVIa (864 mg, 2.48 mmol) and methyl 4-bromobenzoate (Aldrich, 355 mg, 1.65 mmol) in anhydrous benzene (10.0 mL) was added tributyltin fluoride (Aldrich, 806 mg, 2.61 mmol) and PdCl$_2$(P(o-CH$_3$C$_6$H$_4$)$_3$)$_2$ [(59 mg, 0.074 mmol) made from bis(acetonitrile)palladium (II) chloride (Aldrich, 0.074 mmol, 19.3 mg) and tri-o-tolylphosphine (Aldrich, 0.149 mmol, 45.3 mg)]. After 4 h at reflux, the reaction mixture was diluted with ethyl acetate (50 mL) and washed with 1N NaOH (50 mL). The organic phase is then chromatographed on silica gel (eluted with 5% ethyl acetate in hexane) to give 265 mg (Y: 39%) of the title product; $^1$H-NMR (CDCl$_3$): δ7.92 (d, J=8.5 Hz, 2H), 7.87 (dd, J=8.2, 2.0 Hz, 1H), 7.63 (d, J=2.0 Hz, 1H), 7.44 (d, J=8.2 Hz, 1H), 7.41 (m, 3H), 7.29 (m, 2H), 7.17 (d, J=8.0 Hz, 2H), 6.03 (t, J=4.5 Hz, 1H), 4.12 (s, 2H), 3.90 (s, 3H), 2.37 (d, J=4.5 Hz, 2H), 1.35 (s, 6H); MS (DCI) m/e: 411 (MH$^+$).

EXAMPLE 81

4-[[[(5,6-Dihydro-5,5-dimethyl-8-phenyl)-2-naphthalenyl]carbonyl]methyl]benzoic acid (I$^{23}$a)

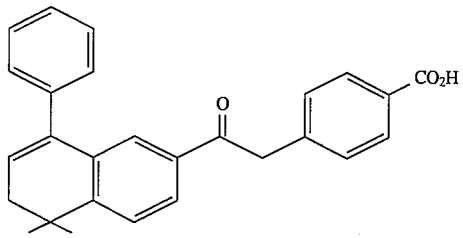

To a solution of compound I$^{22}$a (200 mg, 0.488 mmol) in anhydrous toluene was added dibutyltin oxide (Aldrich, 364 mg, 1.46 mmol). After 16 h at reflux, the reaction mixture was concentrated in vacuo and the residue chromatographed on silica gel (eluted with 5% methanol in methylene chloride) to give 70 mg of impure product (tin by-products present). A second purification by preparative thin layer chromatography afforded 10 mg (Y: 5%) of the title product; $^1$H-NMR (DMSO-d$_6$): δ7.99 (dd, J=7.9, 1.9 Hz, 1H), 7.82 (d, J=8.0 Hz, 2H), 7.54 (d, J=8.0 Hz, 1H), 7.49 (s, 1H), 7.42 (m, 3H), 6.05 (t, J=4.5 Hz, 1H), 4.30 (s, 1H), 4.28 (s, 1H), 2.34 (d, J=4.5 Hz, 2H), 1.31 (s, 6H); MS (DCI) m/e: 397 (MH$^+$); High res. M.S. Calcd.: 397.1804. Found: 397. 1816, 3.0 ppM deviation.

EXAMPLE 82

5,6-Dihydro-5,5-dimethyl-2-hydroxymethyl-8-phenylnaphthalene (LVIIa)

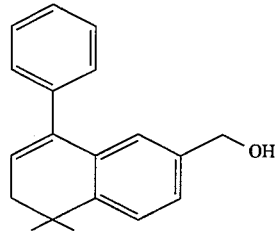

A solution of 95% lithium aluminum hydride powder (LAH, 40 mg, 1.0 mmol) in anhydrous diethyl ether (5.0 mL) was allowed to reflux until most of the hydride dissolved. A solution of compound XVIIIa (485 mg, 1.66 mmol) in anhydrous diethyl ether (5.0 mL) was then slowly added. After 0.5 h, ethyl acetate (20 mL) and 1N hydrochloric acid (20 mL) were added. The organic phase was separated, dried over anhydrous magnesium sulfate and concentrated in vacuo to give 368 mg (Y: 84%) of the title compound; $^1$H-NMR (CDCl$_3$): δ7.36 (m, 6H), 7.26 (m, 1H), 7.02 (d, J=1.8 Hz, 1H), 5.99 (t, J=4.5 Hz, 1H), 4.55 (s, 2H), 2.05 (d, J=4.5 Hz, 2H), 1.34 (s, 6H); MS (DCI) m/e: 247 (M$^+$-OH).

EXAMPLE 83

5,6-Dihydro-5,5-dimethyl-2-bromomethyl-8-phenylnaphthalene (LVIIIa)

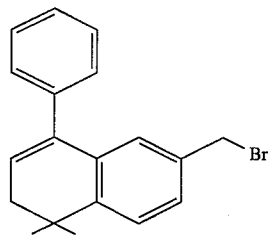

To a solution of carbon tetrabromide (Aldrich, 1.36 g, 4.09 mmol) and triphenylphosphine (Aldrich, 1.07 g, 4.09 mmol) in anhydrous diethyl ether (20 mL) was added compound LVIIa (900 mg, 3.41 mmol). After 16 h at room temperature, the reaction mixture was filtered and the filtrate was concentrated in vacuo. The residue was chromatographed on silica gel (eluted with 3% ethyl acetate in hexane) to give 790 mg (Y: 71%) of the title product; $^1$H-NMR (CDCl$_3$): δ7.39 (m, 6H), 7.27 (dd, J=8.1, 1.8 Hz, 1H), 7.04 (d, J=1.8 Hz, 1H), 6.01 (t, J=4.5 Hz, 1H), 4.39 (S, 2H), 2.35 (d, J=4.5 Hz, 2H), 1.34 (s, 6H); MS (DCI) m/e: 327 (MH$^+$).

EXAMPLE 84

4-[[[(5,6-Dihydro-5,5-dimethyl-8-phenyl)-2-naphthalenyl]methyl]oxy]benzoic acid, ethyl ester (I$^{25}$a)

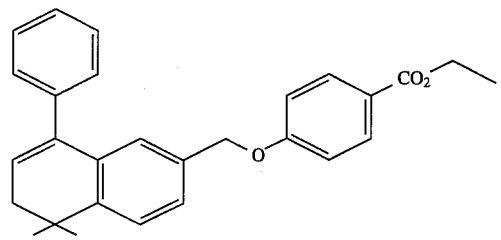

To a solution of ethyl 4-hydroxybenzoate (Aldrich, 152 mg, 0.917 mmol) in ethylene glycol dimethy ether (6.0 mL) was added 60% sodium hydride (1.05 mmol, 43 mg) at room temperature. After 0.15 h, compound LVIIIa (330 mg, 1.01 mmol) was added. After 16 h the reaction mixture was diluted with ethyl acetate (50 mL) and washed with 1N hydrochloric acid (2×50 mL). The organic phase was concentrated in vacuo and the residue chromatographed on silica gel (eluted with 10% ethyl acetate in hexane) to give 64 mg (Y: 17%) of the title product; $^1$H-NMR (CDCl$_3$): δ7.97 (d, J=8.8 Hz, 2H), 7.36 (m, 7H), 7.06 (s, 1H), 6.92 (d, J=8.8 Hz, 2H), 6.01 (t, J=4.5 Hz, 1H), 4.96 (s, 2H), 4.34 (q, J=7.2 Hz, 2H), 2.36 (d, J=4.5 Hz, 2H), 1.40 (t, J=7.2 Hz, 3H), 1.35 (s, 6H); MS (DCI) m/e 413 (MH$^+$).

EXAMPLE 85

4-[[[(5,6-Dihydro-5,5-dimethyl-8-phenyl)-2-naphthalenyl]methyl]oxy]benzoic acid (I$^{26}$a)

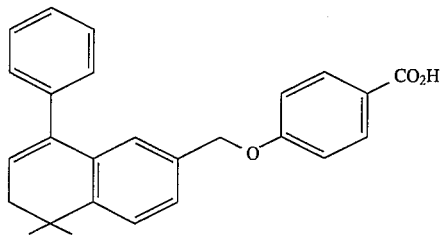

Using the method given for the preparation of the 8-phenyl derivative I$^4$a, 64 mg (0.155 mmol) of compound I$^{25}$a gave 50 mg (Y: 84%) of the title product; $^1$H-NMR (DMSO-d$_6$): δ12.59 (s, 1H), 7.83 (d, J=8.8 Hz, 2H), 7.33 (m, 7H), 6.97 (d, J=8.9 Hz, 2H), 6.96 (s, 1H), 5.99 (t, J=4.5 Hz, 1H), 5.04 (s, 2H), 2.30 (d, J=4.5 Hz, 2H), 1.27 (s, 6H); MS (DCI) m/e: 385 (MH$^+$); IR (KBr): 2958, 1682, 1604, 1252 cm$^{-1}$.

Anal. calcd. for C$_{26}$H$_{24}$O$_3$•0.25 H$_2$O: C, 80.28; H, 6.35. Found: C, 80.41; H, 6.23.

EXAMPLE 86

4-[[[(5,6-Dihydro-5,5-dimethyl-8-phenyl)-2-naphthalenyl]oxy]methyl]benzoic acid (I$^{27}$a)

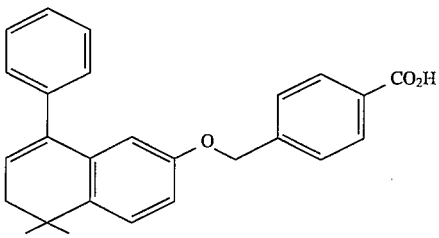

To a solution of compound XXVa OF EXAMPLE 38 (193 mg, 0.772 mmol) in ethylene glycol dimethyl ether (5.0 mL) was added 60% sodium hydride (36 mg, 0.888 mmol) at room temperature. Methyl 4-(bromomethyl)benzoate (Aldrich, 195 mg, 0.848 mmol) was added after 15 minutes. After 16 h at room temperature, 60% sodium hydride (36 mg, 0.888 mmol) was added again. After 24 h. at reflux, the reaction mixture was diluted with ethyl acetate (50 mL) and washed with 1N hydrochloric acid (2×50 mL). The organic phase was concentrated in vacuo and the residue chromatographed on silica gel (eluted with 5% methanol in methylene chloride) to give 170 mg of impure material. The crude material was dissolved in ethyl alcohol (3 mL) and 1N hydrochloric acid (20 mL) was added. The precipitate was collected by vacuum filtration. 50 mg (Y: 16%) of the title product was isolated; $^1$H-NMR (DMSO-d$_6$): δ12.95 (s, 1H), 7.89 (d, J=8.3 Hz, 2H), 7.42 (d, J=8.3 Hz, 2H), 7.39–7.21 (m, 6H), 6.88 (dd, J=8.5,2.7 Hz, 1H), 6.44 (d, J=2.7 Hz, 1H), 5.97 (t, J=4.5 Hz, 1H), 5.04 (s, 2H), 2.27 (d, J=4.5 Hz, 2H), 1.24 (s, 6H); MS (DCI) m/e: 385 (MH$^+$); IR (KBr): 3442, 1682, 1282 cm$^{-1}$.

Anal. calcd. for C$_{26}$H$_{24}$O$_3$•0.5 H$_2$O: C, 80.59; H, 6.50. Found: C, 80.31; H, 6.26.

EXAMPLE 87

5,5-Dimethyl-8-hydroxy-8-(2,4-dimethylphenyl)-5,6,7,8-tetrahydro-naphthalene-2-carboxylic acid, methyl ester (XVIIe)

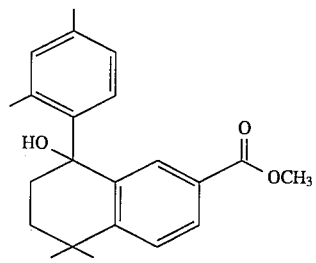

Using the method given for the preparation of the 8-(2-fluorophenyl) derivative XVIId, 311 mg (1.34 mmol) of compound XVIa gave 284 mg (Y: 63%) of the title compound; $^1$H-NMR (CDCl$_3$): δ7.91 (dd, J=8.3, 1.8 Hz, 1H), 7.66 (s, 1H), 7.49 (d, J=8.3 Hz, 2H), 7.02 (d,J=8.0 Hz, 1H), 6.93 (s, 1H), 3.80 (s, 3H), 2.76 (m, 1H), 2.34 (m, 1H), 2.32 (s, 3H), 2.08 (m, 1H), 1.63 (m, 1H), 1.55 (s, 3H), 1.42 (s, 3H), 1.35 (s, 3H); MS (DCI) m/e: 339 (MH$^+$).

EXAMPLE 88

5,5-Dimethyl-5,6-dihydro-8-(2,4-dimethylphenyl)naphthalene-2-carboxylic acid

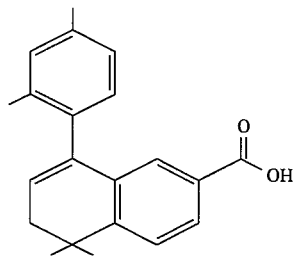

Using the method given for the preparation of 8-phenyl derivative XVIIIe, 311 mg (1.34 mmol) of compound XVIIa gave 285 mg (Y: 63%) of the title product; $^1$H-NMR (CDCl$_3$): δ7.78 (dd, J=8.0, 1.7 Hz, 1H), 7.48 (d, J=8.0 Hz, 1H), 7.18 (d, J=1.6 Hz, 1H), 7.06 (m, 3H), 5.86 (t, J=4.5 Hz, 1H), 2.35 (m, 2H), 2.33 (s, 3H), 1.99 (S, 3H), 1.39 (s, 3H), 1.28 (s, 3H); MS (DCI) m/e: 307 (MH$^+$).

EXAMPLE 89

4-[[[[5,6-Dihydro-5,5-dimethyl-8-(2,4dimethylphenyl)]-2-naphthalenyl]carbonyl]amino]benzoic acid, methyl ester (I$^3$h)

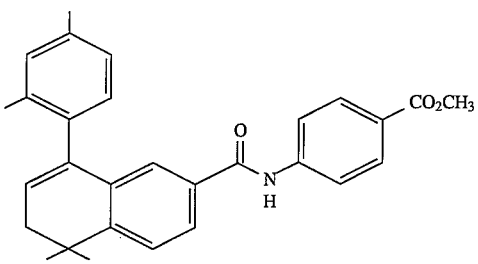

Using the method given for the preparation of the 8-(2-fluorophenyl) derivative I³g, 221 mg (0.722 mmol) of compound XVIIIh gave 67 mg (Y: 21%) of the title product; ¹H-NMR (CDCl³): δ8.00 (d, J=8.7 Hz, 2H), 7.77 (s, 1H), 7.68 (dd, J=8.2, 1.7 Hz, 1H), 7.63 (d, J=8.7 Hz, 2H), 7.47 (d, J=8.0 Hz, 1H), 7.15 (d, J=1.7 Hz, 1H), 7.06 (m, 3H), 5.93 (t, J=4.5 Hz, 1H), 3.90 (s, 3H), 2.43 (m, 2H), 2.36 (s, 3H), 2.08 (s, 3H), 1.45 (s, 3H); MS (DCI) m/e: 440 (MH⁺).

EXAMPLE 90

4-[[[[5,6-Dihydro-5,5-dimethyl-8-(2,4-dimethylphenyl)]-2-naphthalenyl]carbonyl]amino]benzoic acid (I⁴h)

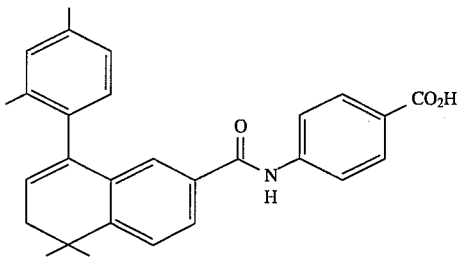

Using the method given for the preparation of the 8-phenyl derivative I⁴a, 67 mg (0.153 mmol) of compound I³h gave 61 mg (Y: 94%) of the title product; ¹H-NMR (DMSO-d₆): δ12.72 (s, 1H), 10.40 (s, 1H), 7.87 (d, J=8.8 Hz, 2H), 7.80 (m, 3H), 7.52 (d, J=8.0 Hz, 1H), 7.04 (m, 4H), 5.88 (t, J=4.5 Hz, 1H), 2.38 (m, 2H), 2.31 (s, 3H), 1.99 (s, 3H), 1.41 (s, 3H), 1.29 (s, 3H); MS (DCI) m/e: 426 (MH⁺); IR (KBr): 2960, 1688, 1594, 1518 cm⁻¹.

Anal. calcd. for $C_{28}H_{27}N_1O_1 \cdot 0.5 H_2O$: C, 77.39; H, 6.50; N, 3.22. Found: C, 77.57; H, 6.50; N, 3.22.

EXAMPLE 91

5,5-Dimethyl-8-hydroxy-(4-methylphenyl)-5,6,7,8-tetrahydro-naphthalene-2-carboxylic acid, methyl ester (XVIIf)

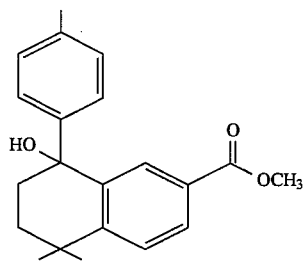

Using the method given for the preparation of the 8-(2-fluorophenyl) derivative XVIId, 260 mg (1.12 mmol) of compound XVIa gave 189 mg (Y: 52%) of the title product; ¹H-NMR (CDCl₃): δ7.92 (dd, J=8.4, 1.7 Hz, 1H), 7.84 (d, J=1.7 Hz, 1H), 7.47 (d, J=8.4 Hz, 1H), 7.10 (s, 4H), 3.82 (s, 3H), 2.34 (s, 3H), 2.18 (m, 2H), 1.80 (m, 1H), 1.60 (m, 1H), 1.39 (s, 3H), 1.34 (s, 3H); MS (DCI) m/e: 325 (MH⁺).

EXAMPLE 92

5,5-Dimethyl-5,6dihydro-8-(4-methylphenyl)naphthalene-2-carboxylic acid (XVIIIi)

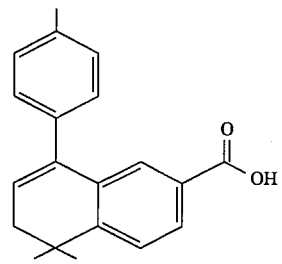

Using the method for the preparation of 8-phenyl derivative XVIIIa, 189 mg (0.583 mmol) of compound XVIIf gave 155 mg (Y: 91%) of the title product; ¹H-NMR (CDCl₃): δ7.81 (dd, J=8.0, 1.7 Hz, 1H), 7.51 (d, J=1.7 Hz, 1H), 7.49 (d, J=8.0 Hz, 1H), 7.23 (m, 4H), 6.00 (t, J=4.5 Hz, 1H), 2.35 (s, 3H), 2.33 (d, J=4.5 Hz, 1H), 1.30 (s, 6H); MS (DCI) m/e: 293 (MH⁺).

EXAMPLE 93

4-[[[[5,6-Dihydro-5,5-dimethyl-8-(4-methylphenyl)]-2-naphthalenyl]carbonyl]amino]benzoic acid, methyl ester (I³i)

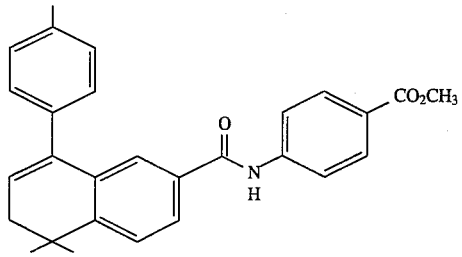

Using the method given for the preparation of the 8-(2-fluorophenyl) derivative I³g, 155 mg (0.531 mmol) of compound XVIIIi gave 143 mg (Y: 63%) of the title product; ¹H-NMR (CDCl₃): δ8.02 (d, J=8.8 Hz, 2H), 7.74 (s, 1H), 7.72 (dd, J=8.0, 1.8 Hz, 1H), 7.66 (d, J=8.8 Hz, 2H), 7.53 (d, J=1.8 Hz, 1H), 7.49 (d, J=8.0 Hz, 1H), 7.23 (m, 4H), 6.06 (t, J=4.5 Hz, 1H), 3.90 (s, 3H), 2.40 (s, 3H), 2.39 (d, J=4.5 Hz, 2H), 1.54 (s, 3H), 1.37 (s, 3H); MS (DCI) m/e: 426 (MH⁺).

EXAMPLE 94

4-[[[[5,6-Dihydro-5,5-dimethyl-8-(4-methylphenyl)]-2-naphthalenyl]carbonyl]amino]benzoic acid (I⁴i)

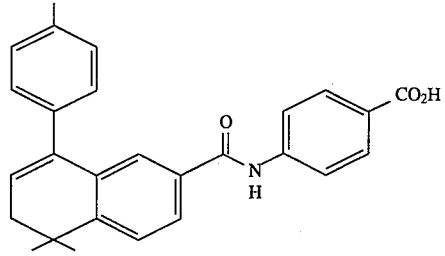

Using the method given for the preparation of the 8-phenyl derivative I⁴a, 143 mg (0.336 mmol) of compound I³i gave 123 mg (Y: 89%) of the title product; 1H-NMR (DMSO-$d_6$): δ12.72 (s, 1H), 10.42 (s, 1H), 7.85 (m, 5H), 7.52 (d, J=8.0 Hz, 1H), 7.44 (d, J=1.8 Hz, 1H), 7.21 (s, 4H), 6.02 (t, J=4.5 Hz, 1H), 2.33 (s, 3H), 2.33 (d, J=4.5 Hz, 2H), 1.31 (s, 6H); $^{13}$C-NMR (DMSO-$d_6$): 166.90, 166.06, 148.77, 143.28, 138.16, 136.93, 136.60, 133.49, 132.48, 130.19, 129.12, 128.21, 126.75, 125.35, 125.03, 123.92, 119.38, 119.29, 37.98, 33.52, 27.75, 20.79; MS (DCI) m/e: 412 (MH⁺); IR (KBr): 2960, 1688, 1594, 1518 cm⁻¹.

Anal. calcd for $C_{27}H_{25}N_1O_3$·0.25 $H_2O$: C, 77.96; H, 6.18, N, 3.37. Found: C, 77.73; H, 6.09; N, 3.29.

EXAMPLE 95

4,4-Dimethyl-7-bromo-1-tetralone (XLVIII)

To a cooled (10° C.) stirred solution of sodium nitrate (2.18 g, 13.92 mmol) in concentrated sulfuric acid (28.4 mL) and glacial acetic acid (26.27 mL) [prepared by adding sodium nitrate to cooled (10° C.) concentrated sulfuric acid, heating to dissolve, recooling and then adding glacial acetic acid] was added a solution of 4,4-dimethyl-7-amino-1-tetralone (XII) (5.0 g, 26.46 mmol) in glacial acetic acid (89 mL) over 10 mintues. The resulting solution was added slowly (over 10 minutes) to a heated (60° C.) solution of copper (I) bromide (16.66 g) in concentrated hydrobromic acid (159 mL). The mixture was warmed to 90° C. for 10 minutes, cooled, diluted with water (250 mL) and extracted with ethyl acetate (2×200 mL). The combined organic phases were concentrated in vacuo and the residue chromatographed on silica gel (eluted with 3% ethyl acetate in hexane) to give 1.95 g (Y: 29%) of the title compound; ¹H-NMR (CDCl₃): δ8.13 (d,J=2.3 Hz, 1H), 7.62 (dd, J=8.5, 2.3 Hz, 1H), 7.31 (d, J=8.5 Hz, 1H), 2.73 (t, J=7.0 Hz, 2H), 2.01 (t, J=7.0 HZ, 2H), 1.38 (s, 6H); MS (DCI) m/e: 253 (MH⁺).

EXAMPLE 96

4,4-Dimethyl-7-trimethylsilanylethynyl-1-tetralone (IL)

To a deaerated solution of compound XLVIII (1.53 g, 6.04 mmol), palladium (II) acetate (Aldrich, 15.4 mg, 0.975 mmol) and triphenylphosphine (31 mg, 0.118 mmol) in anhydrous triethylamine (30 mL) was added (trimethylsilyl)acetylene (Aldrich, 3.0 mL, 21.23 mmol) and heated to 100° C. over 0.5 h. After 4 h at 100° C. the reaction mixture was cooled to room temperature (16 h). The reaction mixture was then filtered and the filtrate concentrated in vacuo. The residue was chromatographed on silica gel (eluted with ethyl acetate in hexane) to give 1.24 g (Y: 76%) of the title product; ¹H-NMR (CDCl₃): δ8.11 (d, J=1.8 Hz, 1H), 7.58 (dd, J=8.2, 1.8 Hz, 1H), 7.36 (d, J=8.2 Hz, 1H), 2.72 (t, J=7.0 Hz, 2H), 2.01 (t, J=7.0 Hz, 2H), 1.37 (s, 6H), 0.24 (s, 9H); MS (DCI) m/e 271 (MH⁺).

EXAMPLE 97

4,4-Dimethyl-7-ethynyl-1-tetralone (L)

To a solution of compound IL (1.24 g, 4.59 mmol), in absolute ethyl alcohol (8.0 mL) was added anhydrous potassium carbonate (170 mg, 1.21 mmol) at room temperature. After 2 h the reaction mixture was concentrated in vacuo, diluted with saturated sodium bicarbonte (25 mL) and extracted with methylene chloride (2×25 mL). The organic phases were combined, concentrated in vacuo and the residue chromatographed on silica gel (eluted with 5% ethyl acetate in hexane) to give 694 mg (Y: 76%) of the title product; ¹H-NMR (CDCl₃): δ8.15 (d, J=1.9 Hz, 1H), 7.62 (dd, J=8.2, 1.9 Hz, 1H), 7.39 (d, J=8.2 Hz, 1H), 3.07 (s, 1H), 2.73 (t, J=7.0 Hz, 2H), 2.02 (t, J=7.0 Hz, 2H), 1.39 (s, 6H); MS (DCI) m/e: 199 (MH⁺).

EXAMPLE 98

4-[[(5,6,7,8-Tetrahydro-5,5-dimethyl-8-oxo)-2-naphthalenyl]ethynyl]benzoic acid, ethyl ester (LIa)

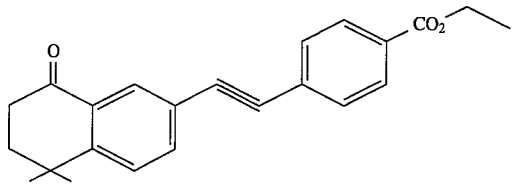

A solution of compound L (153 mg, 0.773 mmol), ethyl 4-iodobenzoate (Lancaster, 160 mg, 0.58 mmol), bis(triphenylphosphine) palladium (II) chloride (Aldrich, 923 mg, 0.013 mmol) and copper (I) iodide (Aldrich, 4.5 mg, 0.02 mmol) in anhydrous triethylamine (3.0 mL) was allowed to stir at room temperature for 2 h. The reaction mixture was diluted with ethyl acetate (25 mL) and washed with water (1×25 mL). The organic phase was concentrated in vacuo and the residue chromatographed on silica gel (eluted with 10% ethyl acetate in hexane) to give 183 mg (Y: 91%) of the title product; ¹H-NMR (CDCl₃): δ8.20 (d, J=1.8 Hz, 1H), 8.04 (d, J=8.3 Hz, 2H), 7.67 (dd, J=8.2, 1.8 Hz, 1H), 7.58 (d, J=8.3 Hz, 2H), 7.44 (d, J=8.2 Hz, 1H), 4.39 (q, J=7.1 Hz, 2H), 2.76 (t, J=6.8 Hz, 2H), 2.04 (t, J=6.8 Hz, 2H), 1.41 (t, J=7.1 Hz, 3H), 1.41 (s, 6H); MS (DCI) m/e: 347 (MH⁺).

EXAMPLE 99

4-[[(5,6,7,8-Tetrahydro-5,5-dimethyl-8-phenyl]-8-hydroxy)-2-naphthalenyl]ethynyl]benzoic acid, ethyl ester (LIIa)

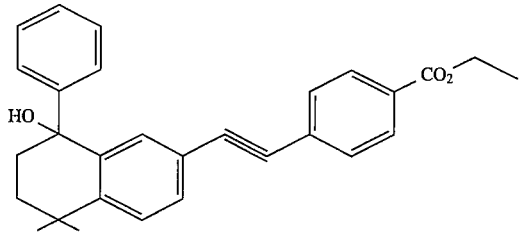

Using the method for the preparation of the 8-phenyl derivative XVIIa, 183 mg (0.529 mmol) of compound LIa gave 177 mg (Y: 79%) of the title compound; ¹H-NMR (CDCl₃): δ7.98 (d, J=8.3 Hz, 2H), 7.50 (d, J=8.3 Hz, 2H), 7.47–7.26 (m, 8H), 4.37 (q, J=7.0 Hz, 2H), 2.20 (m, 2H), 1.89 (m, 1H), 1.60 (m, 1H), 1.41 (s, 6H), 1.39 (t, J=7.0 Hz, 3H); MS (DCI) m/e: 425 (MH⁺).

EXAMPLE 100

4-[[(5,6-Dihydro-5,5-dimethyl-8-phenyl)-2-naphthalenyl]ethynyl]benzoic acid (I¹⁶a)

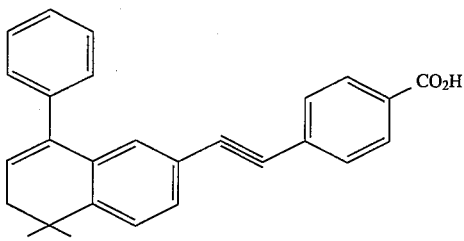

To a solution of compound LIIa (177 mg, 0.42 mmol) was added a few milligrams (~10–20 mg) of p-toluenesulfonic acid. After heating at 70° C. for 0.5 h, the reaction mixture was cooled and concentrated in vacuo to afford 4-[[(5,6-dihydro-5,5-dimethyl-8-phenyl)-2-naphthalenyl]ethynyl] benzoic acid, ethyl ester (I¹⁵a). The residue was then dissolved in ethyl alcohol (5.0 mL) and treated with 10N NaOH (6.5 mmol, 0.65 mL) at 70° C. After 0.5 h, an excess of 1N HCl (20 mL) was added and the precipitate collected by vacuum filtration to give 142 mg (Y: 90%) of the title product; $^1$H-NMR (DMSO-d$_6$): δ13.13 (s, 1H), 7.90 (d, J=8.4 Hz, 2H), 7.58 (d, J=8.4 Hz, 2H), 7.39 (m, 6H), 7.30 (d, J=6.6 Hz, 1H), 6.99 (s, 1H), 6.03 (t, J=4.5 Hz, 1H), 2.33 (d, J=4.5 Hz, 2H), 1.29 (s, 6H); $^{13}$C-NMR (DMSO-d$_6$): 166.64, 146.14, 139.79, 137.96, 133.75, 131.50, 130.98, 130.37, 129.48, 128.63, 128.38, 127.88, 127.60, 127.49, 126.54, 124.69, 119.23, 91.96, 88.11, 37.98, 33.40, 27.75; MS (DCI) m/e: 379 (MH$^+$); IR (KBr): 2958, 1684, 1604, 1420 cm$^{-1}$.

Anal. calcd. for C$_{27}$H$_{22}$O$_2$•0.15 H$_2$O: C, 85.08; H, 5.90. Found: C, 85.06; H, 5.97.

EXAMPLE 101

4,4-Dimethyl-7-[(dimethylamino)thiocarbonyloxy]-1tetralone (XLII)

To a solution of 4,4-dimethyl-7-hydroxy-1-tetralone (XIV) (3.07 g, 16.16 mmol) in water (10.77 mL) containing potassium hydroxide (904 mg) cooled below 10° C. was added N,N-dimethylthiocarbamoyl chloride (2.67 g, 21.6 mmol) in tetrahydrofuran (4.30 mL); the reaction temperature kept below 12° C. After 10 minutes, reaction mixture is made basic by the addition of a 10% aqueous KOH solution (5.39 mL). Product is extracted with ethyl acetate (2×50 mL), organic phases concentrated in vacuo and the residue chromatographed on silica gel (eluted with 10% ethyl acetate in hexane) to give 3.74 g (Y: 84%) of title product; $^1$H-NMR (CDCl$_3$): δ7.68 (d, J=2.6 Hz, 1H), 7.45 (d, J=8.5 Hz, 1H), 7.27 (dd, J=8.5, 2.6 Hz, 1H), 3.46 (s, 3H), 3.34 (s, 3H), 2.73 (t, J=6.8 Hz, 2H), 2.04 (t, J=6.8 Hz, 2H), 1.41 (s, 6H); MS (DCI) m/e: 278 (MH$^+$).

EXAMPLE 102

4,4-Dimethyl-7-mercapto-1-tetralone (XLIII)

Compound XLII (3.74 g 13.50 mmol) under nitrogen with a gas outlet was heated at 270°–275° C. for 0.75 h in a salt bath (1:1 mole mixture of potassium nitrate and sodium nitrite). After cooling, potassium hydroxide (1.13 g) in water (1.35 mL) and ethylene glycol (10.0 mL) was added to the reaction mixture and it was refluxed for 1 h. The cooled reaction mixture was then poured onto ice (30 g). The mixture was washed with methylene chloride (2×50 mL), made acidic with 1N HCl and extracted with methylene chloride (2×50 mL). The organic phase is concentrated in vacuo and the residue chromatographed on silica gel (eluted with 5% ethyl acetate in hexane ) to give 1.22 g (Y: 44% ) of the title product; $^1$H-NMR (CDCl$_3$): δ7.91 (d, J=2.2 Hz, 1H), 7.41 (dd, J=8.2, 2.2 Hz, 1H), 7.30 (d, J=8.2 Hz, 1H), 3.48 (s, 1H), 2.71 (t, J=6.8 Hz, 2H), 2.00 (t, J=6.8 Hz, 2H), 1.37 (s, 6H); MS (DCI) m/e: 207 (MH$^+$).

EXAMPLE 103

4-[[[(5,6,7,8-Tetrahydro-5,5-dimethyl-8-oxo)-2-naphthalenyl]sulfamyl]methyl]benzoic acid, methyl ester (XLVIa)

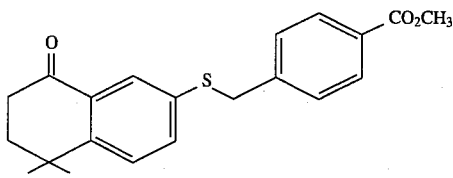

A solution of 4,4-dimethyl-7-mercapto-1-tetralone (XLIII) (262 mg, 1.27 mmol), methyl 4(bromomethyl)benzoate (Aldrich, 291 mg, 1.27 mmol) and diisopropylethylamine (Aldrich, 179 mg, 1.38 mmol) in anhydrous methylene chloride was allowed to stir at room temperature. After 1.5 h the reaction mixture was concentrated in vacuo and the residue chromatographed on silica gel (eluted with 5% ethyl acetate in hexane) to give 402 mg (Y: 89%) of the title product; $^1$H-NMR (CDCl$_3$): δ7.98 (d, J=2.1 Hz, 1H), 7.95 (d, J=8.5 Hz, 2H), 7.38 (dd, J=8.3, 2.1 Hz, 1H), 7.38 (d, J=8.5 Hz, 2H), 7.29 (d,J=8.3 Hz, 1H), 4.17 (s, 2H), 3.90 (s, 3H), 2.71 (t, J=6.8 Hz, 2H), 1.99 (t, J=6.8 Hz, 2H), 1.36 (s, 6H); MS (DCI) m/e: 355 (MH$^+$).

EXAMPLE 104

4-[[[(5,6,7,8-Tetrahydro-5,5-dimethyl-8-phenyl-8-hydroxy)-2-napthalenyl]sulfamyl]methyl benzoic acid, methyl ester (XLVIIa)

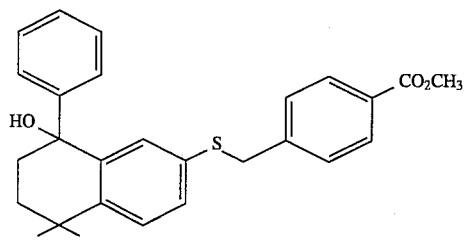

Using the method for the preparation of the 8-phenyl derivative XVIIa, 400 mg (1.13 mmol) of compound XLVIa gave 415 mg (Y: 85%) of the title compound; $^1$H-NMR (CDCl$_3$): δ7.87 (d, J=8.2 Hz, 2H), 7.30–7.18 (m, 9H), 7.02 (d, J=2.0 Hz, 1H), 3.97 (s, 2H), 3.91 (s, 3H), 2.22–2.08 (m, 3H), 1.85 (m, 1H), 1.36 (s, 3H), 1.28 (s, 3H); MS (DCI) m/e: 433 (MH$^+$).

EXAMPLE 105

4-[[[(5,6-Dihydro-5,5-dimethyl-8-phenyl)-2-naphthalenyl]sulfamyl]methyl]benzoic acid (I$^{14}$a)

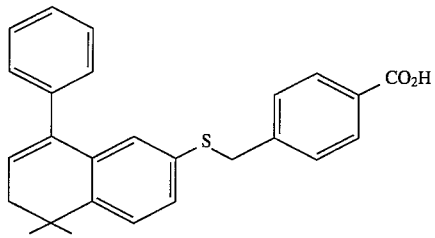

Using the method for the preparation of compound 4-[(E)-(5,6,-dihydro-5,5-dimethyl-8-phenyl-2-naphthalenyl)vinyl]benzoic acid (I$^{11}$a), 415 mg (0.96 mmol) of compound XLVIIa gave 365 mg (Y: 95%) of the title compound; $^1$H-NMR (DMSO-d$_6$): δ12.87 (s, 1H), 7.78 (d, J=8.2 Hz, 2H), 7.37 (m, 3H), 7.29 (s, 1H), 7.25 (d, J=8.2 Hz, 2H), 7.25 (d, J=8.1 Hz, 1H), 7.13 (m, 2H), 6.67 (d, J=1.9 Hz, 1H), 5.95 (t, J=4.5 Hz, 1H), 4.09 (s, 2H), 2.27 (d, J=4.5 Hz, 2H), 1.24 (s, 6H); MS (DCI) m/e: 401 (MH$^+$); IR (KBr): 2956, 1684, 1610, 1422, 1286 cm$^{-1}$.

Anal. calcd. for C$_{26}$H$_{24}$O$_2$S$_1$·0.5 H$_2$O: C, 76.25; H, 6.15. Found: C, 76.20; H, 6.15.

EXAMPLE 106

5,5-Dimethyl-5,6-dihydro-8-phenyl-naphthalene-2-carboxylic acid, N,O-dimethyl hydroxy amide (LIIIa)

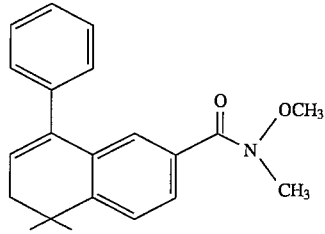

To a solution of compound XVIIIa (1.04 g, 3.74 mmol) in anhydrous methylene chloride (15.0 mL) was added oxalyl chloride (0.39 mL, 4.49 mmol) and 2 drops of N,N-dimethylformamide at 0° C. The reaction mixture was then allowd to stir at room temperature. After 2 hours, N,O-dimethylhydroxylamine hydroxychtoride (Aldrich, 401 mg, 4.11 mmol) and anhydrous pyridine (650 mg, 0.665 mL) were added at 0° C. After 2 hours at room temperature, the reaction mixture was concentrated in vacuo, diluted with ethyl acetate (50 mL) washed with brine (2×50 mL), dried over anhydrous magnesium sulfate and concentrated in vacuo to give 1.13 (Y: 94%) of the title product; $^1$H-NMR (CDCl$_3$): δ7.55 (dd, J=8.0, 1.9 Hz, 1H), 7.39 (d, J=8.0 Hz, 1H), 7.37 (m, 5H), 7.32 (d, J=1.8 Hz, 1H), 6.01 (t, J=4.5 Hz, 1H), 3.49 (s, 3H), 3.27 (s, 3H), 2.37 (d, J=4.5 Hz, 2H), 1,35 (s, 6H); MS (DCI) m/e: 322 (MH$^+$).

EXAMPLE 107

5,5-Dimethyl-5,6-dihydro-2-formyl-8-phenylnaphthalene (LIVa)

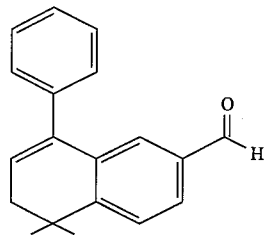

To a solution of compound LIIIa (1.13 g, 3.52 mmol) in tetrahydrofuran (32 mL) at −78° C. was added diisobutylaluminum hydride (DIBAL, 1.0M solution in hexanes, 5.28 mmol, 5.28 mL). After 1 h, the reaction mixture was diluted with 5% HCl in ethyl alcohol (10 mL) and brine (10 mL). Mixture was then extracted with ethyl acetate (2×40 mL). The organic phases were combined, dried over anhydrous magnesium sulfate and concentrated in vacuo to give 720 mg (Y: 78%) of the title product; $^1$H NMR (CDCl$_3$): δ9.86 (s, 1H), 7.76 (dd, J=8.0, 1.7 Hz, 1H), 7.54–7.52 (m, 2H), 7.52–7.26 (m, 5H), 6.07 (t, J=4.5 Hz, 1H), 2.40 (d, J=4.5 Hz, 2H), 1.38 (s, 6H); MS (DCI) m/e: 263 (MH$^+$).

EXAMPLE 108

4-[[[(5,6-Dihydro-5,5-dimethyl-8-phenyl)-2-naphthalenyl]methyl]amino]benzoic acid, methyl ester (I$^{20}$a)

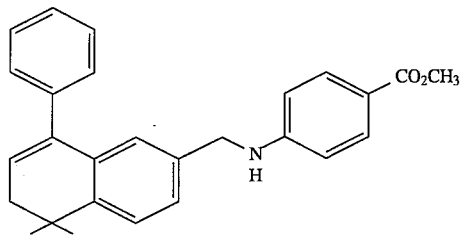

To a solution of methyl 4-aminobenzoate (505 mg, 3.35 mmol) in a 1% glacial acetic acid methyl alcohol solution (6.0 mL) was added LIVa (720 mg, 2.75 mmol) in a 1% glacial acetic acid methyl alcohol solution (6.0 mL). Sodium cyanoborohydride (174 mg, 2.75 mmol) was then added over an one hour period (6×29 mg portions every 10 minutes). After 16 h at room temperature, the reaction mixture was concentrated in vacuo and the residue chromatographed on silica gel (eluted with 10% ethyl acetate in hexane) to give 856 mg (Y: 78%) of the title product; $^1$H-NMR (CDCl$_3$): δ7.83 (d, J=8.9 Hz, 2H), 7.34 (m, 6H), 7.21 (dd, J=7.8, 2.0 Hz, 1H), 6.99 (d, J=2.0 Hz, 1H), 6.52 (d, J=8.9 Hz, 2H), 5.99 (t, J=4.5 Hz, 1H), 4.37 (m, 1H), 4.23 (d, J=5.5 Hz, 2H), 3.84 (s, 3H), 2.35 (t, J=4.5 Hz, 2H), 1.34 (s, 6H); MS (DCI) m/e: 398 (MH$^+$).

EXAMPLE 109

4-[[(5,6-Dihydro-5,5-dimethyl-8-phenyl)-2-naphthalenyl]methyl]amino]benzoic acid, hydrochloride (I²¹a)

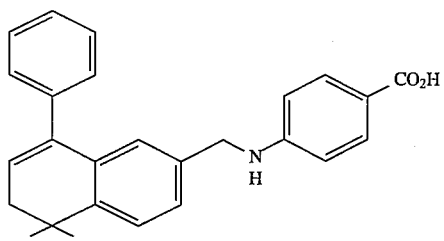

To a solution of compound I²⁰a (197 mg, 0.496 mmol) in ethyl alcohol (5.0 mL) was added 10N NaOH (22.0 mmol, 2.2 mL). After 4 h at reflux, an excess of 1N HCl (40 mL) was added and the precipitate collected by vacuum filtration to give 175 mg (Y: 92%) of the title product; ¹H-NMR (DMSO-$d_6$): δ7.60 (d, J=8.8 Hz, 2H), 7.32 (m, 4H), 7.20 (m, 3H), 6.90 (d, J=1.6 Hz, 1H), 6.49 (d, J=8.8 Hz, 2H), 5.96 (t, J=4.5 Hz, 1H), 4.16 (s, 2H), 2.27 (d, J=4.5 Hz, 2H), 1.24 (s, 6H); MS (DCI) m/e: 384 (MH⁺); IR (KBr): 3418, 2960, 1672, 1602, 1176 cm⁻¹.

Anal. calcd. for $C_{26}H_{25}O_2N_1 \cdot 1.0$ HCl: C, 74.36; H, 6.24; N, 3.34. Found: C, 74.39; H, 6.19; N, 3.29.

EXAMPLE 110

4-[[[(5,6-Dihydro-5,5-dimethyl-8-phenyl)-2-naphthalenyl]amino]thiocarbonyl]benzoic acid, methyl ester

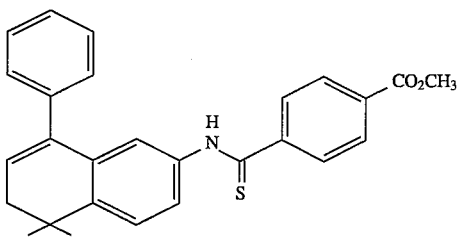

Using the method given for the preparation of 4-[[[(5,6-dihydro-5,5-dimethyl-8-phenyl)-2-naphthalenyl]thiocarbonyl]amino]benzoic acid, methyl ester, 190 mg (0.462 mmol) of compound I¹c gave 104 mg (Y: 52%) of the title product; ¹H-NMR (CDCl₃): δ8.84 (s, 1H), 8.05 (d, J=8.2 Hz, 2H), 7.91 (dd, J=8.8, 2.4 Hz, 1H), 7.81 (d, J=8.2Hz, 2H), 7.44 (d, J=8.8 Hz, 1H), 7.35 (m, 5H), 7.13 (d, J=2.4 Hz, 1H), 6.04 (t, J=4.5 Hz, 1H), 3.94 (s, 3H), 2.38 (d, J=4.5 Hz, 2H), 1.35 (s, 6H); MS (DCI) m/e: 428 (MH⁺).

EXAMPLE 111

4-[[[(5,6-Dihydro-5,5-dimethyl-8-phenyl)-2-naphthalenyl]amino]thiocarbonyl]benzoic acid (I¹⁹a)

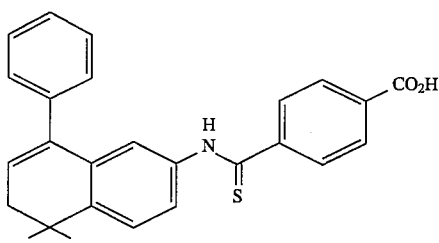

Using the method given for the preparation of the 8-phenyl derivative I⁴a, 104 mg (0.240 mmol) of compound 4-[[[(5,6-dihydro-5,5-dimethyl-8-phenyl)-2-naphthalenyl]amino]thiocarbonyl]benzoic acid, methyl ester gave 80 mg (Y: 80%) of the title product; ¹H-NMR (DMSO-$d_6$): δ11.80 (s, 1H), 7.93 (d, J=8.4 Hz, 2H), 7.77 (d, J=8.4 Hz, 2H), 7.75 (s, 1H), 7.43 (d, J=8.4 Hz, 1H), 7.34 (m, 6H), 6.02 (t, J=4.5 Hz, 1H), 2.33 (d, J=4.5 Hz, 2H), 1.30 (s, 6H); MS (DCI) m/e: 414 (MH⁺); IR (KBr): 2958, 1694, 1490, 1410 cm⁻¹.

Anal. calcd for $C_{26}H_{23}O_2N_1S_1 \cdot 0.5$ H₂O: C, 73.91; H, 5.73, N, 3.31. Found: C, 73.78,; H, 5.55; N, 3.22.

EXAMPLE 112

Methyl 4-mercaptobenzoate

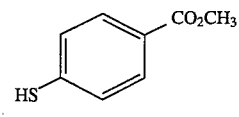

To a solution of 4-mercaptobenzoic acid (Apin, 1.72 g, 11.17 mmol) in anhydrous methyl alcohol (20.0 mL) was added concentrated sulfuric acid (0.43 mL). The reaction mixture is then warmed to reflux for 16 h, concentrated in vacuo, diluted with ethyl acetate (100 mL) and washed with saturated sodium bicarbonate (2×100 mL). The organic phase is then separated, dried over anhydrous magnesium sulfate and concentrated in vacuo to give 712 mg (Y: 38%) of the title product; ¹H-NMR (CDCl₃): δ7.89 (d, J=8.7 Hz, 2H), 7.29 (d, J=8.7 Hz, 2H), 3.90 (s, 3H), 3.60 (s, 1H).

EXAMPLE 113

4-[[[(5,6-Dihydro-5-5-dimethyl-8-phenyl)-2-napthalenyl]methyl]sulfamyl]benzoic acid, methyl ester (I²⁴a)

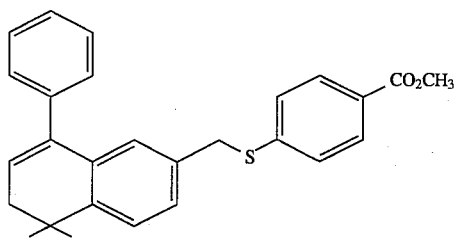

To a solution of methyl 4-mercaptobenzoate (89 mg, 0.528 mmol) in ethylene glycol dimethyl ether (3.0 mL) was added 60% sodium hydride (0.607 mmol, 24 mg) at room temperature. After 0.15 h compound LVIIIa (190 mg, 0.581 mmol) was added. After 2 h the reaction mixture was diluted with ethyl acetate (50 mL) and washed with 1N hydrochloric acid (2×50 mL). The organic phase was concentrated in vacuo and the residue chromatographed on silica gel (eluted with 10% ethyl acetate in hexane) to give 30 mg (Y: 13%) of the title product; $^1$H-NMR (CDCl$_3$): δ7.88 (d, J=8.5 Hz, 2H), 7.28 (m, 9H), 6.98 (d, J=1.4 Hz, 1H), 5.98 (t, J=4.5 Hz, 1H), 4.07 (s, 2H), 3.90 (s, 3H), 2.33 (d, J=4.5 Hz, 2H), 1.32 (s, 6H); MS (DCI) m/e: 415 (MH$^+$).

EXAMPLE 114

4-[[[(5,6-Dihydro-5,5-dimethyl-8-phenyl)-2-napthalenyl]methyl]sulfamyl]benzoic acid (I$^{34}$a)

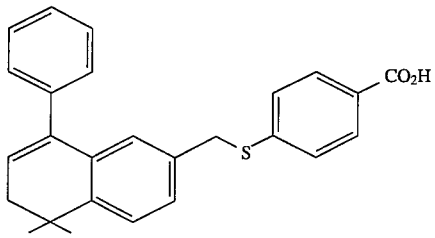

Using the method given for the preparation of the 8-phenyl derivative I$^4$a, 30 mg (0.07 mmol) of compound I$^{24}$a gave 21 mg (Y: 72%) of the title product; $^1$H-NMR (DMSO-d$_6$): δ12.87 (s, 1H), 7.77 (d, J=8.5 Hz, 2H), 7.35 (m, 7H), 7.28 (d, J=1.8 Hz, 1H), 7.19 (dd, J=7.9, 1.8 Hz, 1H), 6.90 (d, J=1.5 Hz, 1H), 5.95 (t, J=4.5 Hz, 1H), 4.19 (s, 2H), 2.27 (d, J=4.5 Hz, 2H), 1.24 (s, 6H); MS (DCI) m/e: 401 (MH$^+$); IR (KBr): 3436, 2960, 1688, 1592 cm$^{-1}$.

Anal. calcd. for C$_{26}$H$_{24}$O$_2$S$_1$·H$_2$O: C, 76.93; H, 6.11. Found: C, 76.91; H, 6.03.

EXAMPLE 115

1,2-Dihydro-1,1-dimethyl-6-nitro-8-(trifluoromethanesulfonyloxy)naphthalene (LXI)

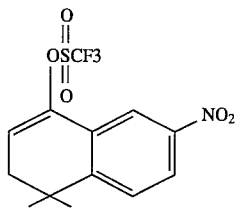

To a solution of 4,4-dimethyl-7-nitro-1-tetralone (VI) (2.4 g, 10.96 mmol) in tetrahydrofuran (10 mL) at −78° C. was added lithium bis(trimethylsilyl)amide (1.0M solution in hexane, 12.05 mmol, 12.05 mL) and then N-(2-pyridyl)triflimide (12.05 mmol, 4.30 g) at −78° C. After 0.5 h at −78° C. the reaction mixture was diluted with water and extracted with ethyl acetate (2×50 mL). The organic phases were combined and concentrated in vacuo. The residue was chromatographed on silica gel (eluted with 5% ethyl acetate in hexane) to give 2.68 g (Y: 70%) of the title product; $^1$H-NMR (CDCl$_3$): δ8.20 (m, 2H), 7.49 (d, J=8.2 Hz, 1H), 6.15 (t, J=4.5 Hz, 1H), 2.50 (d, J=4.5 Hz, 2H), 1.37 (s, 6H); MS (DCI) m/e: 352 (MH$^+$).

EXAMPLE 116

1,2-Dihydro-1,1-dimethyl-6-nitro-4-phenylnaphthalene (LXIIa)

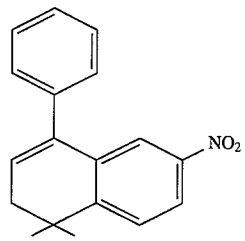

To a solution of compound LXI (2.68 g, 7.64 mmol) in anhydrous 1-methyl-2-pyrolidinone (30.0 ml) was added triphenylarsine (442 mg, 1.44 mmol), tris(dibenzylideneacetone)dipalladium (0) (217 mg, 0.237 mmol) and tributylphenyltin (6.17 g, 16.78 mmol) in anhydrous 1-methyl-2-pyrrolidinone (5.0 ml). After 16 h. at 60° C. the mixture was diluted with water and extracted with ethyl acetate (2×100 ml). The organic phases were combined, stirred over a saturated aqueous solution of potassium fluoride for 0.5 h., separated and concentrated in vacuo. The residue was chromatographed on silica gel (eluted with 20% ethyl acetate in hexane) to give 1.93 g (Y: 90%) of the title product; $^1$H-NMR (CDCl$_3$): δ8.07 (dd, J=8.5, 2.5 Hz, 1H), 7.87 (d, J=2.5 Hz, 1H), 7.50 (d, J=8.5 Hz, 1H), 7.36 (m, 5H), 6.12 (t, J=4.5 Hz, 1H), 2.41 (d, J=4.5 Hz, 2H), 1.39 (s, 6H); MS (DCI) m/e: 280 (MH$^+$).

EXAMPLE 117

5,5-Dimethyl-8-phenyl-5,6-dihydro-naphthalene-2-ylamine (LXIIIa)

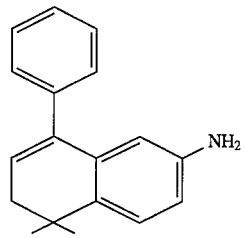

To a solution of compound LXIIa (1.75 g, 6.27 mmol) in benzene (15 mL) was added ferric chloride (33%, 2.94 mL) and water (11.9 mL). The reaction mixture was heated to reflux and iron (3.50 g) was added over a period of 1.5 h in four equal aliquots. The resulting mixture was then refluxed for 16 h. After cooling to room temperature, the reaction mxiture was filtered through a pad of celite. The organic phase was separated, dried over anhydrous magnesium sulfate and concentrated in vacuo to give 1.56 g (Y: 99%) of the title product; $^1$H-NMR (CDCl$_3$): δ7.35 (m, 5H), 7.15 (d, J=8.1 Hz, 1H), 6.57 (dd, J=8.1, 2.5 Hz, 1H), 6.37 (d, J=2.5 Hz, 1H), 5.95 (t, J=4.5 Hz, 1H), 3.45 (bs, 2H), 2.31 (d, J=4.5 Hz, 2H), 1.30 (s, 6H); MS (DCI) me/: 250 (MH$^+$).

EXAMPLE 118

4-[[[(5,6-Dihydro-5-5-dimethyl-8-phenyl)-2-naphthalenyl]amino]methyl]benzoic acid, methyl ester (I[28]a)

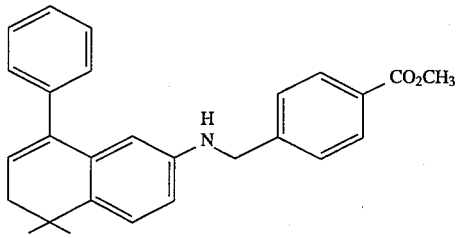

Using the method for the preparation of 4-[[[(5,6-dihydro-5,5-dimethyl-8-phenyl)-2naphthalenyl]methyl]amino]benzoic acid, methyl ester (I[20]a), 1.35 g (5.38 mmol) of compound LXIIIa and methyl 4-formylbenzoate (Aldrich, 723 mg, 4.41 mmol) gave 1.38 g (Y: 79%) of the title product; $^1$H-NMR (CDCl$_3$): δ7.95 (d, J=8.5 Hz, 2H). 7.29 (m, 7H), 7.16 (d, J=8.3 Hz, 1H), 6.47 (dd, J=8.3, 2.6 Hz, 1H), 6.29 (d, J=2.6 Hz, 1H), 5.94 (t, J=4.5, 1H), 4.53 (s, 2H), 3.91 (s, 3H), 2.30 (d, J=4.5 Hz, 2H), 1.29 (s, 6H); MS (DCI) m/e: 398 (MH$^+$).

EXAMPLE 119

4-[[[(5,6-Dihydro-5,5-dimethyl-8-phenyl)-2-naphthalenyl]amino]methyl]benzoic acid (I[29]a)

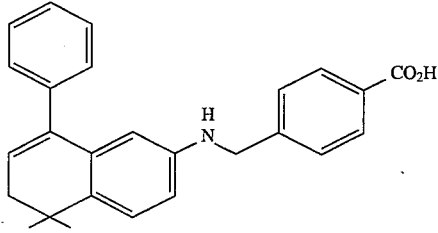

To a solution of compound I[28]a (1.38 g, 3.48 mmol) in a 1:1 mixutre of ethyl alcohol/tetrahydrofuran (15.0 mL) was added 10N NaOH (35.0 mmol, 3.5 mL) at room temperature. After 16 h an excess of 1N HCl (100 mL) was added and the precipitate collected by vacuum filtration to give 1.28 g (Y: 96%) of the title product as a hydrochloride salt; $^1$H-NMR (DMSO-d$_6$): δ7.84 (d, J=8.2 Hz, 2H), 7.36 (d, J=8.2 Hz, 1H), 7.31 (m, 5H), 7.15 (m, 4H), 6.99 (bs, 1H), 6.36 (bs, 1H), 5.90 (t, J=4.5 Hz, 1H), 4.32 (s, 2H), 2.21 (d, J=0.5 Hz, 2H), 1.19 (s, 6H); MS (DCI) m/e: 384 (MH$^+$); IR (KBr): 3420, 2958, 1694, 1606 cm$^{-1}$.

Anal. calcd. for C$_{26}$H$_{25}$N$_1$O$_2$•1.0 HCl: C, 72.80; H, 6.34; N, 3.27. Found: C, 72.98; H, 6.09; N, 3.14.

EXAMPLE 120

3,3-Dimethyl-6-nitro-indan-1-one

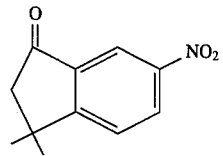

To a solution of 3,3-dimethylindan-1-one (LXIV) (16.3 g, 50.9 mmol) (Harms, W. M. and Eisenbraum, E. *J. Org. Prep. Proc. Int.* 1972, 4, 67–72) in 56 mL of sulfuric acid was slowly added 4.18 mL of 70% nitric acid in 20 mL of sulfuric acid at 0°–5° C. After being stirred for 1 hour, the reaction mixture was poured into 600 g of ice. The precipitates was filtered and washed with water. The solids collected were dissolved in 600 mL of ethyl acetate and washed with NaHCO$_3$ (80 mL×2), dried over magnesium sulfate, and evaporated. The residue was triturated with methanol to give 22.2 g of the title compound as yellow solids; $^1$H-NMR (CDCl$_3$) δ1.49 (s, 6H), 2.71 (s, 2H), 7.68 (d, J=8.4 Hz, 1H), 8.48 (dd, J=2.0, 8.4 Hz, 1H), 8.53 (d, J=2.0 Hz, 1H); MS m/e 206 (MH$^+$).

Anal. calcd. for C$_{11}$H$_{11}$NO$_3$: C, 64.38; H, 5.40; N, 6.83. Found: C, 64.33; H, 5.33; N, 6.86.

EXAMPLE 121

6-Amino-3,3-dimethyl-indan-1-one (LXV)

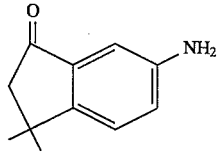

3,3-Dimethyl-6-nitro-indan-1-one (22.2 g, 54.1 mmol) and platinum oxide (0.44 g, 1.94 mmol) in 30 mL of ethyl acetate and 60 mL of methanol was hydrogenated on a Parr Shaker for 40 min. The mixture was filtered through a pad of celite. The filtrate was evaporated and the residue was triturated with hexane to give 18.4 g (97% yield) of the title product as yellow solids; $^1$H-NMR (CDCl$_3$) δ1.38 (s, 6H), 2.56 (s, 2H), 6.98 (d, J=2.3 Hz, 1H), 7.02 (dd, J=2.3, 8.2 Hz, 1H), 7.30 (d, J=8.2 Hz, 1H); MS m/e 176 (MH$^+$).

Anal. calcd. for C$_{11}$H$_{11}$NO$_3$: C, 75.40; H, 7.48; N, 7.99. Found: C, 75.07; H, 7.45; N, 7.94.

EXAMPLE 122

6-Hydroxy-3,3-dimethyl-indan-1-one (LXVI)

A solution of sodium nitrite (14.8 g, 214 mmol) in 30 mL of water was slowly added to the solution of 6-amino-3,3-dimethyl-indan-1-one (14.0 g, 85.8 mmol) in 30 mL of 48% tetrafluoroboric acid and 30 mL of water at 0°–5° C. After being stirred for 30 min, the mixture was filtered, and the solids were washed with cold 5% tetrafluoroboric acid and dried in vacuum. The solids were then added in several portions into a boiling solution of 50 mL of sulfuric acid in 0.5 liter of water. After refluxing for 1 hour, the solution was cooled to room temperature and extracted with ethyl acetate (100 mL×3). The combined extracts were dried over magnesium sulfate and evaporated. The residue was purified by flash chromatography (EtOAc:hexane=1:10 to 1:2) to give 7.60 g (50% yield) of the title compound as a solid; ¹H-NMR (CDCl₃) δ1.40 (s, 6H), 2.64 (s, 2H), 7.13 (s, 1H),7.18 (d, J=8.2 Hz, 1H), 7.39 (d, J=8.2 Hz, 1H); MS m/e 177 (MH⁺).

Anal. calcd. for $C_{11}H_{12}O_2$: C, 74.98; H, 6.86. Found: C, 74.81; H, 6.76.

EXAMPLE 123

Trifluoromethanesulfonic acid 1,1-dimethyl-3-oxo-indan-5-yl ester

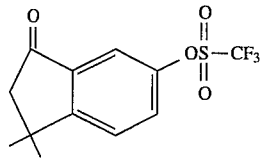

To a solution of 6-hydroxy-3,3-dimethyl-indan-1-one (4.01 g, 24.4 mmol) and 4-dimethylaminopyridine (DMAP, 5.97 g, 48.9 mmol) in 30 mL of methylene chloride was slowly added triflic acid anhydride (9.65 g, 34.2 mmol) at −78° C. After stirring at room temperature for 1 hour, the mixture was diluted with methylene chloride (60 mL), washed with 1N HCl (10 mL×2) and water (10 mL), dried over magnesium sulfate, and evaporated. The residue was purified by flash chromatography (EtOAc:hexane=1:10 to 1:5) to give 5.58 g (74% yield) of the title compound; ¹H-NMR (CDCl₃) δ1.46 (s, 6H), 2.67 (s, 2H), 7.51 (dd, J=2.3, 8.4 Hz, 1H), 7.57 (d, J=2.3 Hz, 1H), 7.60 (d, J=8.4 Hz, 1H); MS m/e 309 (MH⁺).

Anal. calcd. for $C_{12}H_{11}F_3O_4S$: C,46.75; H, 3.60. Found: C, 46.83; H, 3.58.

EXAMPLE 124

Methyl 1,1-dimethyl-3-oxo-indan-5-carboxylate (LXVII)

A solution of trifluoromethanesulfonic acid 1,1-dimethyl-3-oxo-indan-5-yl ester (3.08 g, 10.0 mmol), triethylamine (2.02 g, 20.0 mmol), palladium acetate (0.11 g, 0.50 mmol) and 1,3bis(diphenylphosphino)propane (dppp, 0.21 g, 0.50 mmol) in 30 mL of anhydrous dimethylsulfoxide and 20 mL of methanol was saturated with carbon monoxide for 10 min, and then stirred under a balloon filled with carbon monoxide at 65°–70° C. for 2 hours. Methanol was evaporated, and the resulting solution was diluted with 50 mL of water, extracted with ethyl ether (40 mL× 4). The combined extracts were dried over magnesium sulfate and evaporated, The residue was purified by flash chromatography (EtOAc:hexane=1:20 to 1:5) to give 1.98 g (91% yield) of the title compound as light yellow solids; ¹H-NMR (CDCl₃) δ1.45 (s, 6H), 2.65 (s, 2H), 3.94 (s, 3H), 7.58 (dd, J=8.1 Hz, 1 H), 8.30 (dd, J=1.6, 8.1 Hz, 1H), 8.36 (d, J=1.6 Hz, 1H); MS m/e 219 (MH⁺).

Anal. calcd. for $C_{13}H_{14}O_3$: C, 71.54; H, 6.47, Found: C, 71.71; H, 6.46.

EXAMPLE 125

Methyl 1,1-dimethyl-3-(trifluoromethanesulfonyloxy)-1H-indene-5-carboxylate

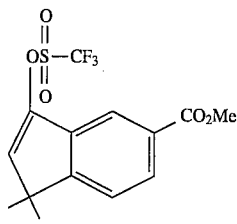

To a solution of methyl 1,1-dimethyl-3-oxo-indan-5-carboxylate (0.90 g, 4.12 mmol) and 2,6-di-tert-butyl-4-methylpyridine (1.10 mg, 5.36 mmol) in 10 mL of methylene chloride was added triflic acid anhydride (1.39 g, 4.94 mmol) at −78° C. After being stirred at room temperature for 16 hours, the mixture was diluted with 70 mL of ethyl ether, washed with 1N HCl (20 mL), dried over magnesium sulfate, and evaporated. The residue was purified by flash chromatography (EtOAc:hexane=1:20 to 1:5) to give 1.23 g (85% yield) of the title compound; ¹H NMR (CDCl₃) δ1.41 (s, 6H),3.95 (s, 3H), 6.30 (s, 1H), 7.44 (d, J=7.8 Hz, 1H), 7.99 (s, 1H), 8.06 (d, J=7.8 Hz, 1H); MS m/e 351 (MH⁺).

EXAMPLE 126

Methyl 1,1-dimethyl-3-phenyl-1H-indene-5-carboxylate (LXVIIIa)

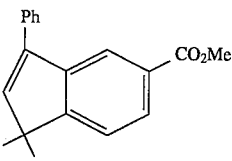

Methyl 1,1-dimethyl-3-(trifluoromethanesulfonyloxy)-1H-indene-5-carboxylate (580 mg, 1.86 mmol ), tris(dibenzylideneacetone)dipalladium (0) (Pd₂dba₃, 17 mg, 0.02 mmol), triphenylarsine (46 mg, 0.15 mmol), lithium chloride (240 mg, 5.59 mmol) and phenyltributyltin (680 mg, 1.86 mmol) in 5 mL of 2-methyl pyrrolidinone were stirred at 55° C. for 1.5 days. The mixture was diluted with water (30 mL), and extracted with ethyl ether (30 mL×3). The combined extracts were dried over magnesium sulfate and evaporated. The residue was purified by flash chromatography (EtOAc:hexane=1:20 to 1:5) to give 0.43 g (83% yield) of the title compound as a white solid; ¹H-NMR (CDCl₃) δ1.41 (s, 6H), 3.91 (s, 3H), 6.48 (s, 1H), 7.39–7.62 (m, 6H), 7.99 (d, J=6.8 Hz, 1H), 8.14 (s, 1H); MS m/e 279 (MH⁺).

Anal. calcd. for $C_{19}H_{18}O_2$. 0.25 $H_2O$: C, 80.68; H, 6.49. Found: C, 80.76; H, 6.41.

EXAMPLE 127

Methyl 4-[(1,1-Dimethyl-1,3-phenyl-1H-indene-5-carbonyl)amino]benzoate

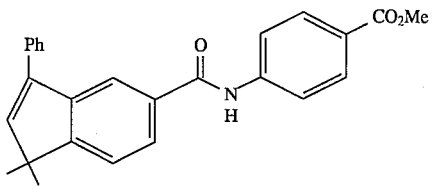

Methyl 1,1-dimethyl-3-phenyl-1H-indene-5-carboxylate (315 mg, 1.13 mmol) was stirred with 10N NaOH (1.1 mL, 11.0 mmol) in 5 mL of methanol and 10 mL of tetrahydrofuran at 60° C. for 1.5 hours. The solution was concentrated under reduced pressure and acidified with 1N HCl (15 mL), extracted with ethyl acetate (15 mL×3). The combined extracts were washed with water (10 mL), dried over magnesium sulfate, and evaporated. The residue was dried in vacuum and dissolved in 2.5 mL of methylene chloride. To the solution was added oxalyl chloride (348 mg, 2.74 mmol) and 2 drops of dimethylformamide at 0° C. The solution was stirred at 0° C. for 30 min and at room temperature for 30 min. The mixture was evaporated and dried in vacuum. The residue was stirred with methyl 4-aminobenzoate (181 mg, 1.32 mmol) in 2 mL of anhydrous pyridine for 18 hours. Excess pyridine was evaporated and the residue was diluted with 20 mL of 2N HCl, extracted with ethyl ether (30 mL×4). The combined extracts were washed with water (10 mL), dried over magnesium sulfate and evaporated. The residue was purified by flash chromatography (EtOAc:hexane=1:20 to 1:5) to give 372 mg (85% yield) of the title compound as a glassy mass; $^1$H-NMR (CDCl$_3$) δ1.43 (s, 6H), 3.91 (s, 3H), 6.52 (s, 1H), 7.40–7.50 (m, 4H), 7.59–7.61 (m, 2H), 7.72–7.75 (m, 3H), 7.96 (s, 1H), 8.00 (bs, 1H), 8.05 (d, J=8.7 Hz, 2H); MS m/e 398 (MH$^+$).

Anal. calcd. for C$_{26}$H$_{23}$NO$_3$.0.125 H$_2$O: C, 78.12; H, 5.93; N, 3.50. Found: C, 77.97; H, 5.50; N, 3.24

EXAMPLE 128

4-[(1,1-Dimethyl-3-phenyl-1H-indene-5-carbonyl)amino]benzoic acid

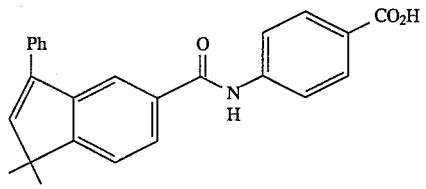

Methyl 4-[(1,1-dimethyl-3-phenyl-1H-indene-5-carbonyl)amino]benzoate (359 mg, 0.90 mmol) was stirred with 4.5 mL of 2N NaOH in 5 mL of methanol and 5 mL of tetrahydrofuran for 10 hours. The solution was acidified with 1N HCl and concentrated under reduced pressure. After addition of 15 mL of water, the mixture was extracted with ethyl acetate (15 mL×3). The combined extracts were washed with water (10 mL), dried over magnesium sulfate, and evaporated. The residue was triturated in etherhexane to give 326 mg (94% yield) of the title compound as solids; $^1$H-NMR (DMSO-d$_6$) δ1.39 (s, 6H), 6.68 (s, 1H), 7.39–7.53 (m, 3H), 7.64–7.68 (m, 3H), 7.85–7.97 (m, 6H), 10.54 (s, 1H), 12.75 (bs, 1H); MS m/e 384 (MH$^+$).

Anal. calcd. for C$_{25}$H$_{25}$NO$_3$.0.25 H$_2$O: C 77.39; H, 5.46; N, 3.61. Found: C, 77.26; H, 5.51; N, 3.52

EXAMPLE 129

1,1-Dimethyl-5-nitro-3-(trifluoromethanesulfonyloxy)-1H-indene

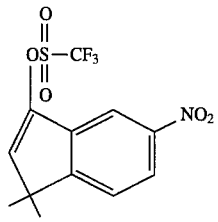

To a solution of 3,3-dimethyl-6-nitro-indan-1-one (LXIX) (1.00 g, 4.65 mmol) and 2,6-di-tert-butyl-4-methylpyridine (1.19 g, 5.80 mmol) in 10 mL of methylene chloride was added triflic acid anhydride (1.57 g, 5.58 mmol) at −78° C. After being stirred at room temperature for 16 hours, the mixture was diluted with 1N HCl (20 mL) and extracted with ethyl ether (30 mL×3). The combined extracts were washed with water (20 mL), dried over magnesium sulfate, and evaporated. The residue was purified by flash chromatography (EtOAc:hexane=1:20 to 1:10) to give 1.37 g (87% yield) of the title compound as an oil; $^1$H-NMR (CDCl$_3$) δ1.45 (s, 6H), 6.43 (s, 1H), 7.53 (d, J=8.3 Hz, 1H), 8.15 (d, J=2.0 Hz, 1H), 8.24 (dd, J= 2.0, 8.3 Hz, 1H); MS m/e 338 (MH$^+$).

Anal. calcd. for C$_{12}$H$_{10}$F$_3$NO$_5$S: C, 42.73; H, 2.99; N, 4.15. Found: C, 42.70; H, 2.80; 4.10.

EXAMPLE 130

1,1-Dimethyl-5-nitro-3-phenyl-1H-indene (LXXa)

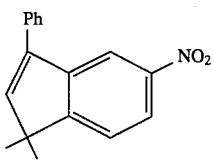

1,1-Dimethyl-5-nitro-3-(trifluoromethanesulfonyloxy)-1H-indene (1.32 g, 2.89 mmol), tris(dibenzylideneacetone)dipalladium (0) (21 mg, 0.02 mmol), triphenylarsine (70 mg, 0.23 mmol), lithium chloride (0.37 g, 8.67 mmol) and phenyltributyltin (1.06 g, 2.89 mmol) were stirred at 60° C. for 48 hours. The mixture was diluted with water (30 mL), extracted with ethyl ether (30 mL×3). The combined extracts were dried over magnesium sulfate and evaporated. The residue was purified by flash chromatography (EtOAc: hexane=1:25 to 1:5) to give a solid which recrystallized from hexane to give 575 mg (75% yield) of the title compound as light yellow crystals; $^1$H-NMR (CDCl$_3$) δ1.44 (s, 6H), 6.58 (s, 1H), 7.40–7.60 (m, 6H), 8.18 (d, J=2.0, 8.2 Hz, 1H), 8.32 (d, J=2.0 Hz, 1H); MS m/e 266 (MH$^+$).

Anal. calcd. for C$_{17}$H$_{15}$N O$_2$: C, 76.96; H, 5.70; N, 5.28. Found: C, 76.71; H, 5.69; N, 5.22.

EXAMPLE 131

5-Amino-1,1-dimethyl-3-phenyl-1H-indene (LXXIa)

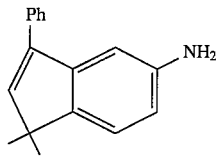

To a mixture of 1,1-dimethyl-5-nitro-3-phenyl-1H-indene (0.56 g, 2.11 mmol) in 5 mL of benzene was added 33% ferric chloride (1 mL) and 4 mL of water. The mixture was stirred at reflux and iron powder 1.00 g, 5.28 mmol) was added in four portions during 2 hours. The resulting mixture was stirred at reflux for additional 18 hours. The mixture was diluted with 20 mL of water and 20 mL of ethyl acetate, and filtered through a pad of celite. The filtrate was extracted with ethyl acetate (20 mL×3). The combined extracts were dried over magnesium sulfate to give 0.49 g (98% yield) of the crude title compound which was not further purified and used in the next reaction; $^1$H-NMR (CDCl$_3$) δ1.37 (s, 6H), 6.40 (s, 1H), 6.71 (dd, J=2.0, 7.9 Hz, 1H), 6.93 (d, J=2.0 Hz, 1H), 7.19 (d, J=7.9 Hz, 1H), 7.36–7.58 (m, 5H); MS m/e 236 (MH$^+$).

EXAMPLE 132

Methyl 4-(1,1-dimethyl-3-phenyl-1H-inden-5-yl)amino]carbonyl]benzoate

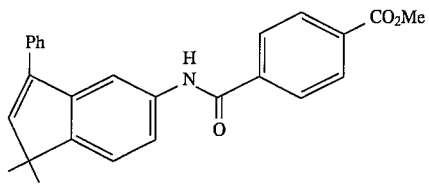

5-Amino-1,1-dimethyl-3-phenyl-1H-indene (0.49 g, 2.06 mmol) and terephthalic monomethyl ester chloride (0.49 g, 2.47 mmol) were stirred in 5 mL of pyridine for 18 hours. The solvent was evaporated and the residue was diluted with 1N HCl (20 ml), extracted with ethyl acetate (20 mL×3). The combined extracts were washed with saturated NaCl solution, dried over magnesium sulfate, and evaporated. The crude product was purified by flash chromatography (EtOAc:hexane=1:10 to 1:5) to give 772 mg (94% yield) of the title compound which crystallized from EtOAc-hexane to give 720 mg of crystals; $^1$H-NMR (CDCl$_3$) δ1.41 (s, 6H), 3.96 (s, 3H), 6.47 (s, 1H), 7.37–7.60 (m, 7 H), 7.68 (s, 1H), 7.84 (s, 1H), 7.94 (d, J=8.3 Hz, 2H), 8.16 (d, J=8.3 Hz, 2H); MS m/e 398 (MH$^+$).

Anal. calcd. for $C_{26}H_{23}NO_3$: C, 78.57; H, 5.83; N, 3.52. Found: C, 78.45; H, 5.76; N, 3.41.

EXAMPLE 133

4-[[(1,1-Dimethyl-3-phenyl-1H-inden-5-yl)amino]carbonyl]benzoic acid (I$^{31}$a)

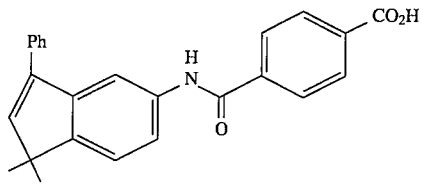

Methyl 4-[[(1,1-dimethyl-3-phenyl-1H-inden-5-yl)amino]carbonyl]benzoate (325 mg, 0.82 mmol), 4.1 mL of 2N NaOH in 10 mL of tetrahydrofuran and 10 mL of methanol were stirred for 2 hours. The mixture was concentrated and acidified with 1N HCl (20 mL), extracted with ethyl acetate (35 mL×2). The combined extracts were washed with water (10 mL), dried over magnesium sulfate, and evaporated. The residue was triturated in ether-hexane to give 246 mg (78% yield) of the title compound as white solids; NMR (DMSO-d$_6$) δ1.35 (s, 6H), 6.58 (s, 1H), 7.38–7.70 (m, 7H), 7.73 (d, J=7.9 Hz, 1H), 7.90 (s, 1H), 8.04 (s, 4H), 10.38 (bs, 1H), 13.25 (bs, 1H); MS m/e 384 (MH$^+$).

Anal. calcd. for $C_{25}H_{21}NO_3$. 0.25 H$_2$O: C, 77.40; H, 5.59; N, 3.61. Found: C, 77.24; H, 5.33; N, 3.41.

EXAMPLE 134

Methyl 4-(1,1-dimethyl-3-oxo-indan-5-yloxymethyl-)benzoate (LXXIIa)

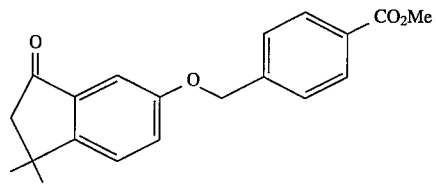

6-Hydroxy-3,3-dimethyl-indan-1-one (0.72 g, 4.37 mmol) in 5 mL of dimethylformamide was added sodium hydride (0.16 g, 6.55 mmol) at 0° C. After stirring for 30 min, methyl 4-bromomethylbenzoate (1.00 g, 4.37 mmol) was added. The resulting mixture was stirred at 0° C. for 1 hour and at room temperature for 2 hours. The mixture was cooled to 0° C. and acidified with 1N HCl. The solvent was evaporated and the residue was acidified with 20 mL of 1N HCl and extracted with ethyl ether (30 mL×3). The combined extracts were dried over magnesium sulfate and evaporated. The residue was purified by flash chromatography (EtOAc: hexane=1:20 to 1:4) to give 0.68 g (48% yield) of the title compounds as a solid; $^1$H-NMR (CDCl$_3$) δ1.41 (s, 6H), 2.61 (s, 2H), 3.93 (s, 1H), 5.15 (s, 2H), 7.18 (d, J=2.5 Hz, 1H), 7.30 (d, J=2.5, 8.4 Hz, 1H), 7.42 (d, J=8.4 Hz, 1H), 7.51 (d, J=8.3 Hz, 2H), 8.07 (d, J=8.3 Hz, 2H); MS m/e 325 (MH$^+$).

Anal. calcd. for $C_{20}H_{20}O_4$: C, 74.06; H, 6.21. Found: C, 73.99; H, 6.24.

EXAMPLE 135

Methyl 4-[1,1-dimethyl-3-(trifluoromethanesulfonyloxy)-1H-indene-5-yloxymethyl]benzoate

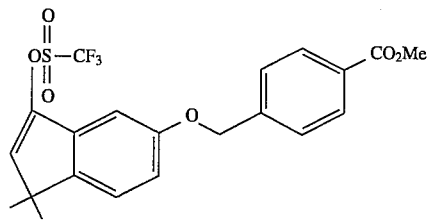

To a solution of methyl 4-(1,1-dimethyl-3-oxo-indan-5-yloxymethyl)benzoate (675 mg, 2.08 mmol) and 2,6-di-tert-butyl-4-methylpyridine (534 mg, 2.60 mmol) in 5 mL of methylene chloride was added triflic acid anhydride (705 mg, 2.50 mmol) at −78° C. After being stirred at room temperature for 16 hours, the mixture was diluted with 1N HCl (20 mL), extracted with ethyl ether (20 mL×3). The combined extracts were dried over magnesium sulfate and evaporated. The residue was purified by flash chromatography (EtOAc:hexane=1:20 to 1:10) to give 849 mg (95% yield) of the title compound as a solid; $^1$H-NMR (CDCl$_3$) δ1.37 (s, 6H), 3.93 (s, 1H), 5.15 (s, 2H), 6.24 (s, 1H), 6.90–6.94 (m, 2H), 7.25 (d over CHCl$_3$, J=8.8 Hz, 1H), 7.53 (d, J=8.7 Hz, 2H), 8.08 (d, J=8.7 Hz, 2H); MS m/e 457 (MH$^+$).

Anal. calcd. for C$_{21}$H$_{19}$F$_3$O$_6$S: C, 55.26; H, 4.20. Found: C, 55.39; H, 4.08.

EXAMPLE 136

Methyl 4-(1,1-dimethyl-3-phenyl-1H-inden-5-yloxymethyl)benzoate

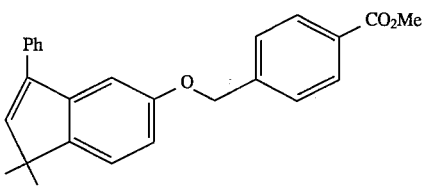

Methyl 4-[1,1-dimethyl-3-(trifluoromethanesulfonyloxy)-1H-indene-5-yloxymethyl]benzoate (838 mg, 1.84 mmol), tris(dibenzylideneacetone)dipalladium (0) (17 mg, 0.02 mmol), triphenylarsine (64 mg, 0.20 mmol), lithium chloride (234 mg, 5.51 mmol) and phenyltributyltin (676 mg, 1.84 mmol) were stirred at 60° C. for 18 hours. The mixture was diluted with water (30 mL), extracted with ethyl ether (30 mL×3). The combined extracts were dried over magnesium sulfate and evaporated. The residue was purified by flash chromatography (EtOAc:hexane=1:25 to 1:10) to give a product which recrystallized from EtOAc-hexane (1:20 to 1:10) to give 454 mg (64% yield) of the title compound as crystals; $^1$H-NMR (CDCl$_3$) δ1.38 (s, 6H), 3.93 (s, 1H), 5.13 (s, 2H), 6.44 (s, 1H), 6.86 (dd, J=2.2, 8.1 Hz, 1H), 7.11 (d, J=2.2 Hz, 1H), 7.27–7.55 (m, 8 H), 8.06 (d, J=8.1 Hz, 2H); MS m/e 385 (MH$^+$).

Anal. calcd. for C$_{26}$H$_{24}$O$_3$ 0.125 H$_2$O: C, 80.75; H, 6.32. Found: C, 80.7 6; H, 6.19.

EXAMPLE 137

4-[1,1-Dimethyl-3-phenyl-1H-inden-5-yloxymethyl)benzoic acid (I$^{32}$a)

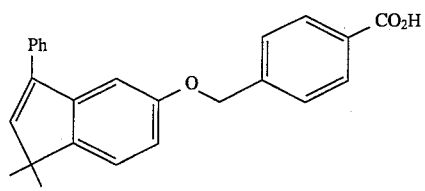

Methyl 4-(1,1-dimethyl-3-phenyl-1H-inden-5-yloxymethyl)benzoate (300 mg, 0.78 mmol) and 3.9 mL of 2N NaOH in 5 mL of tetrahydrofuran and 5 mL of methanol were stirred at room temperature for 16 hours. The mixture was concentrated and acidified with 1N HCl (10 mL), extracted with ethyl acetate (20 mL×3). The combined extracts were washed with water (10 mL), dried over magnesium sulfate, and evaporated. The residue was crystallized from ether-hexane to give 247 mg (85% yield) of the title compound as white crystals; $^1$H-NMR (DMSO-d$_6$) δ1.31 (s, 6H), 5.20 (s, 2H), 6.57 (s, 1H), 6.89 (dd, J=1.1, 8.2 Hz, 1H), 7.02 (d, J=1.1 Hz, 1H), 7.36–7.57 (m, 8H), 7.95 (d, J=8.3 Hz, 2H), 12.94 (bs, 1H) ; MS m/e 371 (MH$^+$).

Anal. calcd. for C$_{25}$H$_{22}$O$_3$ 0.25 H$_2$O: C, 80.08; H, 6.05. Found: C, 80.17; H, 5.86.

EXAMPLE 138

6-Bromo-3,3-dimethyl-indan-1-one (LXXIV)

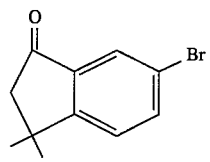

To aluminum chloride (4.16 g, 31.2 mmol) in a flask was added 3,3-dimethyl-1-indan-1-one (2.00 g, 12.5 mmol) at 90°–100° C. After stirring for 15 min, bromine (2.39 g, 15.0 mmol) was slowly added. The mixture was stirred at 100° C. for 1 hour and then quenched with ice-water (200 g), extracted with ethyl acetate (40 mL×3). The combined extracts were dried over magnesium sulfate and evaporated. The residue was purified by flash chromatography (EtOAc:hexane=1:20 to 1:15) to give a crude product which recrystallized from MeOH-EtOAc to give 1.23 g (41% yield) of the title compound as colorless crystals; $^1$H-NMR (CDCl$_3$) δ1.42 (s, 6H), 2.61 (s, 2H), 7.39 (d, J=8.2 Hz, 1H), 7.72 (dd, J=2.0, 8.2 Hz, 1H), 7.82 (d, J=2.0 Hz, 1H); MS m/e 239 (MH$^+$).

Anal. calcd. for C$_{11}$H$_{11}$BrO$_3$: C, 55.26; H, 4.64. Found: C, 55.19; H, 4.61.

EXAMPLE 139

Methyl 4-[2-(1,1-dimethyl-3-oxo-indan-5-yl)vinyl]benzoate (LXXVa)

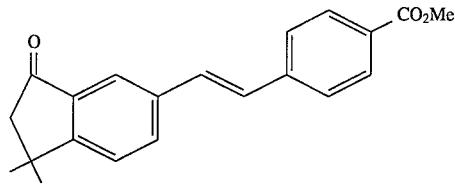

6-Bromo-3,3-dimethyl-indan-1-one (1.20 g, 5.02 mmol), methyl 4-vinylbenzoate (1.63 g, 10.0 mmol), palladium acetate (56 mg, 0.25 mmol), tetrabutylammonium chloride hydrate (1.53 g, 5.52 mmol), and sodium bicarbonate (1.05 g, 12.6 mmol) were stirred in 10 mL of anhydrous N,N-dimethylformamide at 80°–100° C. for 8 hours. The mixture was diluted with water (100 mL), extracted with methylene chloride (50 mL×3). The combined extracts were dried over magnesium sulfate and evaporated. The residue was purified by flash chromatography ($CH_2Cl_2$:hexane=1:1 to 1:0, then $CH_2Cl_2$:EtOAc=10:1) to give 1.12 g (70% yield) of the title compound as a yellow solid; $^1$H-NMR ($CDCl_3$) δ1.45 (s, 6H), 2.64 (s, 2H), 5.30 (s, 3H), 7.18 (d, J=16.5 Hz, 1H), 7.26 (d, J=16.5 Hz, 1H), 7.52 (d, J=8.1 Hz, 1H), 7.58 (d, J=8.5 Hz, 2H), 7.78 (d, J=1.7, 8.1 Hz, 1H), 7.86 (d, J=1.7 Hz, 1H), 8.05 (d, J=8.5 Hz, 2H); MS m/e 321 (MH$^+$).

Anal. calcd. for $C_{21}H_{20}O_3$: C, 78.18; H, 6.32. Found: C, 78.22; H, 6.26.

EXAMPLE 140

Methyl [2-[1,1-dimethyl-3-(trifluoromethanesulfonyloxy)-1H-indene-5-yl]vinyl]benzoate

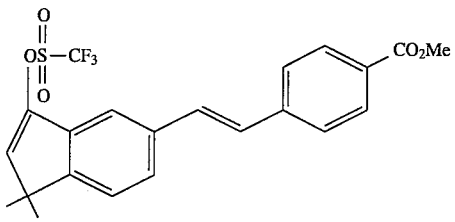

To a solution of methyl 4-[2-(1,1-dimethyl-3-oxo-indan-5-yl)vinyl]benzoate (450 mg, 1.40 mmol) and 2,6-di-tert-butyl-4-methylpyridine (345 mg, 1.68 mmol) in 5 mL of methylene chloride was added triflic acid anhydride (434 mg, 1.54 mmol) at −78° C. After stirring at room temperature for 16 hours, the mixture was diluted with 1N HCl (20 mL), extracted with ethyl ether (20 mL×3). The combined extracts were dried over magnesium sulfate and evaporated. The residue was purified by flash chromatography ($CH_2Cl_2$; hexane=1:2 to 1:1) to give 606 mg (95% yield) of the title compound as a solid; $^1$H-NMR ($CDCl_3$) δ1.41 (s, 6H), 3.94 (s, 3H), 6.27 (s, 1H), 7.15 (d, J=16.3 Hz, 1H), 7.27 (d, J=16.3 Hz, 1H), 7.37 (d, J=8.2 Hz, 1H), 7.49 and 7.50 (d over s, J=8.2 Hz, 2H), 7.59 (d, J=8.4 Hz, 2H), 8.05 (d, J=8.4 Hz, 2H); (MS m/e 453 (MH$^+$).

Anal. calcd. for $C_{22}H_{19}F_3O_5S$: C, 58.40; H, 4.23. Found: C, 58.38; H, 4.00.

EXAMPLE 141

Methyl 4-[2-(1,1-dimethyl-3-phenyl-1H-inden-5-yl)vinyl]benzoate

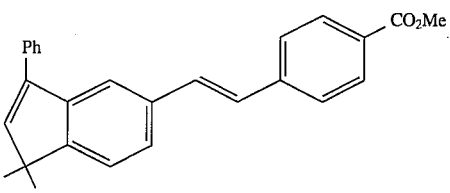

Methyl [2-[1,1-dimethyl-3-(trifluoromethanesulfonyloxy)-1H-indene-5-yl]vinyl]benzoate (590 mg, 1.30 mmol), tris(dibenzylideneacetone)dipalladium (0) (48 mg, 0.05 mmol), triphenylarsine (64 mg, 0.20 mmol), lithium chloride (166 mg, 3.91 mmol) and phenyltributyltin (525 mg, 1.43 mmol) were stirred at 95° C. for 16 hours. The mixture was diluted with water (75 mL), extracted with ethyl acetate (20 mL×2) and ethyl ether (20 mL×2). The combined extracts were dried over magnesium sulfate and evaporated. The residue was purified by flash chromatography (EtOAc:hexane=1:25 to 1:10) to give a product which recrystallized from EtOAc-hexane to give 311 mg (63% yield) of the title compound as yellow solids; $^1$H NMR ($CDCl_3$) δ1.42 (s, 6H), 3.93 (s, 3H), 6.45 (s, 1H), 7.11 (d, J=16.3 Hz, 1H), 7.29 (d, J=16.3 Hz, 1H), 7.41–7.65 (m, 10H), 8.02 (d, J=8.4 Hz, 2H).

EXAMPLE 142

4-[2-(1,1-dimethyl-3-phenyl-1H-inden-5-yl)vinyl]benzoic acid (I$^{33}$a)

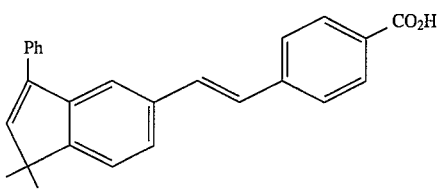

Methyl 4-[2-(1,1-dimethyl-3-phenyl-1H-inden-5-yl)-vinyl]benzoate (294 mg, 0.77 mmol) and 0.77 mL of 10N NaOH in 7 mL of tetrahydrofuran and 5 mL of methanol were stirred at reflux for 1 hour. The mixture was concentrated and acidified with 1N HCl (10 mL), extracted with ethyl acetate (30 mL×2). The combined extracts were washed with water (10 mL), dried over magnesium sulfate, and evaporated. The residue was triturated in hot methanol to give 276 mg (90% yield) of the title compound which contained a molecule of methanol; $^1$H-NMR (DMSO-$d_6$) δ1.34 (s, 6H), 3.14 (s, 3H), 6.58 (s, 1H), 7.25 (d, J=16.4 Hz, 1H), 7.37–7.71 (m, 11H), 7.90 (d, J=8.3 Hz, 2H); MS m/e 367 (MH$^+$).

Anal. calcd. for $C_{26}H_{26}O_3 \cdot CH_3OH$: C, 81.38; H, 6.58. Found: C, 81.18; H, 6.78.

EXAMPLE 143

N-(2-pyridyl)triflimide

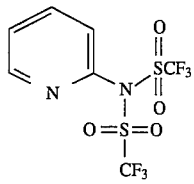

The title compound was prepared by procedure of Comins & Dehghani, *Tetrahedron Lett.*, Vol. 33, No. 42, 1992, p. 6299. $^1$H NMR (CDCl$_3$): δ8.66 (m, 1H), 7.95 (m, 1H), 7.56 (m, 1H), 7.48 (d, 1H). MS (DCI) m/e: 359 (MH$^+$).

EXAMPLE 144

4-[[[(5,6-Dihydro-5,5-dimethyl-8-phenyl)-2-naphthalenyl]carbonyl]amino]-2-hydroxybenzoic acid, phenyl ester (I$^3$j)

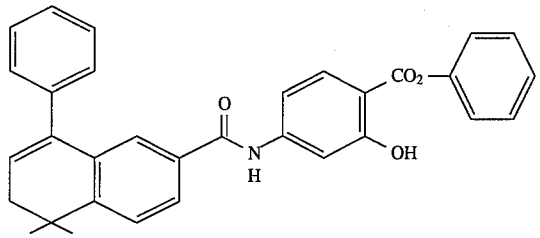

Using the method given for the preparation of the 8-(2-fluorophenyl) derivative I$^3$g, 230 mg (0.83 mmol) of compound XVIIIa and phenyl 4-aminosalicylate (Aldrich; 190 mg, 0.83 mmol) gave 193 mg (Y: 48%) of the title product; $^1$H-NMR (CDCl$_3$): δ8.03 (d, J=9.3 Hz, 1H), 7.75–7.71 (m, 2H), 7.51–7.19 (m, 13H), 6.09 (t, J=4.5 Hz, 1H), 2.40 (d, J=4.5 Hz, 2H), 1.38 (s, 6H); MS (DCI) m/e: 490 (MH$^+$).

EXAMPLE 145

4-[[[(5,6-Dihydro-5,5-dimethyl-8-phenyl)-2-naphthalenyl]carbonyl]amino]-2-hydroxybenzoic acid (I$^4$j)

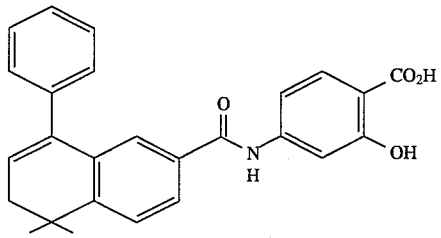

Using the method for the preparation of the 8-phenyl derivative I$^4$a, 193 mg (0.39 mmol) of compound I$^3$j gave 135 mg (Y: 83%) of the title compound; $^1$H-NMR (DMSO-d$_6$): δ11.33 (bs, 1H), 10.38 (s, 1H), 7.83 (dd, J=8.0, 1.7 Hz, 1H), 7.71 (d, J=8.7 Hz, 1H), 7.54 (d, J=8.0 Hz, 1H), 7.45–7.29 (m, 7H), 7.24 (dd, J=8.7, 1.8 Hz, 1H), 6.06 (t, J=4.5 Hz, 1H), 2.35 (d, J=4.5 Hz, 2H), 1.32 (s, 6H); MS (DCI) m/e: 400 (MH$^+$); IR (KBr): 2960, 1668, 1600, 1508.

Anal. calcd. for C$_{26}$H$_{23}$N$_1$O$_4$•0.5 H$_2$O: C, 73.92, H, 5.73; N, 3.32. Found: C, 73.91; H, 5.73; N, 2.99.

EXAMPLE 146

2-Fluoro-4-nitrobenzoic acid

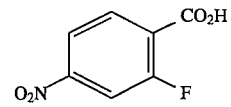

A solution of 2-fluoro-4-nitrotoluene (3.95 g, 25.5 mmol, Janssen) in water (200 mL) was treated portionwise with potassium permanganate (24.6 g, 0.15 mmol) at 80° C. After 2h the reaction mixture was filtered hot, acidified with 5N hydrochloric acid and extracted with ethyl acetate (2×100 mL). The extract was dried over anhydrous sodium sulfate and concentrated in vacuo to give 1.15 g (Y: 24%) of the title compound; $^1$H-NMR (DMSO-d$_6$): δ8.21 (d, J=10.5 Hz, 1H), 8.16–8.08 (m, 2H); MS (DCI) m/e: 186 (MH$^+$).

EXAMPLE 147

2-Fluoro-4-nitrobenzoic acid ethyl ester

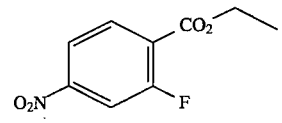

To a solution of 2-fluoro-4-nitrobenzoic acid (1.15 g, 6.22 mmol) in absolute ethyl alcohol (20 mL) was added p-toluenesulfonic acid monohydrate (100 mg). After 16 h at reflux, the reaction mixture was concentrated in vacuo and the residue chromatographed on silica gel (eluted with 5% ethyl acetate in hexane) to give 770 mg (Y: 58%) of the title product; $^1$H-NMR (CDCl$_3$): δ8.16–8.00 (m, 3H), 4.45 (q, J=7.1 Hz, 2H), 1.43 (t, J=7.1 Hz, 3H). MS (DCI) m/e: 214 (MH$^+$).

EXAMPLE 148

2-Fluoro-4-aminobenzoic acid ethyl ester

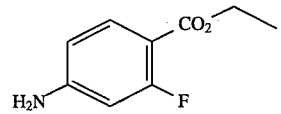

A solution of 2-fluoro-4-nitrobenzoic acid ethyl ester (770 mg, 3.62 mmol) in methyl alcohol (15 mL) was treated with platinum (IV) oxide (75 mg) at 40 psi of H$_2$. After 0.5 h the reaction mixture was filtered through celite and concentrated in vacuo to give 700 mg (Y: 99%) of the title product; $^1$H-NMR (CDCl$_3$): δ7.76 (t, J=8.3 Hz, 1H), 6.42 (d, J=8.5 Hz, 1H), 6.35 (d, J=12.9 Hz, 1H), 4.33 (q, J=7.1 Hz, 2H), 4.20 (bs, 2H), 1.36 (t, J=7.1 Hz, 3H); MS (DCI) m/e: 184 (MH$^+$).

EXAMPLE 149

4-[[[(5,6-Dihydro-5,5-dimethyl-8-phenyl)-2-naphthalenyl]carbonyl]amino]-2-fluorobenzoic acid, ethyl ester (I³k)

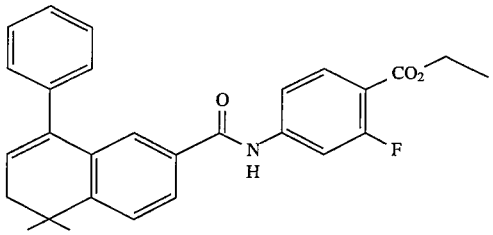

Using the method given for the preparation of the 8-(2-fluorophenyl) derivative I³g, 250 mg (0.90 mmol) of compound XVIIIa and 2-fluoro-4-aminobenzoic acid ethyl ester (181 mg, 0.99 mmol) gave 240 mg (Y: 60%) of the title product; $^1$H-NMR (CDCl$_3$): δ7.91 (t, J=8.5 Hz, 1H), 7.72 (d, J=10.1 Hz, 1H), 7.66 (d, J=1.8 Hz, 1H), 7.51–7.48 (m, 1H), 7.44–7.35 (m, 6H), 7.20 (d, J=8.6 Hz, 1H), 6.08 (t, J=4.5 Hz, 1H), 4.37 (q, J=7.1 Hz, 2H), 2.40 (d, J=4.5 Hz, 2H), 1.38 (t, J=7.1 Hz, 1.37 (s, 6H); MS (DCI) m/e: 444 (MH$^+$).

EXAMPLE 150

4-[[[(5,6-Dihydro-5,5-dimethyl-8-phenyl)-2-naphthalenyl]carbonyl]amino]-2-fluorobenzoic acid (I⁴k)

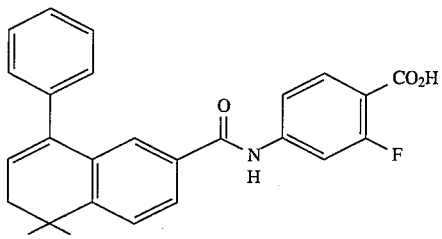

Using the method given for the preparation of the 8-phenyl derivative I⁴a, 240 mg (0.54 mmol) of compound I³k gave 175 mg (Y: 78%) of the title compound; $^1$H-NMR (DMSO-d$_6$): δ12.98 (bs, 1H), 10.58 (s, 1H), 7.89–7.77 (m, 2H), 7.73 (d, J=1.5 Hz, 1H), 7.54 (d, J=8.1 Hz, 1H), 7.44–7.30 (m, 7H), 6.06 (t, J=4.5 Hz, 1H), 2.34 (d, J=4.5 Hz, 2H), 1.31 (s, 6H). MS (DCI) m/e: 416 (MH$^+$); IR (KBr): 2960, 1692, 1596, 1526.

Anal. calcd for C$_{26}$H$_{22}$N$_1$O$_3$F$_1$•0.25 H$_2$O: C, 74.36; H, 5.40; N, 3.34. Found: C, 74.16; H, 5.74; N, 3.13.

EXAMPLE 151

N-(4-Methyl-3-nitro-phenyl)acetamide

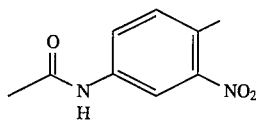

A solution of 4-methyl-3-nitroaniline (3.60 g, 23.7 mmol) in acetic anhydride (28 mL) was allowed to stir at room temperature. After 16 h, the reaction mixture was concentrated in vacuo, diluted with ethyl acetate (25 mL), washed with saturated sodium bicarbonate (2×50 mL), dried over anhydrous sodium sulfate and concentrated in vacuo to give 4.20 g (Y: 99%) of the title compound; $^1$H-NMR (CDCl$_3$): δ8.10 (d, J=1.7 Hz, 1H), 7.75 (dd, J=8.5, 1.7 Hz, 1H), 7.38 (bs, 1H), 7.29 (d, J=8.5 Hz, 1H), 2.56 (s, 3H), 2.21 (s, 3H); MS (DCI) m/e: 195 (MH$^+$).

EXAMPLE 152

4-Acetylamino-2-nitrobenzoic acid

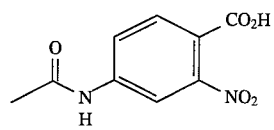

A solution of N-(4-methyl-3-nitro-phenyl)acetamide (4.20 g, 23.6 mmol) in water (200 mL) was treated portionwise with potassium permanganate (22.77 g, 0.144 mmol) at 80° C. After 2 h the reaction mixture was filtered hot, acidified with 5N hydrochloric acid and extracted with ethyl acetate (2×100 mL). The extract was dried over anhydrous sodium sulfate and concentrated in vacuo to give 1.80 g (Y: 34%) of the title compound; $^1$H-NMR (CDCl$_3$): δ10.63 (s, 1H), 8.19 (d, J=1.7 Hz, 1H), 7.85 (d, J=8.5 Hz, 1H), 7.78 (dd, J=8.5, 1.7 Hz, 1H), 2.10 (s, 3H); MS (DCI) m/e: 225 (MH$^+$).

EXAMPLE 153

4-Amino-2-nitrobenzoic acid ethyl ester

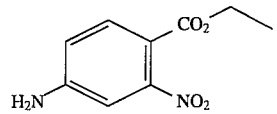

A solution of 4-acetylamino-2-nitrobenzoic acid (1.80 g, 8.0 mmol) in 12 N hydrochloric acid (14 mL) and absolute ethyl alcohol (10 mL) was heated to 90°–100° C. for 5 h. Concentrated down in vacuo to remove ethyl alcohol only, adjusted pH to 4 with 1N sodium hydroxide and filtered off precipitate to give 140 mg (Y: 8%) of the title compound; $^1$H-NMR (CDCl$_3$): δ7.61 (d, J=8.5 Hz, 1H), 6.82 (d, J=2.1 Hz, 1H), 6.74 (dd, J=8.5, 2.1 Hz, 1H), 6.52 (bs, 2H), 4.17 (q, J=7.1 Hz, 2H), 1.21 (t, J=7.1 Hz, 3H); MS (DCI) m/e: 211 (MH$^+$).

EXAMPLE 154

4-[[[(5,6-Dihydro-5,5-dimethyl-8-phenyl)-2-naphthalenyl]carbonyl]amino]-2-nitrobenzoic acid, ethyl ester (I³l)

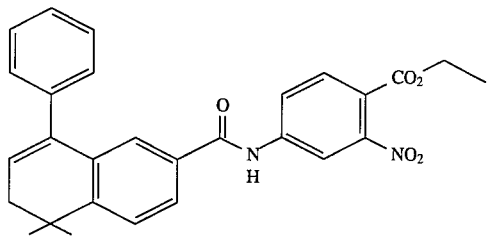

Using the method given for the preparation of the 8-(2-fluorophenyl) derivative I³g, 199 mg (0.71 mmol) of compound XVIIIa and 140 mg (0.78 mmol ) of 4-amino-2-nitrobenzoic acid ethyl ester gave 155 mg (Y: 46%) of the title product; ¹H-NMR (CDCl₃): δ8.15 (s, 1H), 7.84 (s, 1H), 7.79 (s, 1H), 7.73 (dd, J=8.1, 1.9 Hz, 1H), 7.52–7.49 (m, 2H), 7.41–7.26 (m, 5H), 6.09 (t, J=4.5 Hz, 1H), 4.36 (q, J=7.2 Hz, 2H), 2.40 (d, J=4.5 Hz, 2H), 1.37 (s, 6H), 1.34 (t, J=7.2 Hz, 3H); MS (DCI) m/e: 471 (MH⁺).

EXAMPLE 155

4-[[[(5,6-Dihydro-5,5-dimethyl-8-phenyl)-2-naphthalenyl]carbonyl]amino]-2-nitrobenzoic acid (I⁴l)

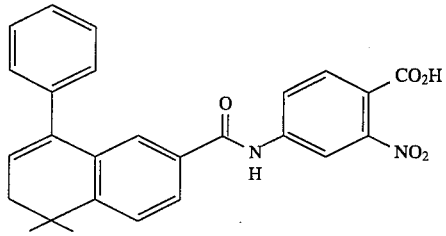

Using the method given for the preparation of the 8-phenyl derivative I⁴a, 155 mg (0.33 mmol) of compound I³l gave 105 mg (Y: 72%) of the title compound; ¹H-NMR (DMSO-d₆): δ13.65 (bs, 1H), 10.76 (s, 1H), 8.31 (d, J=1.7 Hz, 1H), 7.99 (dd, J=8.3, 1.7 Hz, 1H), 7.90–7.84 (m, 2H), 7.55 (d, J=8.3 Hz, 1H), 7.47 (d, J=1.7 Hz, 1H), 7.44–7.30 (m, 5H), 6.07 (t, J=4.5 Hz, 1H), 2.33 (d, J=4.5 Hz, 2H), 1.31 (s, 6H); MS (DCI) m/e: 443 (MH⁺); IR (KBr): 2960, 1702, 1542, 1518.

Anal. calcd. for C₂₆H₂₂N₂O₅•0.5 H₂O: C, 69.17, H, 5.14, N, 6.20. Found: C, 69.55, H, 4.93, N, 5.94.

EXAMPLE 156

4-[[[(5,6-Dihydro-5,5-dimethyl-8-phenyl)-2-naphthalenyl]carbonyl]amino-2-mehoxybenoic acid, methyl ester (I³m)

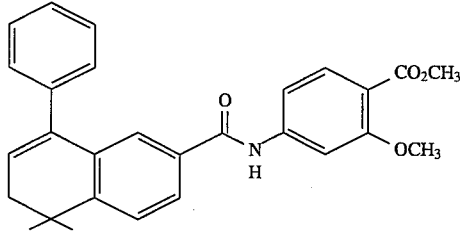

Using the method for the preparation of the 8-(2fluorophenyl) derivative I³g, 415 mg (1.49 mmol) compound XVIIIa and 297 mg (1.64 mmol) of methyl 4-amino-2-methoxybenzoate (Apin) gave 570 mg (Y: 90%) of the title product; ¹H-NMR (CDCl₃): δ7.82 (d, J=8.5 Hz, 1H), 7.77 (d, J=1.7 Hz, 1H), 7.73 (s, 1H), 7.70 (d, J=1.9 Hz, 1H), 7.51 (m, 1H), 7.48 (s, 1H), 7.41–7.33 (m, 4H), 6.80 (dd, J=8.5, 1.9 Hz, 1H), 6.08 (t, J=4.5 Hz, 1H), 3.92 (s, 3H), 3.87 (s, 3H), 2.39 (d, J=4.5 Hz, 2H), 1.38 (s, 6H); MS (DCI) m/e: 442 (MH⁺).

EXAMPLE 157

4-[[[(5,6-Dihydro-5,5-dimethyl-8-phenyl)-2-naphthalenyl]carbonyl]amino]-2-methoxybenzoic acid (I⁴m)

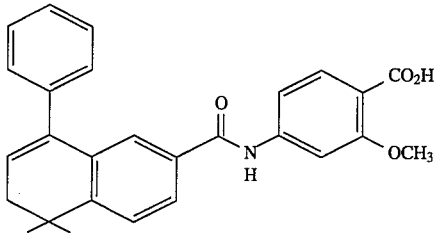

Using the method given for the preparation of the 8-phenyl derivative I⁴a, 135mg (0.31 mmol) of compound I³m gave 100 mg (Y: 77%) of the title compound; 1H-NMR (DMSO-d₆): δ12.32 (bs, 1H), 10.36 (s, 1H), 7.85 (dd, J=8.1, 1.7 Hz, 1H), 7.79 (s, 1H), 7.64 (d, J=1.7 Hz, 1H), 7.53 (d, J=8.1 Hz, 1H), 7.44–7.30 (m, 7H), 6.06 (t, J=4.5 Hz, 1H), 3.76 (s, 3H), 2.34 (d, J=4.5 Hz, 2H), 1.31 (s, 6H); MS (DCI) m/e: 428 (MH⁺); IR (KBr): 2960, 1718, 1592, 1524.

Anal. calcd. for C₂₇H₂₅N₁O₄•0.25 H₂O: C, 75.07; H, 5.95; N, 3.24. Found: C, 75.04; H, 5.86; N, 3.04.

EXAMPLE 158

4-[[[(5,6-Dihydro-5,5-dimethyl-8-(2-naphthalene)]-2-naphthaleny]carbonyl]amino]benzoic acid (I⁴n)

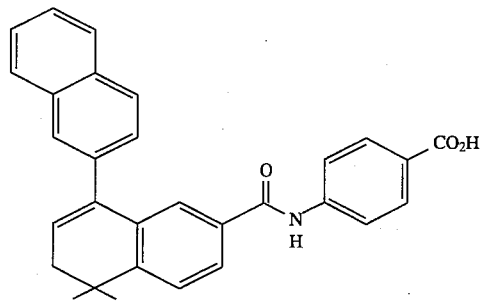

Starting from compound XVIa the title compound was made from a method analogous to the preparation of the 8-(2-fluorophenyl) derivative I⁴g; ¹H-NMR (DMSO-d₆): δ12.69 (s, 1H), 10.41 (s, 1H), 7.95–7.88 (m, 5H), 7.85 (d, J=8.7 Hz, 2H), 7.77 (d, J=8.7 Hz, 2H), 7.57–7.40 (m, 5H), 6.20 (t, J=4.5 Hz, 1H), 2.40 (d, J=4.5 Hz, 2H), 1.35 (s, 6H); MS (DCI) m/e: 448 (MH⁺); IR (KBr): 2960, 1686, 1596, 1518.

Anal. calcd. for C₃₀H₂₅O₃N₁•0.90 H₂O: C, 77.70; H, 5.83; N, 3.02. Found: C, 78.10; H, 5.55; N, 3.13.

EXAMPLE 159

4-[[(5,6-Dihydro-8-phenyl-2-naphthalenyl)carbonyl]amino]benzoic acid (I⁴o)

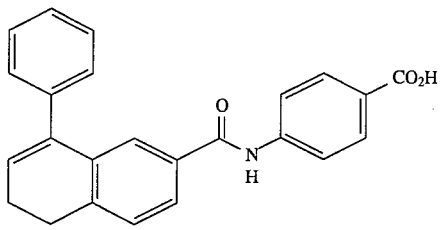

Starting from 6-methoxy tetralone the title compound was made from a method analogous to the preparation of the 8-(2-fluorophenyl) derivative I⁴g; ¹H-NMR (DMSO-$d_6$): δ12.73 (s, 1H), 10.42 (s, 1H), 7.91–7.81 (m, 5H), 7.55–7.25 (m, 7H), 6.18 (t, J=4.5 Hz, 1H), 2.86 (t, J=7.6 Hz, 2H), 2.41–2.34 (m, 2H); MS (DCI) m/e: 370 (MH⁺); IR (KBr): 2950, 1680, 1648, 1518.

Anal. calcd. for $C_{24}H_{19}N_1O_3$: C, 78.03; H, 5.18; N, 3.79. Found: C, 77.61; H, 5.14; N, 3.81.

EXAMPLE 160

Methyl 4-[[(5,6-dihydro-5,5-dimethyl-8-phenyl-2-naphthalenyl)carbonyl]amino]-3-fluorobenzoate (I³p)

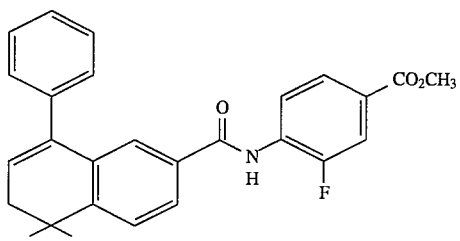

Using the method given for the preparation of the 8-(2-fluorophenyl) derivative I³g, compound XVIIIa (300 mg) and methyl 3-fluoro-4-aminobenate (245 mg) gave 320 mg (69% yield) of the title compound as a glassy mass; ¹H-NMR (CDCl₃) δ1.38 (s, 6H), 2.40 (d, J=4.7 Hz, 2H), 3.90 (s, 3H), 6.08 (t, J=4.7 Hz, 1H), 7.32–7.42 (m, 5H), 7.49 (d, J=8.0 Hz, 1H), 7.56 (d, J=1.9 Hz, 1H), 7.73 (d, J=1.9, 8.0 Hz, 1H), 7.74 (d, J=1.8, 11.5 Hz, 1H), 7.84 (dd, J=1.8 8.5 Hz, 1H), 8.11 (bd, J=3.8 Hz, 1H), 8.55 (t, J=8.5 Hz, 1H).

EXAMPLE 161

4-[[(5,6-Dihydro-5,5-dimethyl-8-phenyl-2-naphthalenyl)carbonyl]amino]-3-fluorobenzoic acid (I⁴p)

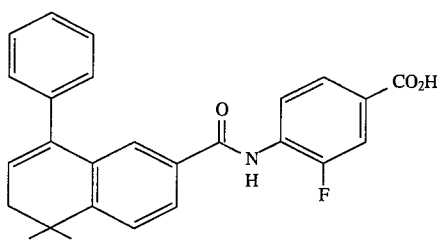

Using the same method given for the preparation of the 8-phenyl derivative I⁴a, 310 mg of compound I³p gave 170 mg (54% yield) of the title compound; ¹H-NMR (CDCl₃) δ1.23 (s, 6H), 2.39 (d, J=4.7 Hz, 2H), 6.07 (t, J=4.7 Hz, 1H), 7.30–7.42 (m, 5H), 7.49 (d, J=8.1 Hz, 1H), 7.52 (d, J=2.0 Hz, 1H), 7.72 (d, J=2.0, 8.1 Hz, 1H), 7.79 (d, J=1.8, 11.4 Hz, 1H), 7.90 (d, J=8.5 Hz, 1H), 8.06 (bd, J=4.2 Hz, 1H), 8.59 (t, J=8.6 Hz, 1H); MS m/e 416 (MH⁺).

Anal Calcd. for $C_{26}H_{22}FNO_3$: C, 75.17; H, 5.34; N, 3.37. Found: C, 74.96; H, 5.53; N, 3.33.

EXAMPLE 162

Methyl 4-[[(5,6-dihydro-5,5-dimethyl-8-phenyl-2-naphthalenyl)carbonyl]amino]-3-methylbenzoate (I³g)

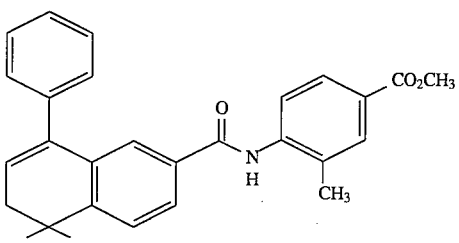

Using the method given for the preparation of the 8-(2-fluorophenyl) derivative I³g, compound XVIIIa (300 mg) and methyl 3-methyl-4-aminobenate (319 mg) gave 305 mg (66% yield) of the title compound as a glassy mass; ¹H-NMR (CDCl₃) δ1.39 (s, 6H), 2.20 (s, 3H), 2.41 (d, J=4.7 Hz, 2H), 3.89 (s, 3H), 6.09 (t, J=4.7 Hz, 1H), 7.30–7.45 (m, 5H), 7.48 (d, J=2.0 Hz, 1H), 7.51 (d, J=8.0 Hz, 1H), 7.68 (s, 1H), 7.79 (d, J=2.0, 8.0 Hz, 1H), 7.85 (s, 1H), 7.91 (dd, J=2.0, 8.5 Hz, 1H), 8.31 (d, J=8.5 Hz, 1H); MS m/e 426 (MH⁺).

Anal. Calcd. for $C_{28}H_{27}NO_3 \cdot 0.125 H_2O$: C, 78.61; H, 6.42; N, 3.27. Found: C, 78.51; H, 6.46; N, 3.26.

EXAMPLE 163

4-[[(5,6-Dihydro-5,5-dimethyl-8-phenyl-2-naphthalenyl)carbonyl]amino]-3-methylbenzoic acid (I⁴g)

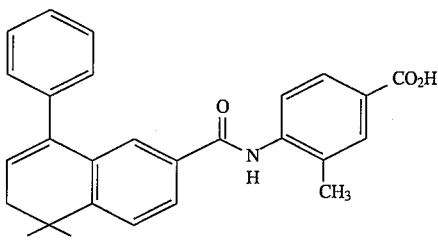

Using the same method given for the preparation of the 8-phenyl derivative I⁴a, 280 mg of compound I³q gave 223 mg (82% yield) of the title compound; ¹H-NMR (CDCl₃) δ1.37 (s, 6H), 2.20 (s, 3H), 2.39 (d, J=4.7 Hz, 2H), 6.07 (t, J=4.7 Hz, 1H), 7.30–7.42 (m, 5H), 7.45 (d, J=2.0 Hz, 1H), 7.51 (d, J=8.1 Hz, 1H), 7.68 (s, 1H), 7.78 (d, J=2.0, 8.1 Hz, 1H), 7.80 (s, 1H), 7.96 (dd, J=1.9, 8.6 Hz, 1H), 8.36 (d, J=8.6 Hz, 1H); MS m/e 412 (MH⁺).

Anal. Calcd. for $C_{27}H_{25}NO_3$: C, 78.81; H, 6.12; N, 3.40. Found: C, 78.68; H, 6.12; N, 3.40.

This invention is further illustrated by the following biological tests, which are illustrative only.

Rhino Mouse Study

Representatives from compounds of formula I were tested for their effect on utriculi reduction on rhino mouse and directly compared to all-trans retinoic acid.

Rhino mouse utriculi reduction assay

Six to nine week old female hairless rhino mice ($hr^{rh}/hr^{rh}$) were produced in the Bristol-Myers Squibb colony. Test retinoids in ethanol vehicle (50 ul) were applied to the dorsal area (approximately 1.5×3 cm$^2$) of rhino mice once daily for 5 days (Monday to Friday). For various retinoids, a dose response was obtained with concentrations ranging from 0.00033 mM to 16.5 mM. The animals were sacrificed on the following Monday by $CO_2$ inhalation. A ⅞" full thickness punch was taken from the central dorsal area of each animal. The epidermis of the biopsy was removed from the dermis after incubation in 0.5% acetic acid overnight at 4° C. The separated epidermis was then fixed in formalin, dehydrated with ethanol, and cleared in xylene. To determine the utriculi diameter, each epidermis sheet was placed on a glass slide in xylene. For each specimen, the diameter of 40 utricules was measured with an image analysis system (IBM PC, Image Measure program and Olympus microscope with video camera). % Utriculi reduction was calculated as $$\left(1 - \frac{\text{utriculi diameter in the test group}}{\text{utriculi diammeter in the ethanol control group}}\right) \times 100\%$$

Since the maximum effect in this assay is approximately 60% utriculi reduction, the activity of various test compounds is reported as $ED_{30}$ in Table 1, the concentration to reach 30% (half-maximum) utriculi reduction.

TABLE 1

| Compound* | $ED_{30}$ (mM) |
|---|---|
| $I^4a$ | 1.25 |
| $I^4d$ | 0.931 |
| $I^4e$ | 0.123 |
| $I^4f$ | 0.038 |
| $I^{30}a$ | 2.35 |
| $I^{33}a$ | 0.86 |
| $I^4k$ | 3.12 |

*The following compounds were not active in this Rhino mouse model: $I^2c$, $I^{10}a$, $I^{11}a$, $I^{16}a$, $I^{31}a$, $I^{32}a$, $I^4p$ and $I^4q$ The following biological test indicates that the compounds of the instant invention possess cytotoxicity activity normally associated with retinoids. Thus in one aspect, the invention provides a method of treating various tumors.

Cytotoxicity Result

The cytotoxicity assay was set up similar to those run by the National Cancer Institute (D. A. Scudiero, et al, "Evaluation of a Soluble Tetrazolium/Formazan Assay for Cell Growth and Drug Sensitivity in Culture Using Human and Other Tumor Cell Lines", *Cancer Research*, 48, 4827–4833, Sep. 1, 1988; M. C. Alley, et al, "Feasibility of Drug Screening with Panels of Human Tumor CellLines Using a Microculture Tetrazolium Assay", *Cancer Research*, 48, 589–601, Feb. 1, 1988) with the exception that the new vital stain alamarBLue™ was used to determine cellular viability. Briefly, the assayed involved plating 1000 cells per well in a volume of 120 µL in a 96 well flat-bottom dish (Corning) on day −1. Twenty-four hours later the appropriate dilution of a compound of formula I was added in a volume of 30 µL complete medium (final volume 150 µL). The plates were sealed with a plate sealer (Dynatech Labs) to prevent evaporation. On day 5 the mylar film was removed and 15 µL of sterile alamarBlue was added to each well and the cells were incubated 37° C. 5% $CO_2$ for two hours. Using a Vmax plate reader the optical density for each well was determined having the $OD_{570}$ subtracted from the $OD_{600}$. The 100% signal was determined for cells grown in complete medium containing only 0.5% DMSO. All wells were set-up in triplicate and the mean values were plotted in FIGS. 1, 2 and 3. The $IC_{50}$ values were determined for the second experiment and are listed in table 2.

TABLE 2

| $IC_{50}$ values for L2987 experiment 2 | |
|---|---|
| Compound | $IC_{50}$ (µM) |
| All trans retinoic acid | 68 |
| $I^4a$ | 51 |
| $I^{10}a$ | 47 |
| $I^4g$ | 38 |
| $I^4d$ | 28 |
| $I^{30}a$ | 60 |
| $I^{26}a$ | 48 |
| $I^{12}a$ | >100 |
| $I^6a$ | 28 |

Antiarthric Test

Compound $I^{11}a$ was also evaluated in a classical animal model for rheumatoid arthritis, i.e. in the collagen induced arthritis (CIA) model as described by Trentham et al in Collagen arthritis as a relevant model for rheumatoid arthritis. Evidence pro and con, *Arthritis Rheum* 25: 911–916 (1982); and Autoimmunity to type II collagen: an experimental model of arthritis. *J. Exp. Med* 146: 857–868 (1977).

In our protocol, drug treatment began three days prior to the first intradermal injection of 100 µg of type II collagen in Freund's complete adjuvant. At day 7, a second booster injection of collagen was given. Typically, animals begin to manifest symptoms of arthritis, such as joint swelling, around day 30. Daily i.p. administration of compound $I^{11}a$ at a concentration of 10 mg/kg and 30 mg/kg in a volume of 10 ml/kg were given. Clinical score by visual assessment of three parameters (swelling, joint deformation, and ankylosis) was performed daily to determine the onset of symptoms (see FIG. 4). At the end of the experiment period (day 70), animals were sacrificed and the joints were evaluated for histological changes. These changes were graded as 1 for synovial hypertrophy, 2 for pannus erosion into cartilage, 3 for pannus erosion into bone, and 4 for loss of joint integrity.

As shown in FIG. 4, the mean clinical score per animal remains normal until about day 30. In vehicle treated animals, the clinical score increases linearly to about 2.5 (maximum of 4.0) at day 65 indicating well established arthritis in these animals. By contrast, animals treated with compound $I^{11}a$ showed a marked reduction in the mean clinical score over the same time period. At day 65, the mean score was 0.6 with a small number of animals exhibiting joint swelling (grade 1) as the only obvious clinical symptom. However, most of the limbs evaluated were normal in appearance.

Preliminary data in this model with 30 mg/kg showed complete absence of disease at the visual and histological levels.

The compounds of formula I may be used topically or systemically, as anticancer agents and in the treatment, amelioration, or prevention of the skin disorders for which retinoic acid and other retinoids are useful. In this regard, they may be used for therapy in animals, including humans, for premalignant epithelial cell lesions, as a prophylaxis against tumor promotion in epithelial cells and treatment for dermatoses such as ichthyoses, follicular disorders, benign epithelial disorders, and other proliferative skin diseases (nonnmalignant conditions of the skin that are characterized by epidermal cell proliferation or incomplete cell differentiation) such as ache, psoriasis, eczema, atopic dermatitis, nonspecific dermatitis and the like, The compounds of formula I may also be used in reversing and preventing the effects of irradiation damage to skin, The compounds of formula I may also be used to treat rheumatic illnesses, including but not limited to, rheumatoid arthritis, psoriatic arthropathy, Reiter's disease, and cutaneous lupus erythematosus. The compounds of formula I have an additional use in the treatment of osteoarthritis.

When used for the above treatments they will usually be formulated with a pharmaceutically acceptable liquid, semisolid, or solid carrier. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation art. The carrier may be organic or inorganic in nature. Examples of pharmaceutically acceptable carriers that may be used to formulate a compound of formula I are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases such as treatment of severe cystic acne, oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0.002% to 1% by weight.

For topical administration the compounds of formula I are conveniently provided in the form of unguents, gels, creams, ointments, powders, dyeing compositions, solutions, suspensions, emulsions, lotions, sprays, adhesive plasters and impregnated pads. The compounds according to the invention can be mixed with inert nontoxic, generally liquid or pasty, bases suitable for topical treatment. Preparation of such topical formulations are well described in the art of pharmaceutical formulations as exemplified, for example, Remington's Pharmaceutical Science, Edition 17, Mack Publishing Company, Easton, Pa. Other medicaments can be added to such topical formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitably administered at the rate of 2 µg to 100 mg per day per kg of body weight. The required dose can be administered in one or more portions. For oral administration, suitable forms are, for example, tablets, pills, dmgees, syrups, suspensions, emulsions, solutions, powders and granules; a preferred method of administration consists in using pills containing from 0.1 mg to about 1 mg of active substance.

U.S. Pat. No. 4,876,381 issued on Oct., 24, 1989 to Lang et al. provides examples of formulations constituting gel, unguent, powder, cream, etc. for a retinoid compound. The aforesaid U.S. Patent can be used as a guide to formulate a compound of formula I and is herein incorporatedby reference in its entirety.

Isotretinoin (Accutane®) and etretinate (Tegison®) are used clinically to treat severe recalcitrant cystic ache and severe recalcitrant psoriasis, including the erythrodermica and generalized pustular types, respectively. Their mode of use is amply illustrated in the Physician's Desk Reference, 47th Edition, 1993, published by Medical Economics Data. The compounds of formula I may also be used to treat severe recalcitrant cystic acne or severe recalcitrant psoriasis. In so doing, the compounds of the present invention may be used in a similar fashion to isotretinoin and etretinate; thus, the relevant sections on isotretinoin and etretinate in the Physician's Desk Reference will serve as a convenient guide which will obviate the need for any undue experimentation.

The compounds according to the invention can also be administered parenterally in the form of solutions or suspensions for intravenous, intraperitoneal or intramuscular perfusions or injections. In that case, the compounds according to the invention are generally administered at the rate of about 2 µg to 100 mg per day per kg of body weight; a preferred method of administration consists of using solutions or suspensions containing approximately from 0.01 mg to 1 mg of active substance per ml.

Several retinoids have been found to possess antitumor properties. Roberts, A. B. and Sporn, M. B. in "The Retinoids," Sporn, M. B., Roberts, A. B., and Goodman, D. S., eds, 1984, 2 pp. 209–286, Academic Press, New York; Lippman, S. M., Kessler, J. F., and Meyskens, F. L., *Cancer Treat. Rep.*, 1987, 71, p. 391; ibid., p. 493. As used herein, the term "anti-tumor" includes both chemopreventative (prophylactic or tumor promotion inhibiting) and therapeutic (curative) use. For example, all-trans retinoic acid can be used to treat acute promyelocytic leukemia. Huang, M. et al., *Blood*, 1988, 72., p. 567. Isotretinoin has been shown to be useful in prevention of second primary tumors in squamous-cell carcinoma of the head and neck. Hong, W. K. et al., *N. Engl. J. Med.*, 1990, 323, p. 795.

The compounds of formula I can also be used in substantially the similar manner to retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula I in squamous-cell carcinoma of the head and neck, an oncologist may refer to the study by Hong, W. K. et al. in *N. Engl. J. Med.*, 1990, 323, p. 795. For treating acute promyelocytic leukemia, s/he may refer to the study by Huang, M. et al. in *Blood*, 1988, 72, p. 567.

We claim:

1. A compound of formula I or a nontoxic pharmaceutically acceptable salt, physiologically hydrolyzable ester or solvate thereof, in which X is —O—CO—, —NH—CO—, —CS—NH—, —CO—O—, —CO—NH—, —COS—, —SCO—, —SCH$_2$—, —CH$_2$—CH$_2$—, —C≡C—, —CH$_2$—NH—, —COCH$_2$—, —NHCS—, —CH$_2$S—, —CH$_2$O—, —OCH$_2$—, —NHCH$_2$— or —CR$^5$=CR$^6$—;

R$^m$ and R$^k$ are independently hydrogen, halogen, C$_{1-6}$alkyl, hydroxy, C$_{1-6}$alkyloxy or nitro;

n is zero or one;

R$^4$ is —(CH$_2$)$_t$—Y, C$_{1-6}$alkyl, or C$_{3-6}$cycloalkyl;

R$^1$ is —CO$_2$Z, C$_{1-6}$alkyl, CH$_2$OH, —CONHR$^y$, or CHO;

R$^2$ and R$^3$ are independently hydrogen or C$_{1-6}$alkyl;

R$^a$ and R$^b$ are independently hydrogen or C$_{1-6}$alkyl; but when n is one, R$^a$ and R$^b$ together can form a radical of the formula Y is naphthyl or phenyl, both radicals can be optionally substituted with one to three same or different C$_{1-6}$alkyl or halogen;

Z is hydrogen or C$_{1-6}$alkyl;

R$^5$, R$^6$ and R$^y$ are independently hydrogen or C$_{1-6}$alkyl; and t is zero to six.

2. A compound of claim 1 in which R$^1$ is —CO$_2$H; n is one; R$^2$ and R$^3$ are independently methyl or hydrogen; and R$^a$ and R$^b$ are independently hydrogen or C$_{1-6}$alkyl.

3. The compound of claim 2 that is 4-[[(5,6-dihydro-5,5-dimethyl-8-ethyl-2-naphthalenyl)amino]carbonyl]benzoic acid.

4. The compound of claim 2 that is 4-[[(5,6-dihydro-5,5,8-trimethyl-2-naphthalenyl)amino]carbonyl]benzoic acid.

5. The compound of claim 2 that is 4-[[(5,6-dihydro-5,5-dimethyl-8-phenyl-2-naphthalenyl)amino]carbonyl]benzoic acid.

6. The compound of claim 2 that is 4-[[(5,6-dihydro-5,5-dimethyl-8-ethyl-2-naphthalenyl)carbonyl]amino]benzoic acid.

7. The compound of claim 2 that is 4-[[(5,6-dihydro-5,5,8-trimethyl-2-naphthalenyl)carbonyl]amino]benzoic acid.

8. The compound of claim 2 that is 4-(E)-[2-(5,6-dihydro-5,5-dimethyl-8-phenyl-2-naphthalenyl)-1-propenyl]benzoic acid.

9. The compound of claim 2 that is 4-[[(5,6-dihydro-5,5-dimethyl-8-phenyl-2-naphthalenyl)oxy]carbonyl]benzoic acid.

10. The compound of claim 2 that is 4-[[(5,6-dihydro-5,5-dimethyl-8-phenyl-2-naphthalenyl)carbonyl]amino]benzoic acid.

11. The compound of claim 2 that is 4-[[(5,6-dihydro-5,5-dimethyl-8-phenyl-2-naphthalenyl)carbonyl]oxy]benzoic acid.

12. The compound of claim 2 that is 4-[[[5,6-dihydro-5,5-dimethyl-8-(2-fluorophenyl)-2-naphthalenyl]carbonyl]amino]benzoic acid.

13. The compound of claim 2 that is 4-[[(5,6-dihydro-5,5,6-trimethyl-8-phenyl-2-naphthalenyl)carbonyl]amino]benzoic acid.

14. The compound of claim 2 that is 4-[[(5,6-dihydro-5,5,7-trimethyl-8-phenyl-2-naphthanenyl)carbonyl]amino]benzoic acid.

15. The compound of claim 2 that is 4-[[(E)-(5,6-dihydro-5,5-dimethyl-8-phenyl)-2-naphthalenyl]vinyl]benzoic acid.

16. The compound of claim 2 that is 4-[[[(5,6-dihydro-5,5-dimethyl-8-phenyl)-2-naphthalenyl]carbonyl]sulfamyl]benzoic acid.

17. The compound of claim 2 that is 4-[[[(5,6-dihydro-5,5-dimethyl-8-phenyl)-2-naphthalenyl]sulfamyl]carbonyl]benzoic acid.

18. The compound of claim 2 that is 4-[[(5,6-dihydro-5,5-dimethyl-8-phenyl)-2-naphthalenyl]ethyl]benzoic acid.

19. The compound of claim 2 that is 4-[[[(5,6-dihydro-5,5-dimethyl-8-phenyl)-2-naphthalenyl]thiocarbonyl]amino]benzoic acid.

20. The compound of claim 2 that is 4-[[[(5,6-dihydro-5,5-dimethyl-8-phenyl)-2-naphthalenyl]carbonyl]methyl]benzoic acid.

21. The compound of claim 2 that is 4-[[[(5,6-dihydro-5,5-dimethyl-8-phenyl)-2-naphthalenyl]methyl]oxy]benzoic acid.

22. The compound of claim 2 that is 4-[[[(5,6-dihydro-5,5-dimethyl-8-phenyl)-2-naphthalenyl]oxy]methyl]benzoic acid.

23. The compound of claim 2 that is 4-[[[[5,6-dihydro-5,5-dimethyl-8-(2,4-dimethylphenyl)]-2-naphthalenyl]carbonyl]amino]benzoic acid.

24. The compound of claim 2 that is 4-[[[[5,6-dihydro-5,5-dimethyl-8-(4-methylphenyl)]-2-naphthalenyl]carbonyl]amino]benzoic acid.

25. The compound of claim 2 that is 4-[[(5,6-dihydro-5,5-dimethyl-8-phenyl)-2-naphthalenyl]ethynyl]benzoic acid.

26. The compound of claim 2 that is 4-[[[(5,6-dihydro-5,5-dimethyl-8-phenyl)-2-naphthalenyl]sulfamyl]methyl]benzoic acid.

27. The compound of claim 2 that is 4-[[(5,6-dihydro-5,5-dimethyl-8-phenyl)-2-naphthalenyl]methyl]amino]benzoic acid.

28. The compound of claim 2 that is 4-[[[(5,6-dihydro-5,5-dimethyl-8-phenyl)-2-naphthalenyl]amino]thiocarbonyl]benzoic acid.

29. The compound of claim 2 that is 4-[[[(5,6-dihydro-5,5-dimethyl-8-phenyl)-2-napthalenyl]methyl]sulfamyl]benzoic acid.

30. The compound of claim 2 that is 4-[[[(5,6-dihydro-5,5-dimethyl-8-phenyl)-2-naphthalenyl]amino]methyl]benzoic acid.

31. The compound of claim 2 that is 4-[[[(5,6-dihydro-5,5-dimethyl-8-phenyl)-2-naphthalenyl]carbonyl]amino]-2-hydroxybenzoic acid.

32. The compound of claim 2 that is 4-[[[(5,6-dihydro-5, 5-dimethyl-8-phenyl)-2-naphthalenyl]carbonyl]amino]-2-fluorobenzoic acid.

33. The compound of claim 2 that is 4-[[[(5,6-dihydro-5, 5-dimethyl-8-phenyl)-2-naphthalenyl]carbonyl]amino]-2-nitrobenzoic acid.

34. The compound of claim 2 that is 4-[[[(5,6-dihydro-5, 5-dimethyl-8-phenyl)-2-naphthalenyl]carbonyl]amino]-2-methoxybenzoic acid.

35. The compound of claim 2 that is 4-[[[(5,6-dihydro-5, 5-dimethyl-8-(2-naphthalene)]-2-naphthaleny]carbonyl]amino]benzoic acid.

36. The compound of claim 2 that is 4-[[(5,6-dihydro-8-phenyl-2-naphthalenyl)carbonyl]amino]benzoic acid.

37. The compound of claim 2 that is 4-[[(5,6-dihydro-5, 5-dimethyl-8-phenyl-2-naphthalenyl)carbonyl]amino]-3-fluorobenzoic acid.

38. The compound of claim 2 that is 4-[[(5,6-dihydro-5, 5-dimethyl-8-phenyl-2-naphthalenyl)carbonyl]amino]-3-methylbenzoic acid.

39. A compound of claim 1 in which $R^1$ is —$CO_2H$; X is —CONH—; $R^2$ and $R^3$ are methyl; and $R^a$ and $R^b$ together form a radical of the formula

40. The compound of claim 39 that is 4-[[(5,8,10,10a-tetrahydro-10,10-dimethyl-9-phenyl-2-anthracenyl)carbonyl]amino]benzoic acid.

41. A compound of claim 1 in which $R^1$ is —$CO_2H$; n is zero; and $R^2$ and $R^3$ are methyl.

42. The compound of claim 41 that is 4-[[(1,1-dimethyl-3-phenyl-1H-inden-5-yl)amino]carbonyl]benzoic acid.

43. The compound of claim 41 that is 4-[(1,1-dimethyl-3-phenyl-1H-inden-5-yloxymethyl)benzoic acid.

44. The compound of claim 41 that is 4-[2-(1,1-dimethyl-3-phenyl-1H-inden-5-yl)vinyl]benzoic acid.

45. The compound of claim 41 that is 4-[(1,1-dimethyl-3-phenyl-1H-indene-5-carbonyl)amino]benzoic acid.

46. A pharmaceutical composition comprising a compound as claimed in claim 1.

* * * * *